(12) United States Patent
Farina et al.

(10) Patent No.: US 7,220,769 B2
(45) Date of Patent: May 22, 2007

(54) AZOLYLBENZAMIDES AND ANALOGUES AND THEIR USE FOR TREATING OSTEOPOROSIS

(75) Inventors: Carlo Farina, Baranzate di Bollate (IT); Stefania Gagliardi, Baranzate di Bollate (IT); Shahzad Sharooq Rahman, Harlow (GB)

(73) Assignee: Nikem Research S.R.L., Milan (IT)

( * ) Notice: Subject to any disclaimer, the term of this patent is extended or adjusted under 35 U.S.C. 154(b) by 0 days.

(21) Appl. No.: 10/868,090

(22) Filed: Jun. 14, 2004

(65) Prior Publication Data

US 2005/0038095 A1 Feb. 17, 2005

Related U.S. Application Data

(63) Continuation of application No. 10/019,105, filed as application No. PCT/EP00/05881 on Jun. 23, 2000, now abandoned.

(30) Foreign Application Priority Data

Jun. 24, 1999 (GB) .................................. 9914825

(51) Int. Cl.
*A61K 31/4188* (2006.01)
*A61K 31/4184* (2006.01)
*C07D 491/02* (2006.01)

(52) U.S. Cl. ................... 514/393; 514/394; 548/304.4; 548/302.1

(58) Field of Classification Search ................ 514/393, 514/394; 548/304.4, 302.1
See application file for complete search history.

(56) References Cited

U.S. PATENT DOCUMENTS 4,093,726 A 6/1978 Winn et al.

FOREIGN PATENT DOCUMENTS

| WO | WO 95/30659 | 11/1995 |
|----|-------------|---------|
| WO | WO 97/12615 | 4/1997 |
| WO | WO 98/01436 | 1/1998 |
| WO | WO 99/33822 | 7/1999 |

OTHER PUBLICATIONS

Novelli, et al., "Synthesis and Biological Investigations of 2-(Tetrahydropyran-2'-yl) and 2-(Tetrahydrofuran-2'-yl)Benzimidazoles", (1997), II Farmaco, 52(8-9), pp. 499-507.

Tsukamoto, et al., "Synthesis and Antiinflammatory Activity of Some 2-(Substituted-pyridnyl)benzimidazoles", (1980), J. Med. Chem., 23, pp. 734-738.

Barraclough, et al., "Intropic 2-arylimidazol[1,2-a]pyrimidines", (1992), Eur. J. Med. Chem., 27, pp. 207-217.

King, et al., "Synthesis and Thermal Reactions of 1,2-Dihydro-1,2,4-benzotriazines", (1998), J. Chem. Soc., Perkins Trans 1 No 12 pp 3381-3385.

Piguet, et al., "Synthesis of Segmental Heteroleptic Ligands for the Self-Assembly of Heteronuclear Helical Supramolecular Complexes", (1994), Helvetica Chimica Acta, vol. 77, pp. 931-942.

Database Crossfire 'Online!, Beilstein Institit zur Foerderung der Chemischen Wissenchaften, (XP002149940), Beilstein Registry No. 5988985 and 6009580 & Heterocycles, vol. 21, No. 6, (1985) pp. 1425-1430.

Database Crossfire 'Online!, Beilstein Institut zur Foerderung der Chemischen Wissenchaften, (XP002149941), Beilstein Registry No. 208984, 208985, 223809 and 298960 & Hel. Chim. acta, vol. 4 1921, pp. 428, 429, 436.

Database Crossfire 'Online!, Beilstein Institut zur Foerderung der Chemischen Wissenchaften, (XP002149942), Beilstein Registry No. 42810 and 25529 & G;as/ Je/ Dris/ Bepgrad. vol. 21, 1956, pp. 95, 98.

Database Crossfire 'Online!, Beilstein Institut zur Foerderung der Chemischen Wissenchaften, (XP002149943), Beilstein Registry No. 6003643 and J. Prakt. Chem., vol. 331, No. 4, 1989, pp. 649-658.

Farina, et al., "Selective inhibitors of vacuolar H+ -ATPase of osteoclasts with bone antiresorptive activity", (1999), Expert Opinion on Therapeutic Patents, vol. 9, No. 2, pp. 157-168.

Vasikaran et al., Bisphosphonates: an overview with special reference to alendronate. Ann. Clin. Biochem. 38: 608-623, 2001.

*Primary Examiner*—Kamal A. Saeed
(74) *Attorney, Agent, or Firm*—Wolf, Greenfield & Sacks, P.C.

(57) ABSTRACT

A compound of formula (I) or a salt thereof, or a solvate thereof, wherein: X represents oxygen, sulphur, or $NR_b$; Y and Z each independently represent nitrogen, CH, $CR_1$ or $CR_2$; A represents an unsubstituted or substituted aryl group or an unsubstituted or substituted heterocyclyl group; $R_a$ represents —$C(O)NR_sR_t$; $R_1$ and $R_2$ each independently represents hydrogen or specific substituents; and the use of such a compound in the treatment and/or prophylaxis of diseases associated with over activity of osteoclasts in mammals.

8 Claims, No Drawings

AZOLYLBENZAMIDES AND ANALOGUES AND THEIR USE FOR TREATING OSTEOPOROSIS

RELATED APPLICATIONS

This application is a continuation of U.S. patent application Ser. No. 10/019,105 filed Dec. 20, 2001 now abandoned; which is a national stage filing under 35 U.S.C. § 371 of PCT International Application PCT/EP00/05881, filed Jun. 23, 2000 and published under PCT Article 21(2) in English, which is herein incorporated by reference in its entirety.

This invention relates to certain novel compounds, to a process for preparing such compounds, to pharmaceutical compositions containing such compounds and to the use of such compounds and compositions in medicine.

Diseases associated with loss of bone mass are known to be caused by over activity of osteoclast cells. It is also known that certain compounds, usually related to bafilomycin, are useful for treating such diseases. For example International Application Publication Number WO 91/06296 (Astra Aktiebolaget) discloses certain bafilomycin macrolides for the treatment of bone affecting diseases.

However, bafilomycin derivatives are not selective for osteoclasts in humans. The use of these compounds is therefore associated with unacceptable toxicity due to generalised blockade of other essential v-ATPases. Indeed, to date there is no known treatment which is selective for the human osteoclasts.

The search for a successful treatment for diseases associated with loss of bone mass in humans is further complicated in that the nature of the therapeutic target for the selective inhibition of the osteoclasts is controversial. Thus Baron et al. (International Application Publication Number WO 93/01280) indicate that a specific vacuolar ATPase (v-ATPase) has been identified in osteoclasts as a potential therapeutic target. However, the Baron work was carried out in chickens and Hall et al. (*Bone and Mineral* 27, 159–166, (1994)), in a study relating to mammals, conclude that in contrast to avian osteoclast v-ATPase, mammalian osteoclast v-ATPase is pharmacologically similar to the v-ATPase in other cells and, therefore, it is unlikely to be a good therapeutic target.

WO 95/30659 (Warner-Lambert Company) discloses certain benzimidazole and imidazopyridine derivatives as dopaminergic agents.

We have now found a group of compounds which are selective for mammalian osteoclasts, acting to selectively inhibit their bone resorbing activity. These compounds are therefore considered to be particularly useful for the treatment and/or prophylaxis of diseases associated with loss of bone mass, such as osteoporosis and related osteopenic diseases, Paget's disease, hyperparathyroidism and related diseases. These compounds are also considered to possess anti-tumour activity, antiviral activity (for example against Semliki Forest, Vesicular Stomatitis, Newcastle Disease, Influenza A and B, HIV viruses), antiulcer activity (for example the compounds may be useful for the treatment of chronic gastritis and peptic ulcer induced by *Helicobacter pylori*), immunosuppressant activity, antilipidemic activity, antiatherosclerotic activity and to be useful for the treatment of AIDS and Alzheimer's disease. Furthermore, these compounds are also considered useful in inhibiting angiogenesis i.e. the formation of new blood vessels which is observed in various types of pathological conditions (angiogenic diseases) such as rheumatoid arthritis, diabetic retinopathy, psoriasis and solid tumours.

Accordingly, the invention provides a compound of formula (I)

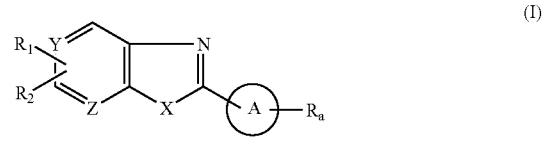

or a salt thereof, or a solvate thereof, wherein;

X represents oxygen, sulphur, or $NR_b$ wherein $R_b$ represents hydrogen, unsubstituted or substituted $C_{1-6}$alkyl, or $C_{1-6}$alkylcarbonyl wherein the alkyl moiety may be unsubstituted or substituted;

Y and Z each independently represent nitrogen, CH, $CR_1$ or $CR_2$;

A represents an unsubstituted or substituted aryl group or an unsubstituted or substituted heterocyclyl group;

$R_a$ represents —$C(O)NR_sR_t$ wherein $R_s$ and $R_t$ each independently represent hydrogen, unsubstituted or substituted $C_{1-6}$alkyl, unsubstituted or substituted $C_{3-8}$cycloalkyl, unsubstituted or substituted $C_{1-6}$alkenyl, unsubstituted or substituted aryl, aryl$C_{1-6}$alkyl wherein both the aryl and alkyl moieties may be unsubstituted or substituted, unsubstituted or substituted heterocyclyl or an unsubstituted or substituted heterocyclyl$C_{1-6}$alkyl group, or $R_s$ and $R_t$ together with the nitrogen to which they are attached form a heterocyclyl group;

$R_1$ and $R_2$ each independently represents hydrogen, hydroxy, amino, $C_{1-6}$alkoxy, aryloxy wherein the ary moiety may be unsubstituted or substituted, unsubstituted or substituted benzyloxy, $C_{1-6}$alkylamino, di($C_{1-6}$alkyl)amino, halo, trifluoromethyl, trifluoromethoxy, nitro, $C_{1-6}$alkyl, carboxy, alkoxycarbonyl, carbamoyl, $C_{1-6}$alkylcarbamoyl, or $R_1$ and $R_2$ together represent methylenedioxy, —(CH═CH)$_{2-3}$—, carbonyldioxy or carbonyldiamino.

Examples of aryl groups represented by A include phenyl.

Examples of heterocyclyl groups represented by A include thiophene.

Preferably, A is unsubstituted or substituted phenyl or unsubstituted or substituted thiophenyl.

Suitably, $R_1$ and $R_2$ each independently represents hydrogen, trifluoromethyl, methyl, hydroxy or methoxy or a halogen substituent, for example chloro, bromo or fluoro.

Suitable positions for substitution for $R_1$ or $R_2$ are the 4, 5, 6 or 7 position, favourably the 5 or 6 position.

Preferably, $R_1$ is bromo, chloro, especially 5-chloro, or methyl.

Preferably, $R_2$ is chloro, especially 6-chloro; or methyl, especially 6-methyl.

Suitably, X represents $NR_b$.

Favourably, X represents NH.

Favourably, Y represents $CR_1$.

Favourably, Z represents CH.

When $R_s$ or $R_t$ represent $C_{1-6}$alkyl favourable groups are ethyl, propyl or butyl.

When $R_s$ or $R_t$ represent substituted $C_{1-6}$alkyl, favoured groups are 3-aminopropyl, 3-hydroxypropyl, diethylaminoethyl, diethylaminopropyl, morpholinopropyl, 2-(di $C_{1-6}$alkylamino)ethyl, 3-(di$C_{1-6}$alkyl)aminopropyl, 4-(di$C_{1-6}$alkyl)aminobutyl, 3-[4-(3-chlorophenyl)piperazin-1-yl]

propyl, 3-[4-(2-methoxy-5-chlorophenyl)piperazin-1-yl]propyl, 3-[4-(2-pyrimidinyl)piperazin-1-yl]propyl, 3-heterocyclylmethyl, (3-pyridyl)methyl, heterocyclylethyl or heterocyclylpropyl groups.

When Rs or Rt represent substituted cycloalkyl, suitable substituents include hydroxy, $C_{1-6}$alkyl, $C_{1-6}$alkoxy, and halogen.

When $R_s$ or $R_t$ represent heterocyclyl, a favoured group is 3-quinuclidyl or 1-azabicyclo[2.2.2]octan-3-yl.

Suitably, $R_s$ represents 3-pyridyl, 2-methoxy-5-pyridyl, unsubstituted or substituted heterocyclyl and unsubstituted or substituted aryl.

In a favoured aspect, $R_s$ represents an unsubstituted or substituted piperidinyl group, especially a 4-piperidinyl group, or a piperazinyl group, especially a piperazin-1-yl group either unsubstituted or substituted, especially at position 4.

Subsituents for the piperidinyl ring of $R_s$ include $C_{1-6}$alkyl, aryl$C_{1-6}$alkyl, fused $C_{3-8}$cycloalkyl, hydroxy$C_{1-6}$alkyl, and polyhydroxy$C_{1-6}$alkyl.

Favoured substituents for piperidinyl groups are $C_{1-6}$alkyl groups, especially methyl groups.

When the piperidinyl group is substituted it is preferred if the substituents are attached to one or both of the carbon atoms alpha to the nitrogen atom.

An example of a substituted piperidinyl groups is a 1,2,2,6,6-pentamethylpiperidin-4-yl group, a 2,2,6,6-tetramethylpiperidin-4-yl group, 1-benzylpiperidinyl-4-yl group or a 1-(4-(3-iodobenzoyl)benzyl)piperidyn-4-yl group.

Substituents for the piperazinyl group of $R_s$ include unsubstituted or substituted aryl, especially unsubstituted phenyl or phenyl substituted with one or more groups independently selected from halogen, especially chloro; and $C_{1-6}$alkoxy, especially methoxy.

Preferably, Rs is a 1,2,2,6,6-pentamethylpiperidin-4-yl group or a 2,2,6,6-tetramethylpiperidin-4-yl group.

Suitably, $R_t$ is hydrogen.

There is a moiety, referred to herein as moiety (b), which forms part of formula (I) and which has the formula shown below

(b)

In one preferred aspect moiety (b) represents a moiety of formula (c)

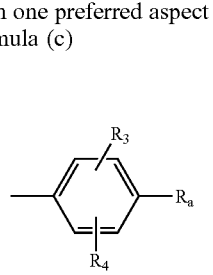

(c)

wherein;

$R_3$ represents hydrogen, hydroxy, $C_{1-6}$alkoxy, $C_{1-6}$alkythio, halogen or a group $NR_uR_v$ wherein $R_u$ and $R_v$ each independently represent hydrogen, $C_{1-6}$alkyl or $C_{1-6}$alkylcarbonyl.

$R_4$ represents hydrogen, $C_{1-6}$alkyl, or $C_{1-6}$alkoxy.

Suitably $R_3$ is located meta to $R_a$.

An example of $R_3$ is hydrogen, methoxy, ethoxy, methyl, chloro, fluoro and bromo.

Favourably, $R_3$ is methoxy, ethoxy, methyl, iso-propoxy, or bromo.

Favourably, $R_4$ is hydrogen or methoxy.

In a preferred aspect, $R_3$ and $R_4$ are not both hydrogen.

Alkyl groups referred to herein, including those forming part of other groups, include straight or branched chain alkyl groups containing up to six carbon atoms, said carbon atoms being optionally substituted with up to five, suitably up to three, groups selected from the list consisting of aryl, heterocyclyl, alkylthio, alkoxy, arylalkoxy, amino, mono- or di-alkylamino, cycloalkyl, cycloalkenyl, carboxy and esters thereof, mono- or dialkylaminosulphonyl, aminosulphonyl, cyano, alkylcarbonylamino, arylcarbonylamino, hydroxy, and halogen.

Alkenyl and alkynyl groups referred to herein include straight and branched chain alkenyl groups containing from two to six carbon atoms, said carbon atoms being optionally substituted with up to five, suitably up to three, groups including those substituents described hereinbefore for the alkyl group.

Cycloalkyl and cycloalkenyl groups referred to herein include groups having between three and eight ring carbon atoms, which carbon atoms are optionally substituted with up to five, suitably up to three, groups including those substituents described hereinbefore for the alkyl group.

When used herein the term "aryl" includes phenyl and naphthyl groups, especially phenyl.

Suitable optional substituents for any aryl group include up to three substituents selected from the list consisting of aryl, arylcarbonyl, alkylthio, halo, alkyl, alkenyl, substituted alkenyl, arylalkyl, alkoxy, alkoxyalkyl, haloalkyl, haloalkyloxy, hydroxy, hydroxyalkyl, nitro, amino, cyano, cyanoalkyl, mono- and di-N-alkylamino, acyl, acylamino, N-alkylacylamino, acyloxy, carboxy, carboxyalkyl, carboxyalkenyl, carbamoyl, mono- and di-N-alkylcarbamoyl, alkoxycarbonyl, aryloxy, arylthio, aralkyloxy, aryloxycarbonyl, aminosulphonyl, alkylaminosulphonyl, alkylthio, alkylsulphonyl, cycloalkyl, heterocyclyl, or a group —$NR_uR_v$, wherein $R_u$ and $R_v$ each independently represent hydrogen, alkyl or alkylcarbonyl.

Suitable aralkyl groups include aryl$C_{1-3}$alkyl groups such as phenylethyl and benzyl groups, especially benzyl.

Preferably, substituted aralkyl groups are substituted in the aryl moiety. When used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each ring suitably has from 4 to 7, preferably 5 or 6, ring atoms. A fused heterocyclic ring system may include carbocyclic rings and need include only one heterocyclic ring.

Suitable optional substituents for any heterocyclyl group includes those mentioned herein with respect to the aryl group.

As used herein, the term "halogen" or "halo" includes fluoro, chloro, bromo and iodo, suitably fluoro and chloro, favourably chloro.

When used herein "acyl" includes alkyl carbonyl.

Certain of the carbon atoms of the compounds of formula (I) are chiral carbon atoms and may therefore provide stereoisomers of the compound of formula (I). The invention extends to all stereoisomeric forms of the compounds of formula (I) including enantiomers and mixtures thereof, including racemates. The different stereoisomeric forms may be separated or resolved one from the other by conventional methods or any given isomer may be obtained by conventional stereospecific or asymmetric syntheses.

Suitable salts are pharmaceutically acceptable salts.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

Suitable pharmaceutically acceptable salts of carboxy groups include metal salts, such as for example aluminium, alkali metal salts such as sodium or potassium and lithium, alkaline earth metal salts such as calcium or magnesium and ammonium or substituted ammonium salts, for example those with $C_{1-6}$alkylamines such as triethylamine, hydroxy$C_{1-6}$alkylamines such as 2-hydroxyethylamine, bis(2-hydroxyethyl)amine or tri(2-hydroxyethyl)amine, cycloalkylamines such as dicyclohexylamine, or with procaine, 1,4-dibenzylpiperidine, N-benzyl-b-phenethylamine, dehydroabietylamine, N,N'-bisdehydroabietylamine, glucamine, N-methylglucamine or bases of the pyridine type such as pyridine, collidine or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) may be prepared by amidation of a suitable carboxylic acid with a suitable amine. Accordingly, the present invention provides a process for the preparation of a compound of formula (I) or a salt thereof or a solvate thereof which process comprises the amidation of a suitable carboxylic acid with a suitable amine. The present invention also provides a process for the preparation of a compound of formula (I) or a salt thereof or a solvate thereof, which process comprises the amidation of a compound of formula (II)

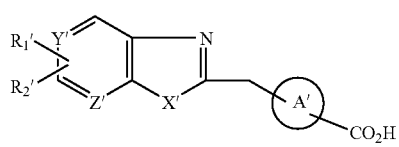

(II)

wherein X', Y', Z', A', $R_{1'}$ and $R_{2'}$ each respectively represent X, Y, Z, A, $R_1$ and $R_2$ respectively as defined in relation to formula (I) or a protected form thereof with a compound of formula (III)

$HNR_{s'}R_{t'}$ (III)

wherein $R_{s'}$ and $R_{t'}$ represent $R_s$ and $R_t$ respectively as defined in relation to formula (I) or a protected form thereof and thereafter, as necessary, carrying out one or more of the following steps;

(i) converting one compound of formula (I) into another compound of formula (I);
(ii) removing any protecting group;
(iii) preparing a salt or a solvate of the compound so formed.

Suitable amidation methods include treating the compound of formula (II) with a compound of formula (III).

The reaction between the compounds of formula (II) and (III) takes place after activation of the carboxyl group.

A carboxyl group may be activated in conventional manner, for example, by conversion into an acid anhydride, acid halide, acid azide or an activated ester such as cyanomethyl ester, thiophenyl ester, p-nitrophenyl ester, p-nitrothiophenyl ester, 2,4,6-trichlorophenyl ester, pentachlorophenyl ester, pentafluorophenyl ester, N-hydroxyphthalimido ester, 8-hydroxypiperidine ester, N-hydroxysuccinimide ester, N-hydroxybenzotriazole ester, or the carboxyl group may be activated using a carbodiimide such as N,N'-dicyclohexylcarbodiimide (DCC) or 1-ethyl-3-[3-(dimethylamino)propyl]-carbodiimide hydrochloride (WSC), either in the presence or the absence of hydroxybenzotriazole (HOBt) or 1-hydroxy-7-azabenzotriazole (HOAt) or it may be activated using N,N'-carbonyldiimidazole, Woodward-K reagent, Castro's reagent or an isoxazolium salt.

A compound of formula (II) may be prepared by cyclising a compound of formula (IV)

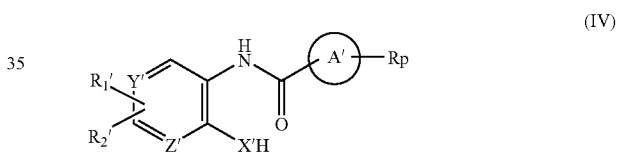

(IV)

wherein X', Y', Z', A', $R_{1'}$ and $R_{2'}$ are as defined in relation to formula (II) and $R_p$ represents a protected carboxyl group or a group convertible into a carboxyl group; and thereafter, as required, converting the group $R_p$ into a carboxyl group.

Suitably, the cyclisation reaction is carried out in an inert hydrocarbon solvent, such as xylene, in presence of a dehydrating agent such as $P_2O_5$, p-toluensulfonic acid or polyphosphoric acid at any temperature providing a suitable rate of formation of the required product, preferably at an elevated temperature, such as the reflux temperature of the solvent.

When $R_p$ is a protected carboxyl group, suitable groups include lower alkoxycarbonyl groups, for example methoxy- or ethoxycarbonyl groups, which may be removed by conventional hydrolysis methods, for example by use of basic hydrolysis using ethanolic potassium hydroxide.

When $R_p$ is a group convertible into a carboxyl group, suitable groups include the cyano group. Such groups may be converted into carboxyl groups using conventional methods for example when $R_p$ is a cyano group it may be converted into a carboxyl group by hydrolysis using conventional methods, for example by use of basic hydrolysis using potassium hydroxide solution in ethanol at reflux. A preferred value of $R_p$ is a cyano group.

A compound of formula (IV) is prepared by reacting a compound of formula (V)

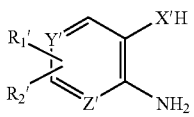

wherein X', Y', Z', $R_{1'}$ and $R_{2'}$ are as defined in relation to formula (II) with a compound of formula (VI)

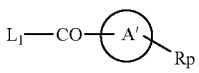

wherein A' and $R_p$ are as defined in relation to formula (IV) and $L_1$ represents a leaving group, such as a halogen group, for example a chloro group.

The reaction between the compounds of formula (V) and (VI) may be carried in an inert hydrocarbon solvent, such as dichloromethane, at any temperature providing a suitable rate of formation of the required product, preferably at room temperature and in presence of a base, preferably a tertiary amine such as triethylamine.

Alternatively compounds of formula II can be prepared by treating compound of formula V with compounds of formula VII following the procedure described in *Synthetic Communications* 1990, 20, 955–963.

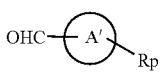

wherein A' and $R_p$ are as defined in relation to formula (IV).

The compounds of formula (V) are known, commercially available, or they are prepared using methods analogous to those used to prepare known compounds, such as those described in *J. March, Advanced Organic Chemistry*, 3rd Edition (1985), Wiley Interscience.

The compounds of formula (VI) are known, commercially available, or they are prepared using methods analogous to those used to prepare known compounds, such as those described in *J. March, Advanced Organic Chemistry*, 3rd Edition (1985), Wiley Interscience.

The compounds of formula (III) are known or they are prepared using methods analogous to those used to prepare known compounds, such as those described in J. March, *Advanced Organic Chemistry*, 3rd Edition (1985), Wiley Interscience.

The compounds of formula VII are known or they are prepared using methods described in literature such as those described in *Vogel's Textbook of Practical Organic Chemistry* in the section Aromatic Aldehydes, 5th Edition (1989), Longman Scientific & Technical or in Chem Ber., 1969, 102, 2502–2507; J. Med. Chem., 1997, 40, 2064–2084.

The conversion of one compound of formula (I) with X=NH into another compound of formula (I) with X=$NR_b$ may be carried out using the appropriate conventional procedure; for example the above mentioned conversion may be carried out (i) by reacting the compound of formula (I) with a strong base, for example sodium hydride, in a solvent such as dimethylformamide, followed by alkylation with an alkyl halide or alkyl sulphate or acylation with an acyl halide, or ii) by reacting the compound of formula (I) with a finely grounded solid base, for example potassium hydroxide, in a solvent such as acetone, followed by alkylation with an alkyl halide or acylation with an acyl halide.

Amines of general formula HNRs'Rt' may be prepared using the methods known in the art for the preparation of amines, for example as taught in *Houben-Weil, Methoden der Organischen Chemie*, Vol. XI/1 (1957) and Vol. E16d/2 (1992), Georg Thieme Verlag, Stuttgart.

Alternatively a compound of formula (I), wherein X is $NR_b$, may be prepared by solid phase chemistry after cleavage of a compound of formula (VIII) at the N-Resin bond. Accordingly, in a further aspect, there is provided a process for the preparation of a compound of formula (I), or a salt thereof or a solvate thereof, which process comprises the cleavage of a compound of formula (VIII) at the N-Resin bond.

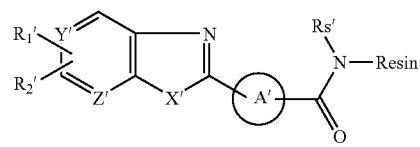

wherein X', Y', Z', A', $R_{1'}$, $R_{2'}$, and Rs' each respectively represent X, Y, Z, A, $R_1$, $R_2$ and Rs respectively as defined in relation to formula (I).

The cleavage reaction is carried out in a suitable mixture of solvents, such as dichloromethane and water, in presence of an organic acid, such as trifluoroacetic acid, at a suitable temperature providing a suitable rate of formation of the required product, preferably at room temperature.

A compound of formula (VIII) is prepared by reacting a compound of formula (IX)

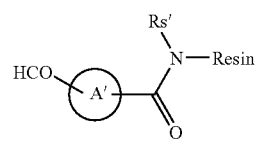

wherein A' and Rs' are defined in relation of formula (VIII) with a compound of formula (V)

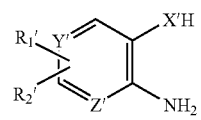

wherein X', Y', Z', $R_{1'}$ and $R_{2'}$ are as defined in relation to formula (VIII).

The reaction is carried out in a suitable solvent such as dimethylacetamide (DMA) in presence of a small quantity of organic acid, such as acetic acid, at a suitable temperature providing a suitable rate of formation of the required product, preferaby between 100° C. and the reflux temperature of the solvent.

A compound of formula (IX) is prepared by reacting a compound of formula (VII)

(VII)

wherein A' and Rp are as defined in relation of formula (IV) with a compound of formula (X)

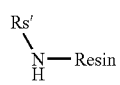
(X)

wherein Rs' is defined in relation of formula (VIII).

When $R_p$ is a protected carboxyl group, suitable groups include lower alkoxycarbonyl groups, for example methoxy- or ethoxycarbonyl groups, which may be removed by conventional hydrolysis methods, for example by use of basic hydrolysis using ethanolic potassium hydroxide.

When $R_p$ is a group convertible into a carboxyl group, suitable groups include the cyano group. Such groups may be converted into carboxyl groups using conventional methods for example when $R_p$ is a cyano group it may be converted into a carboxyl group by hydrolysis using conventional methods, for example by use of basic hydrolysis using potassium hydroxide solution in ethanol at reflux.

The reaction of compound of formula (VII) wherein Rp=—COOH with compound of formula (X) is carried out using suitable amidation methods and takes place after activation of the carboxylic group.

A carboxyl group may be activated in conventional manner, for example, by conversion into an acid anhydride, acid halide, acid azide or an activated ester such as cyanomethyl ester, thiophenyl ester, p-nitrophenyl ester, p-nitrothiophenyl ester, 2,4,6-trichlorophenyl ester, pentachlorophenyl ester, pentafluorophenyl ester, N-hydroxyphthalimido ester, 8-hydroxypiperidine ester, N-hydroxysuccinimide ester, N-hydroxybenzotriazole ester, or the carboxyl group may be activated using a carbodiimide such as N,N'-dicyclohexylcarbodiimide (DCC) or 1-ethyl-3-[3-(dimethylamino)propyl]carbodiimide hydrochloride (WSC), either in the presence or the absence of hydroxybenzotriazole (HOBt) or 1-hydroxy-7-azabenzotriazole (HOAt) or it may be activated using N,N'-carbonyldiimidazole.

A compound of formula (X) is obtained by linking compounds of formula (XI) on suitable resin derived from commercially available Merrifield resin H$_2$NR$_{s'}$ (XI)

wherein R$_{s'}$ represents R$_s$ as defined in relation to formula (I).

The resin is prepared by reaction of Merrifield resin with 4-hydroxy-2 methoxybenzaldehyde in a suitable solvent, such as DMF, in presence of a strong base, such as sodium hydride, at any temperature providing a suitable rate of formation of the required product, preferably at a temperature between 50–80° C.

The compounds of formula (XI) are known, commercially available, or they are prepared using methods analogous to those used to prepare known compounds, such as those described in *J. March, Advanced Organic Chemistry*, 3rd Edition (1985), Wiley Interscience.

The reaction between the compounds of formula (III) and the resin prepared as described above is carried out in a suitable solvent, such as DMF, in presence of a catalityc amount of acid, such as acetic acid, in presence of a reducing agent such as sodium triacethoxyborohydride, at a suitable temperature, preferably at room temperature.

A compound of formula (I) or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers and diastereoisomers by conventional means, for example by the use of an optically active acid as a resolving agent. Suitable optically active acids which may be used as resolving agents are described in "*Topics in Stereochemistry*", Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropriate silylating agent such as di-tert-butylsilylbis(trifluoromethanesulfonate): the silyl group may then be removed using conventional procedures such as treatment with hydrogen fluoride, preferably in the form of a pyridine complex and optionally in the presence of alumina, or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in aqueous ethanol or trifluoroacetic acid in methylene dichloride. An amino group may be protected as a benzyl derivative, prepared from the appropriate amine and a benzyl halide under basic conditions, the benzyl group being removed by catalytic hydrogenolysis, using for example a palladium on carbon catalyst.

Benzimidazole NH groups and the like may be protected using any conventional group, for example benzenesulphonyl, methylsulphonyl, tosyl, formyl, acetyl (all of them removable by treatment with alkaline reagents), benzyl (removable either with sodium in liquid ammonia or with AlCl3 in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl)ethoxymethyl (SEM) (removable by treatment with tetrabutylammonium fluoride in the presence of ethylenediamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group is any group that will, under the reaction conditions, cleave from the starting material, thus promoting reaction at a specified site. Suitable examples of such groups unless otherwise specified are halo, mesyloxy, p-nitrobenzenesulphonyloxy and tosyloxy groups.

The salts, esters, amides and solvates of the compounds mentioned herein may as required be produced by methods conventional in the art: for example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_sR_{t'}$ may be prepared by treating the relevant carboxylic acid with an amine of formula $HNR_sR_{t'}$ wherein $R_{s'}$ and $R_{t'}$ are as hereinbefore defined. Alternatively, a $C_{1-6}$ alkyl ester such as a methyl ester of the acid may be treated with an amine of the above defined formula $HNR_sR_{t'}$ to provide the required amide, optionally in presence of trimethylaluminium following the procedure described in Tetrahedron Lett. 48, 4171–4173, (1977).

As mentioned above the compounds of the invention are indicated as having useful therapeutic properties.

Of particular interest is the osteoporosis associated with the peri and post menopausal conditions. Also encompassed are the treatment and prophylaxis of Paget's disease, hypercalcemia associated with bone neoplasms and all the types of osteoporotic diseases as classified below according to their etiology:

Primary Osteoporosis
Involutional
Type I or postmenopausal
Type II or senile
Juvenile
Idiopathic in young adults Secondary Osteoporosis
Endocrine abnormality
Hyperthyroidism
Hypogonadism
Ovarian agenesis or Turner's syndrome
Hyperadrenocorticism or Cushing's syndrome
Hyperparathyroidism
Bone marrow abnormalities
Multiple myeloma and related disorders
Systemic mastocytosis
Disseminated carcinoma
Gaucher's disease
Connective tissue abnormalities
Osteogenesis imperfecta
Homocystinuria
Ehlers-Danlos syndrome
Marfan's syndrome
Menke's syndrome
Miscellaneous causes
Immobilisation or weightlessness
Sudeck's atrophy
Chronic obstructive pulmonary disease
Chronic alcoholism
Chronic heparin administration
Chronic ingestion of anticonvulsant drugs In addition the invention encompasses the treatment of tumours, especially those related to renal cancer, melanoma, colon cancer, lung cancer and leukemia, viral conditions (for example those involving Semliki Forest virus, Vesicular Stomatitis virus, Newcastle Disease virus, Influenza A and B viruses, HIV virus), ulcers (for example chronic gastritis and peptic ulcer induced by Helicobacter pylori), for use as immunosuppressant agents in autoimmune diseases and transplantation, antilipidemic agents for the treatment and/or prevention of hypercholesterolemic and atherosclerotic diseases and to be useful for the treatment of AIDS and Alzheimer's disease. These compounds are also considered useful in treating angiogenic diseases, i.e. those pathological conditions which are dependent on angiogenesis, such as rheumatoid arthritis, diabetic retinopathy, psoriasis and solid tumours.

Accordingly, present invention provides a method for the treatment and/or prophylaxis of diseases associated with over activity of osteoclasts in mammals which method comprises the administration of an effective non-toxic amount of a compound of formula (I), or a pharmaceutically acceptable salt thereof, or a pharmaceutically acceptable solvate thereof.

In a further aspect, the present invention provides a method for the treatment or prophylaxis of osteoporosis and related osteopenic diseases in a human or non-human mammal, which method comprises administering an effective, non-toxic, amount of a compound of formula (I) or a pharmaceutically acceptable salt thereof or a pharmaceutically acceptable solvate thereof, to a human or non-human mammal in need thereof.

In a further aspect, the present invention provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by Helicobacter pylori), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal, which method comprises administering an effective, non-toxic, amount of a compound of formula (I) or a pharmaceutically acceptable salt thereof or a pharmaceutically acceptable solvate thereof, to a human or non-human mammal in need thereof.

In a still further aspect, the present invention a compound of formula (I) or a pharmaceutically acceptable salt thereof, or a pharmaceutically acceptable solvate thereof, for use as an active therapeutic substance.

In further aspect the present invention provides a compound of formula (I) or a pharmaceutically acceptable salt thereof or a pharmaceutically acceptable solvate thereof, for use in the treatment or prophylaxis of diseases associated with over activity of osteoclasts in mammals.

In further aspect the present invention provides a compound of formula (I) or a pharmaceutically acceptable salt thereof or a pharmaceutically acceptable solvate thereof, for use in the treatment or prophylaxis of osteoporosis and related osteopenic diseases.

In a further aspect, the present invention provides a compound of formula (I) or a pharmaceutically acceptable salt thereof or a pharmaceutically acceptable solvate thereof, for use in the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable salt thereof, or a pharmaceutically acceptable solvate thereof, and a pharmaceutically acceptable carrier therefor.

Active compounds or a pharmaceutically acceptable salt thereof and/or a pharmaceutically acceptable solvate thereof is normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated and the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily dose is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

Accordingly, in further aspect, the present invention provides a compound of formula (I) or a pharmaceutically acceptable salt thereof or a pharmaceutically acceptable solvate thereof, for use in the manufacture of a medicament for the treatment or prophylaxis of diseases associated with over activity of osteoclasts in mammals.

In further aspect the present invention also provides a compound of formula (I) or a pharmaceutically acceptable salt thereof or a pharmaceutically acceptable solvate thereof, for use in the manufacture of a medicament for the treatment or prophylaxis of osteoporosis and related osteopenic diseases.

In a further aspect, the present invention also provides the use of a compound of formula (I), or a pharmaceutically acceptable salt thereof, or a pharmaceutically acceptable solvate thereof, for the manufacture of a medicament for the treatment of tumours, especially those related to renal cancer, melanoma, colon cancer, lung cancer and leukemia., viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

EXAMPLES AND DESCRIPTIONS

Preparation 1. 2-Methoxy-4-cyanobenzaldehyde

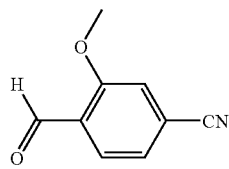

Thionyl chloride (50 ml) was added to 2-methoxy-4-cyano benzoic acid (*Tetrahedron Letters*, 1986, 27(49), 5997–6000) (8 g, 45.2 mmol) in dichloromethane (70 ml) and the solution was refluxed for 5 h. After cooling to room temperature, the solvent was removed under reduced pressure. The crude benzoyl chloride was dissolved in diglime (120 ml), cooled at −78° C. and 1M lithium tritertbutoxyaluminium hydride in THF (46 ml, 46 mmol) was added dropwise in 3 h. Stirring was continued for 30 min at −78° C. then the reaction was allowed to reach 0° C. and quenched with water (15 ml) and 2N NaOH (15 ml). The reaction mixture was stirred for 1 h, filtered and the organic phase was removed under reduced pressure. The crude residue was purified by column chromatography eluting with n-hexane/ethyl acetate 80:20 to give 4 g of the title compound (yield 55%) as a yellow powder, mp=112–114° C.

$^1$H-NMR (CDCl$_3$) δ=10.5 (s, 1H); 7.93 (d, 1H); 7.30 (d, 1H); 7.16 (s, 1H); 4.01 (s, 3H).

Preparation 2. 5,6-Dichloro-2-(4-cyano-2-methoxyphenyl)benzimidazole (A) and 5,6-dichloro-2-(4-cyano-2-hydroxyphenyl)benzimidazole (B)

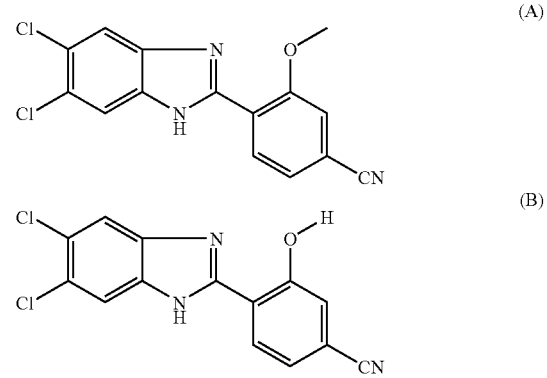

A mixture of 2-methoxy-4-cyanobenzaldehyde (3 g, 18.6 mmol), prepared as described in Preparation 1, with 4,5-dichlorophenylendiamine (3.2 g, 18.6 mmol) in nitrobenzene (20 ml) was heated at 160–165° C. for 20 h. After cooling to room temperature, n-hexane (300 ml) was added and the mixture was stirred 1 h at room temperature. The mixture was filtered and the solid was washed with additional n-hexane (50 ml). the organic phase was evaporated at reduced pressure to give 3.55 g of a mixture of 5,6-dichloro-2-(4-cyano-2-methoxyphenyl)benzimidazole and 5,6-dichloro-2-(4-cyano-2-hydroxyphenyl)benzimidazole as a brown powder.

Preparation 3. 5,6-Dichloro-2-(4-carboxy-2-methoxyphenyl)benzimidazole (A) and 5,6-dichloro-2-(4-carboxy-2-hydroxyphenyl)benzimidazole (B)

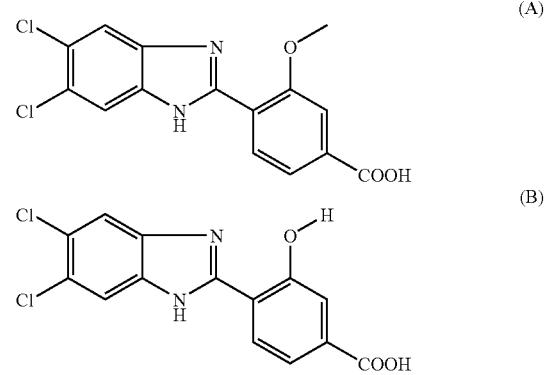

A mixture of 5,6-dichloro-2-(4-cyano-2-methoxyphenyl) benzimidazole and 5,6-dichloro-2-(4-cyano-2-hydroxyphenyl)benzimidazole (3.5 g), prepared as described in Preparation 2, in ethanol (70 ml) and 2N NaOH (30 ml) was refluxed for 4 h. Solvent was removed under reduced pressure and the residue was treated with 20% HCl (60 ml). The solid was filtered, washed with water (50 ml) and dried at 50° C. under vacuum to give 3.2 g of the title compounds.

Preparation 4. 2-Methoxy-4-cyanobenzoyl chloride

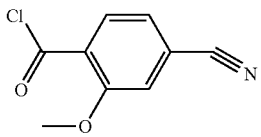

2-Methoxy-4-cyanobenzoic acid (*Tetrahedron Letters*, 1986, 27(49), 5997–6000) (1 g, 5.6 mmol) was dissolved in CH$_2$Cl$_2$ (20 ml). Oxalyl chloride (1.5 ml, 8.2 mmol) was rapidly introduced into the solution and a drop of DMF was added. A vigorous reaction took place with the abundant evolution of gaseous products. The solution was stirred for 1 h then allowed to stand over night. Solvent was removed using a rotary evaporator to leave 1.1 g of an off white solid (5.6 mmol, yield 99%) that was used without further purification.

Preparation 5. 5,6-Dichloro-2-(4-cyano-2-methoxyphenyl)benzimidazole

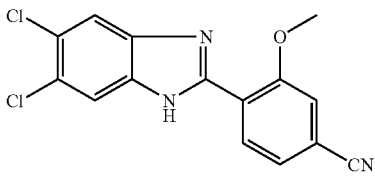

A solution of 2-methoxy-4-cyanobenzoyl chloride (2 g, 10 mmol) in dichloromethane (20 ml) was added dropwise in 1 h to a solution of 4,5-dichlorophenylendiamine (3.54 g, 20 mmol) and triethylamine (10.1 g=13.9 ml, 100 mmol) in dichloromethane (20 ml). Stirring was continued for additional two hours. The solvent was removed under vacuum and the residue was triturated with water (50 ml), filtered and dried at 50° C. under vacuum. The solid was suspended in diethyl ether (150 ml), stirred for 1 h, filtered and dried under vacuum to give 2.9 g of N-(2-amino-4,5-dichlorophenyl)-2-methoxy-4-cyanobenzamide (yield 43%), mp>250° C.

A suspension of N-(2-amino-4,5-dichlorophenyl)-2-methoxy-4-cyanobenzamide (2.9 g, 8.6 mmol) and P$_2$O$_5$ (2.9 g, 10 mmol) in xylene (48 ml) was refluxed for 24 h. Additional P$_2$O$_5$ (2.9 g, 10 mmol) was added and the mixture was refluxed for 42 h. Solvent was removed under reduced pressure. The residue was treated with 2N NaOH (50 ml) and extracted with ethyl acetate (100 ml). The organic layer was washed with water and brine, dried over Na$_2$SO$_4$, filtered and evaporated under reduced pressure to give 2 g of the title compound (yield 73%), mp>250° C.

Preparation 6. 5,6-Dichloro-2-(4-carboxy-2-methoxyphenyl)benzimidazole

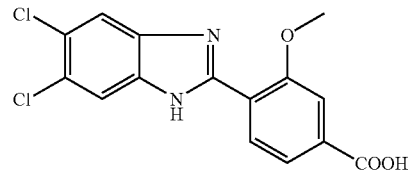

A solution of 5,6-dichloro-2-(4-cyano-2-methoxyphenyl)benzimidazole, prepared as described in Preparation 5, in ethanol (50 ml) and 2N NaOH (15 ml) was refluxed for 16 h. Solvent was removed under reduced pressure and the residue was acidified with 37% HCl (10 ml), stirred for 1 h. The solid was filtered, washed with water (50 ml), dried at 50° C. under vacuum to give 0.92 g of the title compound (yield 46%), mp>250° C.

Preparation 7. 5,6-Dichloro-2-(4-methoxycarbonylphenyl)benzimidazole

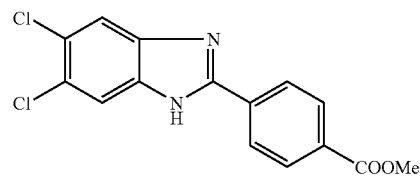

A mixture of 4,5-dichlorophenylendiamine (4 g, 22.6 mmol) and methyl 4-formylbenzoate (3.68, 22.6 mmol) in nitrobenzene (35 ml) was heated at 140° C. for 30 h. After cooling, the mixture was diluted with n-hexane (150 ml) and stirred for 1 h. The solid was filtered obtaining 5 g of the title compound (yield 68.9%) as a brown powder, mp=240–250° C.

Preparation 8. 5,6-Dichloro-2-(4-carboxyphenyl)benzimidazole

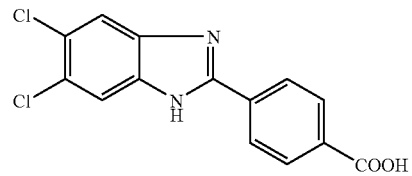

A mixture of 5,6-dichloro-2-(4-methoxycarbonylphenyl)benzimidazole (2.4 g, 7.47 mmol), prepared as described in Preparation 7, 20% NaOH (7.5 ml, 37.5 mmol) in THF (25 ml) was heated at 50° C. for 1 h. After cooling at room temperature, solvent was removed under reduced pressure and pH was adjusted to 5 with acetic acid. The solid that was precipitated was filtered and dried at 50° C. to give 2.1 g of the title compound (yield 91.8%) as a brown solid, mp>250° C.

Preparation 9. 2-Ethoxy-4-aminobenzoic acid

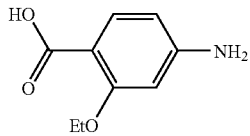

A suspension of methyl 2-ethoxy-4-acetamidobenzoate (50 g, 211 mmol) in aqueous solution of NaOH (15% W/W, 200 ml) was gently refluxed for 16 hours. The resulting pale brown solution was allowed to cool to room temperature and then further cooled in an ice water bath. Concentrated HCl (37% w/w) was added until the solution reached a pH of 6. The solid precipitated from the solution was filtered under vacuum, dried at 50° C. to give 38.3 g of the title compound (yield 100%).

Preparation 10. 2-Ethoxy-4-cyanobenzoic acid

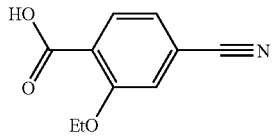

In a 1 l reactor equipped with a sealed mechanical stirrer, CuCN (12 g, 134 mmol) were suspended in 100 ml of distilled water. NaCN (18.3 g, 373 mmol) was added with vigorous stirring and the internal temperature was kept below 40° C. until all the CuCN went into solution. The suspension of 2-ethoxy-4-aminobenzoic acid (20 g, 110 mmol), prepared as in Preparation 9, in water (200 ml) and concentrated HCl (33 ml) was stirred and cooled in an ice bath. When the temperature reached 5° C., a solution of NaNO$_2$ (9.7 g, 140 mmol) in water (30 ml) was added dropwise at such a rate as to maintain the temperature below 5° C.

When all the NaNO$_2$ was added, the solution was slowly introduced through an ice cooled dropped funnel into the reactor containing the NaCN/CuCN solution. A reaction took place with the vigorous formation of N$_2$. A few drops of octanol were added to keep the foaming under control. Stirring was continued for 4 h. The resulting suspension was then extracted with ethyl acetate (3×100 ml) and the organic phase dried over MgSO$_4$ and evaporated under vacuum obtaining 15 g of the title compound (yield 71.1%) as a light brown powder, mp=70–172° C.

Preparation 11. 2-Ethoxy-4-cyanobenzoyl chloride

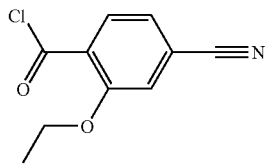

2-Ethoxy-4-cyanobenzoic acid (10 g, 52.3 mmol), prepared as in Preparation 10, and thionyl chloride (50 ml,) were refluxed in CH$_2$Cl$_2$ (80 ml) for 5 h. Solvent was removed under vacuum to leave 10.9 g of an off white solid (52 mmol, yield 99%) that was used without further purification.

Preparation 12. 5,6-Dichloro-2-(4-cyano-2-ethoxyphenyl)benzimidazole hydrochloride

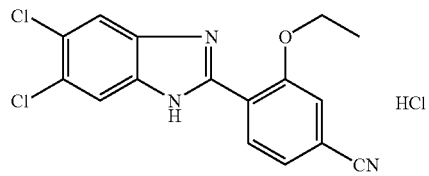

A solution of 2-ethoxy-4-cyanobenzoyl chloride (10.9 g, 52 mmol), prepared as in Preparation 11, in dichloromethane (109 ml) was added dropwise in 5 h to a solution of 4,5-dichlorophenylendiamine (18.5 g, 104.5 mmol) and triethylamine (53 g=72.6 ml, 523 mmol) in dichloromethane (550 ml). Stirring was continued for additional 2 h. The solvent was removed under vacuum and the residue was triturated with water (100 ml), filtered and dried at 50° C. under vacuum. The solid was suspended in diethyl ether (200 ml), stirred for 1 h, filtered and dried under vacuum to give 19 g of N-(2-amino-4,5-dichlorophenyl)-2-ethoxy-4-cyanobenzamide (yield 51%), mp=195–198° C.

A suspension of N-(2-amino-4,5-dichlorophenyl)-2-ethoxy-4-cyanobenzamide (19 g, 54.2 mmol) and P$_2$O$_5$ (19 g, 134 mmol) in xylene (380 ml) was refluxed for 24 h. Additional P$_2$O$_5$ (9.5 g, 67 mmol) was added and the mixture was refluxed for 48 h. Solvent was removed under reduced pressure. The residue was treated with 30% NaOH (80 ml) and water (100 ml) and then acidified with 37% HCl. The solid was filtered, washed with water and dried under vacuum at 50° C. to give 16.5 g of the title compound as a light brown powder (yield 82.6%), mp>250° C.

Preparation 13. 5,6-Dichloro-2-(4-carboxy-2-ethoxyphenyl)benzimidazole hydrochloride

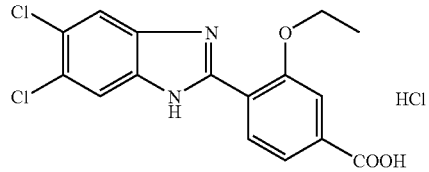

A mixture of 5,6-dichloro-2-(4-cyano-2-ethoxyphenyl)benzimidazole hydrochloride (16.3 g, 44.2 mmol), prepared as in Preparation 12, 32% NaOH (40 ml) in ethanol (100 ml) was refluxed for 8 h. After cooling to room temperature the organic solvent was removed under vacuum and the aqueous phase was acidified with 37% HCl, stirred for 1 h. The solid was filtered, washed with water (100 ml) and dried at 50° C. under vacuum to give 12 g of the title compound as a light brown powder (yield 70%), mp>250° C.

Example 1

4-(5,6-Dichlorobenzimidazol-2-yl)-N-(1,2,2,6,6-pentamethylpiperidin-4-yl)benzamide

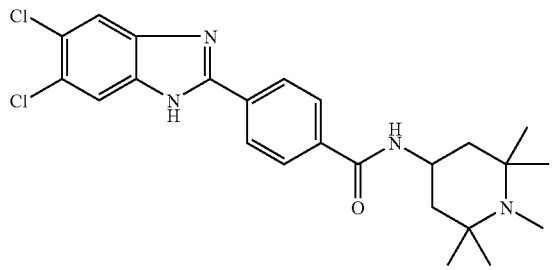

A mixture of 5,6-dichloro-2-(4-carboxyphenyl)benzimidazole (0.3 g, 0.9 mmol) prepared as described in Preparation 8, 1-hydroxybenzotriazole (0.145 g, 1.08 mmol) and N-(3-dimethylaminopropyl)-N'-ethylcarbodiimide hydrochloride (0.207 g, 1.08 mmol) in THF (10 ml) was heated at 35–40° C. for 1 h. 1,2,2,6,6,-Pentamethyl-4-aminopiperidine in THF (2 ml) was added dropwise and the reaction was refluxed for 1 h. After cooling to room temperature, the solvent was removed under reduced pressure and the residue was treated with 2N NaOH (5 ml). The solid was filtered, washed with water and dried at 50° C. under vacuum. The solid was suspended in isopropyl alcohol and stirred for half an hour, filtered and dried to give 91 mg of the title compound (yield 22%) as an yellow powder, mp>280° C.

$^1$H-NMR (DMSO-$d_6$) δ=13.95 (s br, 1H); 8.30 (d, 1H); 8.23 (d, 2H); 8.00 (d, 2H); 7.89 (s, 2H); 4.30–4.15 (m, 1H); 2.20 (s, 3H); 1.72 (dd, 2H); 1.49 (dd, 2H); 1.10 (s, 6H); 1.07 (s, 6H). ESI POS; TSQ 700; solvent: methanol/spray 4.5 kV/skimmer: 60 V/capillary 220° C.: 459 (MH$^+$). CID Offset=−36 V: 459; 429; 372; 289; 123; 72

Example 2

4-(5-Chlorobenzimidazol-2-yl)-N-(1,2,2,6,6-pentamethylpiperidin-4-yl)-benzamide

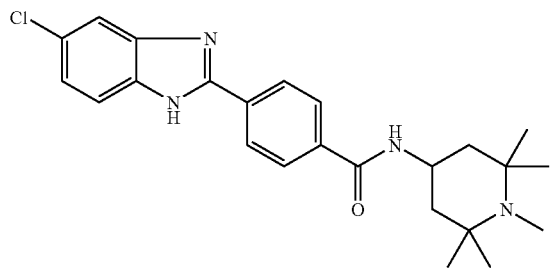

A mixture of 4-(5-chlorobenzimidazol-2-yl)benzoic acid (0.5 g, 1.63 mmol), 1-hydroxybenzotriazole (0.242 g, 1.79 mmol) and N-(3-dimethylaminopropyl)-N'-ethylcarbodiimide hydrochloride (0.34 g, 1.89 mmol) in THF (15 ml) was heated for 1 h at 35–40° C. 1,2,2,6,6-Pentamethyl-4-aminopiperidine (0.333 g, 1.96 mmol) in THF (3 ml) was added dropwise and the reaction was left 1 h at 60° C. After cooling, the solvent was removed under reduced pressure and the residue was treated with 2N NaOH (15 ml) and extracted with ethyl acetate (20 ml). the organic layer was washed with brine, dried over Na$_2$SO$_4$, filtered and evaporated under reduced pressure to give a residue that was treated with CH3CN. The suspension was stirred for 1 h, filtered and dried at 50° C. to give 0.35 g of the title compound (yield 50.5%) as a yellow solid, mp>250° C.

$^1$H-NMR (DMSO-$d_6$) δ=13.21 (s br, 1H); 8.29 (d, 1H); 8.23 (d, 2H); 8.01 (d, 2H); 7.67 (s br, 1H); 7.62 (d, 1H); 7.25 (dd, 1H); 4.20 (m, 1H); 2.20 (s, 3H); 1.72 (dd, 2H); 1.46 (dd, 2H); 1.10 (s, 2H); 1.06 (s, 6H). ESI POS; TSQ 700; solvent: methanol/spray 4.5 kV/skimmer: 60 V/capillary 220° C.: 425 (MH$^+$). ESI DAU+425–427 (Collision gas: Argon): 425; 394; 338; 272; 255; 123; 72.

Example 3

4-(5,6-Dichlorobenzimidazol-2-yl)-N-(1,2,2,6,6-pentamethylpiperidin-4-yl)-3-hydroxybenzamide

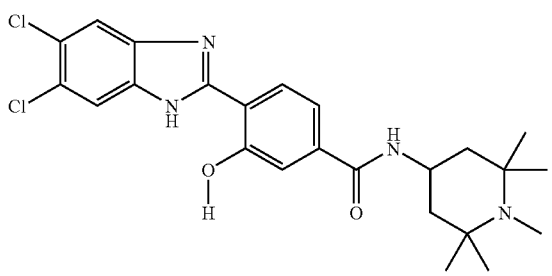

A solution of 5,6-dichloro-2-(4-carboxy-2-methoxyphenyl)benzimidazole and 5,6-dichloro-2-(4-carboxy-2-hydroxyphenyl)benzimidazole (0.5 g, 1.48 mmol), prepared as described in Preparation 3,1-hydroxybenzotriazole (0.21 g, 1.56 mmol) and N-(3-dimethylaminopropyl)-N'-ethylcarbodiimide hydrochloride (0.35 g, 1.82 mmol) in THF (20 ml) was refluxed for 5 h. A solution of 1,2,2,6,6-pentamethyl-4-aminopiperidine (0.25 g, 1.5 mmol) in THF (3 ml) was added dropwise and refluxed for 3 h. After cooling to room temperature the solvent was evaporated under vacuum and the crude residue was purified by column chromatography eluting with CH$_2$Cl$_2$/MeOH/NH$_4$OH 86:10:0.6 to give 10 mg of the title compound, mp>250° C.

$^1$H-NMR (DMSO-$d_6$) δ=12.39 (s br, 1H): 8.10 (d, 1H); 7.92 (d, 1H); 7.89 (s, 2H); 7.50 (s, 1H); 7.48 (d, 1H); 4.30–4.20 (m, 1H); 2.29 (s, 3H); 1.80 (dd, 2H); 1.52 (dd, 2H); 1.14 (s, 6H); 1.11 (s, 6H). ESI POS; TSQ 700; solvent: methanol/spray 4.5 kV/skimmer: 60 V/capillary 220° C.: 475 (MH$^+$). CID offset=−42V: 475; 444; 388; 305; 123; 72.

Example 4

4-(5,6-Dichlorobenzimidazol-2-yl)-N-(1,2,2,6,6-pentamethylpiperidin-4-yl)-3-methoxybenzamide

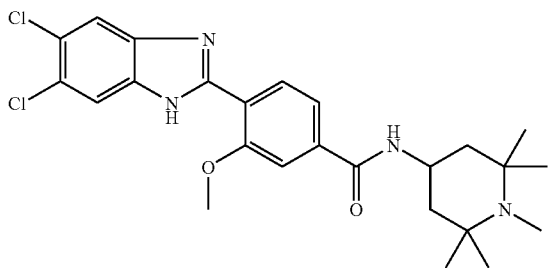

A solution of 5,6-dichloro-2-(4-carboxy-2-methoxyphenyl)benzimidazole (0.8 g, 2,36 mmol), prepared as described in Preparation 6,1-hydroxybenzotriazole (0.32 g, 2.36 mmol) and N-(3-dimethylaminopropyl)-N'-ethylcarbodiimide hydrochloride (0.56 g, 2.9 mmol) in 80 ml of DMF/THF (50:50) was refluxed for 5 h. A solution of 1,2,2,6,6-pentamethyl-4-aminopiperidine (0.5 g, 2.9 mmol) in THF (5 ml) was added dropwise and the reaction was refluxed for additional 3 h. After cooling, solvent was removed under reduced pressure and the residue was treated with 1N NaOH (10 ml) and extracted with dichloromethane (50 ml). The organic layer was washed with water, dried over $Na_2SO_4$, filtered and evaporated under reduced pressure. The residue was triturated with diisopropyl ether (150 ml), stirred for 1 h, filtered to give 0.55 g of the title compound (yield 47.6%), mp=285–286° C.

$^1$H-NMR (DMSO-$d_6$) δ=12.40 (s br, 1H); 8.37 (d, 1H); 8.32 (d, 1H); 7.88 (s br, 2H); 7.66 (d, 1H); 7.61 (dd, 1H); 4.22 (m, 1H); 4.10 (s, 3H); 2.19 (s, 3H); 1.73 (dd, 2H); 1.47 (dd, 2H); 1.10 (s, 6H); 1.05 (s, 6H). ESI POS; TSQ 700; solvent: methanol/spray 4.5 kV/skimmer: 60 V/capillary 220° C.: 489 (MH$^+$). CID Offset=−45V: 489; 319; 123.

Example 5

4-(5,6-Dichloro-1-methylbenzimidazol-2-yl)-N-(1,2,2,6,6-pentamethylpiperidin-4-yl)-3-methoxybenzamide

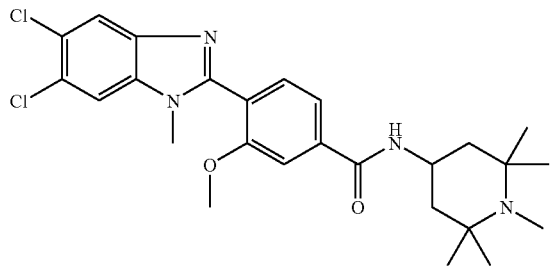

A mixture of 4-(5,6-dichlorobenzimidazol-2-yl)-N-(1,2,2,6,6-pentamethylpiperidin-4-yl)-3-methoxybenzamid (0.16 g, 0.33 mmol), prepared as described in Example 4, and KOH (0.0185 g, 0.33 mmol) in acetone (8 ml) was stirred for 1 h at room temperature. Iodomethane (0.047 g, 0.033 mmol) was added and stirring was continued for 24 h. Solvent was removed under reduced pressure and the residue was partitioned between water and ethyl acetate. the organic layer was washed with brine, dried over $Na_2SO_4$, filtered and evaporated under reduced pressure. The crude residue was purified by column chromatography eluting with $CH_2Cl_2$/MeOH/$NH_4OH$ 95:5:0.2. Fraction containing the desired product were collected, evaporated to dryness under reduced pressure and the solid was triturated with diisopropyl ether to give 0.022 g of the title compound (yield 13%), mp=178–180° C.

$^1$H-NMR (DMSO-$d_6$) δ=8.01 (d br, 1H); 7.91 (s, 1H); 7.89 (s, 1H); 7.64 (d, 1H); 7.61 (dd, 1H); 7.54 (d, 1H); 4.25 (m,1H); 3.90 (s, 3H); 3.61 (s, 3H); 2.24 (s, 3H); 1.81 (dd, 2H); 1.56 (dd, 1H); 1.15 (s, 6H); 1.09 (s, 6H). ESI POS; TSQ 700; solvent: methanol/spray 4.5 kV/skimmer: 60 V/capillary 220° C.: 503 (MH$^+$); 472; 416. CID Offset=−67 V: 503; 472; 416; 350; 333; 123; 72.

Example 6

4-(5,6-Dichlorobenzimidazol-2-yl)-N-(2,2,6,6-tetramethylpiperidin-4-yl)-3-ethoxybenzamide

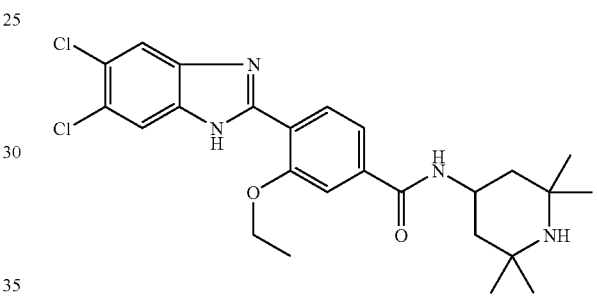

A mixture of 5,6-dichloro-2-(4-carboxy-2-ethoxyphenyl) benzimidazole hydrochloride (1 g, 2.58 mmol), prepared as in Preparation 11, thionyl chloride (8 ml) in dichloromethane (20 ml) was refluxed for 3 h. After cooling to room temperature the solvent was removed under vacuum and the crude residue was used in following reaction without further purification.

The acid chloride was added portionwise to a solution of 4-amino-2,2,6,6-tetramethylpiperidine (0.612 g, 3.87 mmol), triethylamine (5 ml, 36 mmol) in dichloromethane (50 ml). Stirring was continued at room temperature for 2 h. The solvent was removed under vacuum and the residue was suspended in water (50 ml) and filtered. The solid was dried at 50° C. under vacuum and then crystallised with ethanol to give 0.6 g of the title compound as a light brown powder (yield 47.5%), mp>280° C.

$^1$H-NMR (DMSO-$d_6$) δ=12.20 (s br, 1H); 8.30 (m, 2H); 7.90 (s, 2H); 7.64 (s, 1H); 7.59 (d, 1H); 4.40 (q, 2H); 4.35–4.22 (m, 1H); 1.73 (d, 2H); 1.50 (t, 3H); 1.20 (dd, 2H); 1.20 (s, 6H); 1.05 (s, 6H). EI; TSQ 700; source 180° C.; 70 V; 200 uA: 488 (MH$^+$); 473; 124.

The compounds listed in Table 1 were prepared according to Example 6.

TABLE 1

| Ex. No | Name | X | Y | Z | R₁ | R₂ | R₃ | R₄ | Rₛ | Rₜ | MP(° C.) | N.M.R. | MS |
|---|---|---|---|---|---|---|---|---|---|---|---|---|---|
| 7 | 4-(5,6-Dichlorobenzimidazol-2-yl)-N-[3-[4-(2-pyrimidinyl)piperazin-1-yl]propyl]-3-methoxybenzamide | NH | CH | CH | 5-Cl | 6-Cl | OMe | H | ![propyl-piperazinyl-pyrimidine group] | H | 255–258 | $^1$H-NMR(DMSO-$d_6$) δ = 10.90(s br, 1H); 8.96(t, 1H); 8.45(d, 2H); 8.39(d, 1H); 7.91(s, 2H); 7.72(s, 1H); 7.62(d, 1H); 6.71(dd, 1H); 4.71(d, 2H); 4.12(s, 3H); 3.60(d, 2H); 3.50–3.35 (m, 4H); 3.21–3.00(m, 4H); 2.05(m, 2H). | A) ESI POS; solvent; methanol/ spray 4.5 kV/ skimmer: 60 V/ capillary 220° C.: 540(MH⁺). B) CID Offset = −53 V: 540; 376; 319; 122. |
| 8 | 4-(5,6-Dichlorobenzimidazol-2-yl)-N-[3-[4-(2-pyrimidinyl)piperazin-1-yl]propyl]-3-hydroxybenzamide | NH | CH | CH | 5-Cl | 6-Cl | OH | H | ![propyl-piperazinyl-pyrimidine group] | H | 258–260 | $^1$H-NMR(DMSO-$d_6$) δ = 13.00(s br, 1H); 8.57(t, 1H); 8.35(d, 2H); 8.18(d, 1H); 7.93(s br, 2H); 7.52 (s, 1H); 7.49(d, 1H); 6.61 (dd, 1H); 3.71(m, 4H); 3.40–3.28(m, 2H); 2.49–2.39(m, 6H); 1.80–1.70(m, 2H). | ESI POS; TSQ 700; solvent; methanol/ spray 4.5 kV/ skimmer 60 V/ capillary 220° C.: 526(MH⁺) |
| 9 | 4-(5,6-Dichlorobenzimidazol-2-yl)-N,N-dimethyl-3-methoxybenzamide | NH | CH | CH | 5-Cl | 6-Cl | OMe | H | Me | Me | 254–256 | $^1$H-NMR(DMSO-$d_6$)δ = 12.38(s br, 1H); 8.38(d, 1H); 7.92(s br, 1H); 7.80(s br, 1H); 7.30(s, 1H); 7.15 (d, 1H); 4.09(s, 3H); 3.05 (s, 3H); 3.00(s, 3H). | EI; TSQ 700; 400 mA; 70 V: 363(M⁺); 334; 319; 291; 213; 187. |

TABLE 1-continued

| Ex. No | Name | X | Y | Z | R₁ | R₂ | R₃ | R₄ | Rs | Rt | MP(° C.) | N.M.R. | MS |
|---|---|---|---|---|---|---|---|---|---|---|---|---|---|
| 10 | 4-(5,6-Dichlorobenzimidazol-2-yl)-N-(2,2,6,6-tetramethylpiperidin-4-yl)-3-methoxybenzamide | NH | CH | CH | 5-Cl | 6-Cl | OMe | H | (2,2,6,6-tetramethylpiperidin-4-yl) | H | 233–235 | ¹H-NMR(DMSO-d₆) δ = 12.40(s br, 1H); 8.36(d, 1H); 8.31(d, 1H); 7.93(s br, 1H); 7.81(s br, 1H); 7.66(d, 1H); 7.61(dd, 1H); 4.40–4.30(m, 1H); 4.10(s, 3H); 1.73(dd, 2H); 1.21 (dd, 2H); 1.20(s, 6H); 1.08 (s, 6H). | EI; TSQ 700; 400 mA; 70 V: 474(M⁺); 459; 124. |
| 11 | 4-(5,6-Dichlorobenzimidazol-2-yl)-N-(2,2,6,6-tetramethylpiperidin-4-yl)-N-methyl-3-methoxybenzamide | NH | CH | CH | 5-Cl | 6-Cl | OMe | H | (2,2,6,6-tetramethylpiperidin-4-yl) | Me | 240–242 | ¹H-NMR(DMSO-d₆) δ(343 K) = 12.23(s br, 1H); 8.34 (d, 1H); 7.84(s br, 2H); 7.21 (s, 1H); 7.08(dd, 1H); 4.17–3.91(m, 1H); 4.06(s, 3H); 2.84(s, 3H); 1.54(dd, 2H); 1.42(dd, 2H); 1.05(s, 12H). | EI; TSQ 700; source 180° C.; 70 V; 200 mA: 473; 124. |
| 12 | 4-(5,6-Dichlorabenzimidazol-2-yl)-N-(1,2,2,6,6-pentamethylpiperidin-4-yl)-3-ethoxybenzamide | NH | CH | CH | 5-Cl | 6-Cl | OEt | H | (1,2,2,6,6-pentamethylpiperidin-4-yl) | H | >260 | ¹H-NMR(DMSO-d₆) δ: 12.19(s br, 1H); 8.31(d br, 1H); 8.28(d, 1H); 7.93(s, 1H); 7.85(s, 1H); 7.64(s, 1H); 7.59(d, 1H); 4.41(q, 2H); 4.30–4.13(m, 1H); 2.20(s, 3H); 1.73(dd, 2H); 1.48(t, 3H); 1.47(dd, 2H); 1.11(s, 6H); 1.06(s, 6H). | EI; TSQ 700; source 180° C.; 70 V; 200 mA; 487; 139 |
| 13 | 4-(5,6-Dichlorobenzimidazol-2-yl)-N-(2,2,6,6-tetramethylpiperidin-4-yl)-3-methylbenzamide | NH | CH | CH | 5-Cl | 6-Cl | Me | H | (2,2,6,6-tetramethylpiperidin-4-yl) | H | >250 | ¹H-NMR(DMSO-d₆) δ = 13.05(s br, 1H); 8.30(m, 1H); 8.00–7.80(m, 5H); 4.35–4.25(m, 1H); 2.68(s, 3H); 1.79(d, 2H); 1.24(s, 12H); 1.12(m, 2H). | EI; TSQ 700; 400 mA; 70 V: 458(M⁺); 443; 124. |

TABLE 1-continued

| Ex. No | Name | X | Y | Z | R₁ | R₂ | R₃ | R₄ | R₅ | Rt | MP(° C.) | N.M.R. | MS |
|---|---|---|---|---|---|---|---|---|---|---|---|---|---|
| 14 | 4-(5,6-Dichlorobenzimidazol-2-yl)-N-[5-(2-methoxy)pyridyl]-3-ethoxybenzamide | NH | CH | CH | 5-Cl | 6-Cl | OEt | H | (6-methoxypyridin-3-yl) | H | 219–220 | ¹H-NMR(DMSO-d₆) δ: 12.25(s, 1H); 10.39(s, 1H); 8.53(d, 1H); 8.37(d, 1H); 8.05(dd, 1H); 7.96(s, 1H); 7.87(s, 1H); 7.76(s, 1H); 7.73(d, 1H); 6.87(d, 1H); 4.47(q, 2H); 3.86(s, 3H); 1.50(t, 3H). | EI; TSQ 700; source 180° C.; 70 V; 200 mA: 456(M⁺); 441; 333. |
| 15 | 4-(5,6-Dichlorobenzimidazol-2-yl)-N-(3-pyridyl)-3-ethoxybenzamide | NH | CH | CH | 5-Cl | 6-Cl | OEt | H | (pyridin-3-yl) | H | >260 | ¹H-NMR(DMSO-d₆) δ: 12.26(s, 1H); 10.54(s, 1H); 8.94(s, 1H); 8.38(d, 1H); 8.34(d, 1H); 8.20(d, 1H); 7.96(s, 1H); 7.87(s, 1H); 7.77(s, 1H); 7.74(d, 1H); 7.42(dd, 1H); 4.47(q, 2H); 1.50(t, 3H). | EI; TSQ 700; source 180° C.; 70 V; 200 mA: 426(M⁺); 411; 333. |
| 16 | 4-(5,6-Dichlorobenzimidazol-2-yl)-N-(3-hydroxypropyl)-3-ethoxybenzamide | NH | CH | CH | 5-Cl | 6-Cl | OEt | H | (3-hydroxypropyl) | H | 148–150 | ¹H-NMR(DMSO-d₆) δ: 12.19(s br, 1H); 8.59(t br, 1H); 8.29(d, 1H); 7.94(s, 1H); 7.85(s, 1H); 7.65(s, 1H); 7.58(d, 1H); 4.47(t, 1H); 4.42(q, 2H); 3.48(dt, 2H); 3.35(dt, 2H); 1.71(m, 2H); 1.48(t, 3H). | EI; TSQ 700; source 180° C.; 70 V; 200 mA: 407(M⁺); 392; 289; 187. |
| 17 | 4-(5,6-Dichlorobenzimidazol-2-yl)-N-(1,2,2,6,6-pentamethylpiperidin-4-yl)-2,5-dimethoxybenzamide | NH | CH | CH | 5-Cl | 6-Cl | OMe | OMe | (1,2,2,6,6-pentamethylpiperidin-4-yl) | H | >250 | ¹H-NMR(DMSO-d₆) δ: 12.38(s br, 1H); 8.03–7.94 (m, 3H); 7.82(s, 1H); 7.53 (s, 1H); 4.30–4.10(m, 1H); 4.02(s, 3H); 3.94(s, 3H); 2.20(s, 3H); 1.76(dd, 2H); 1.41(dd, 2H); 1.11(s, 6H); 1.06(s, 6H). | EI; TSQ 700; source 180° C.; 70 V; 200 mA: 503; 349; 138; 124. |

TABLE 1-continued

| Ex. No | Name | X | Y | Z | R1 | R2 | R3 | R4 | Rs | Rt | MP(° C.) | N.M.R. | MS |
|---|---|---|---|---|---|---|---|---|---|---|---|---|---|
| 18 | 4-(5,6-Dichlorobenzimidazol-2-yl)-N-(2,2,6,6-tetramethylpiperidin-4-yl)-2,5-dimethoxybenzamide | NH | CH | CH | 5-Cl | 6-Cl | OMe | OMe | 2,2,6,6-tetramethylpiperidin-4-yl | H | >250 | $^1$H-NMR(DMSO-d$_6$) δ: 12.38(s br, 1H); 8.03(d, 1H); 7.99(s, 1H); 7.97(s br, 1H); 7.82(s br, 1H); 7.53 (s, 1H); 4.37–4.21(m, 1H); 4.03(s, 3H); 3.94(s, 3H); 1.78(s, 3H); 1.76(dd, 2H); 1.21(s, 6H); 1.17(dd, 2H); 1.08(s, 6H). | EI; TSQ 700; source 180° C.; 70 V; 200 mA; 489, 124. |
| 19 | 4-(5-Chlorobenzimidazol-2-yl)-N-(2,2,6,6-tetramethylpiperidin-4-yl)-3-ethoxybenzamide | NH | CH | CH | 5-Cl | H | OEt | H | 2,2,6,6-tetramethylpiperidin-4-yl | H | 222–225 | $^1$H-NMR(DMSO-d$_6$) δ: 12.18 and 12.10(s br, 1H); 8.49(d br, 1H); 8.30(d, 1H); 7.72–7.58(m, 4H); 7.23(m, 1H); 4.42(q, 2H); 4.44–4.29(m, 1H); 1.87(dd, 2H); 1.48(t, 3H); 1.48(dd, 2H); 1.36(s, 6H); 1.31(s br, 6H). | ESI POS; AQA; solvent: methanol/spray 3 kV/skimmer 20 V/probe 135° C.: 455(MH$^+$). |
| 20 | 4-(5,6-Diclorobenzimidazol-2-yl)-N-(4-hyroxycyclohex-1-yl)-3-ethoxybenzamide | NH | CH | CH | 5-Cl | 6-Cl | OEt | H | 4-hydroxycyclohex-1-yl | H | >260 | $^1$H-NMR(DMSO-d$_6$) δ: 12.18(s, 1H); 8.28(d br, 1H); 7.94(s, 1H); 7.85(s, 1H); 7.62(d, 1H); 7.58(dd, 1H); 4.53(d, 1H); 4.42(q, 2H); 3.82–3.68 (m, 1H); 3.47–3.35(m, 1H); 1.92–1.79(m, 4H); 1.48(t, 3H); 1.44–1.20(m, 4H). | A) EI: TSQ 700; source 180° C.; 70 V; 200 mA: 447 (M$^+$); 432, 350; 334; 305; 289. B) ESI POS; AQA; solvent: methanol/spray 3 kV/skimmer 20 V/probe 135° C.: 448(MH$^+$). |

TABLE 1-continued

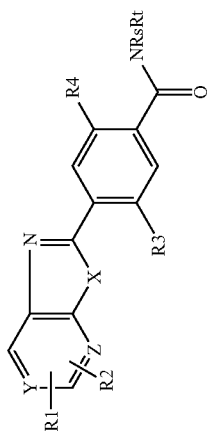

| Ex. No | Name | X | Y | Z | R₁ | R₂ | R₃ | R₄ | Rs | MP(° C.) | N.M.R. | MS |
|---|---|---|---|---|---|---|---|---|---|---|---|---|
| 21 | 4-(5,6-Dichlorobenzimidazol-2-yl)-N-(2,2,6,6-tetramethylpiperidin-4-yl)-3-isopropylbenzamide trifluoroacetate | NH | CH | CH | 5-Cl | 6-Cl | OiPr | H | | >250 | ¹H-NMR(DMSO-d₆) δ: 11.93(s br, 1H); 8.30(d br, 1H); 8.27(d, 1H); 7.93(s, 2H); 7.65(s, 1H); 7.59(dd, 2H); 4.23(m, 1H); 1.74(dd, 2H); 1.45(d, 6H); 1.20(dd, 2H); 1.20(s, 6H); 1.08(s, 6H). | A) EI; TSQ 700; source 180° C.; 70 V; 200 mA: 487; 124. |
| 22 | 4-(5,6-Dichlorobenzimidazol-2-yl)-N-(1-(4-(3-iodobenzoyl)benzylpiperidyn-4-yl)-3-ethoxybenzamide | NH | CH | CH | 5-Cl | 6-Cl | OEt | H | | 122 | ¹H-NMR(CDCl₃) δ: 10.75 s br, 1H); 8.6(d, 1H); 8.15(s, 1H); 7.95(m, 2H); 7.75(m, 3H); 7.68(m, 2H); 7.5(d, 2H); 7.35(d, 1H); 7.25(d, 1H); 6.11(d br, 1H); 4.45 (q, 2H); 4.13–4.00(m, 1H); 3.65(s, 2H); 2.95(d, 2H); 2.3(dd, 2H); 2.1(d, 2H); 1.76(m, 2H); 1.65(t, 3H). | |

Example 23
Solid Phase Synthesis of Benzimidazole Derivatives
Step 1 Addition of $R_s$
Resin (1) (1.0 g, 1.62 mmol) was suspended in 1% acetic acid in DMF (25 ml) along with 4-Amino-2,2,6,6-tetramethylpiperidine (2) (5 eq, 1.27 g). Sodium triacetoxyborohydride (5 eq, 1.72 g) was then added portionwise and the
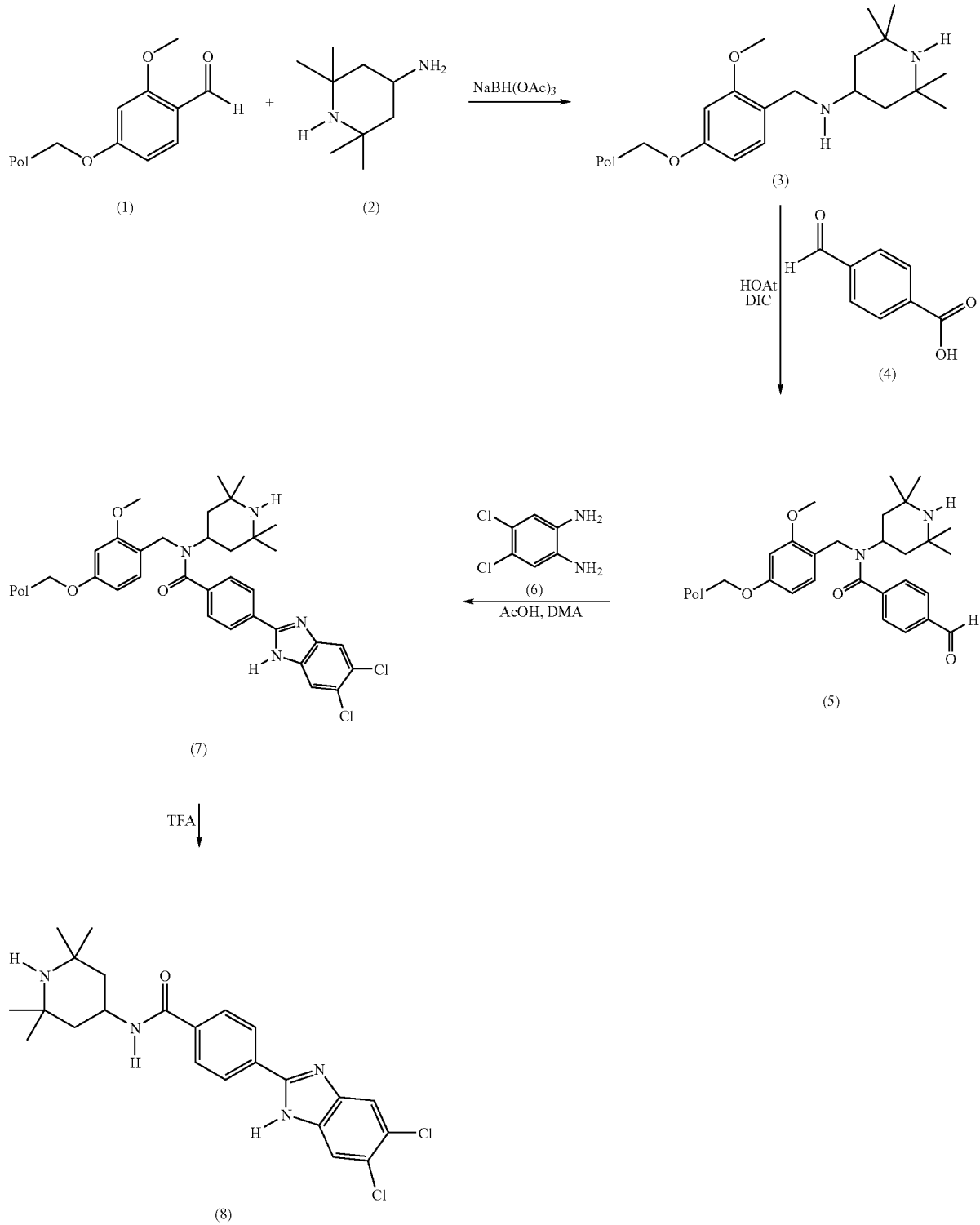

suspension mixed on a rotator for 20 h. The resulting suspension was then filtered and the resin was washed with DMF (×2), DCM (×2) and methanol (×2) (20 ml each wash). The resulting pale yellow resin (1.2 g) was analysed by MAS NMR (CDCl₃); δ=10.3 ppm disappears to indicate complete conversion to (3).

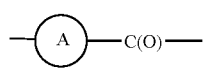

Step 2 Addition of the Moiety

Resin (3) (500 mg, 0.66 mmol) was suspended in DCM:DMF, 1:1 (10 ml) along with 1-Hydroxy-7-azabenzotriazole (1.1 eq, 99 mg), 4-Carboxybenzaldehyde (4) (1.1 eq, 110 mg) and 1,3-diisopropylcarbodiimide (1.1 eq, 114 ul). The suspension was mixed on a rotator for 22 h.

The resin was then filtered and washed with DMF (×2), DCM (×2) and methanol (×2) (20 ml each wash). The dried resin was analysed by MAS NMR (CDCl₃); appearance of aldehyde and aromatic signals at δ=10.3 ppm and δ=8.4–7.6 ppm indicate conversion to (5).

Step 3 Formation of Fused Heterocyclic Moiety

Resin (5) (280 mg, 0.31 mmol) was suspended in 5% acetic acid in DMA (6 ml) along with 4,5-Dichloro-1,2-diamine (6). The suspension was then warmed to 120° C. with stirring and heated for ~64 h.

The resin was then filtered and washed with DMA (×2), DMF (×2), DCM (×2), DMA (×3) and methanol (×2) (~15 ml each wash).

Step 4 Cleavage

The resin (7) was suspended in TFA:DCM:water 16:3:1 (7 ml) and mixed for ~1 h. The cleavage solution was then filtered and DCM (2×3 ml) used to rinse the resin. The combined filtrates were concentrated to give the benzimidazole (8) (47 mg) in 84% purity by HPLC (UV at 215 nm).

Purification by HPLC gave an orange/white solid which was pure benzimidazole (8)

¹H-NMR (CDCl₃) δ: 7.9–8.8 (aromatic and N—H protons, 9H); 4.4 (methine proton, 1H); 1.6 and 2.0 (methylene protons, 4H); 1.44 (methyl protons 12H).

MS (M+H)⁺ m/z 445.

Preparation 14. Array synthesis

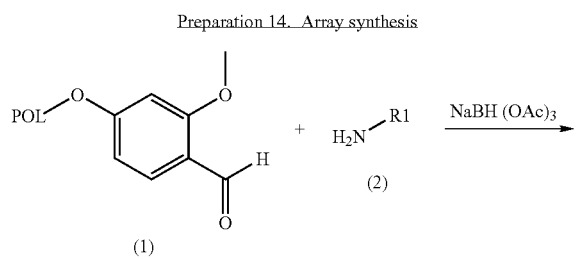

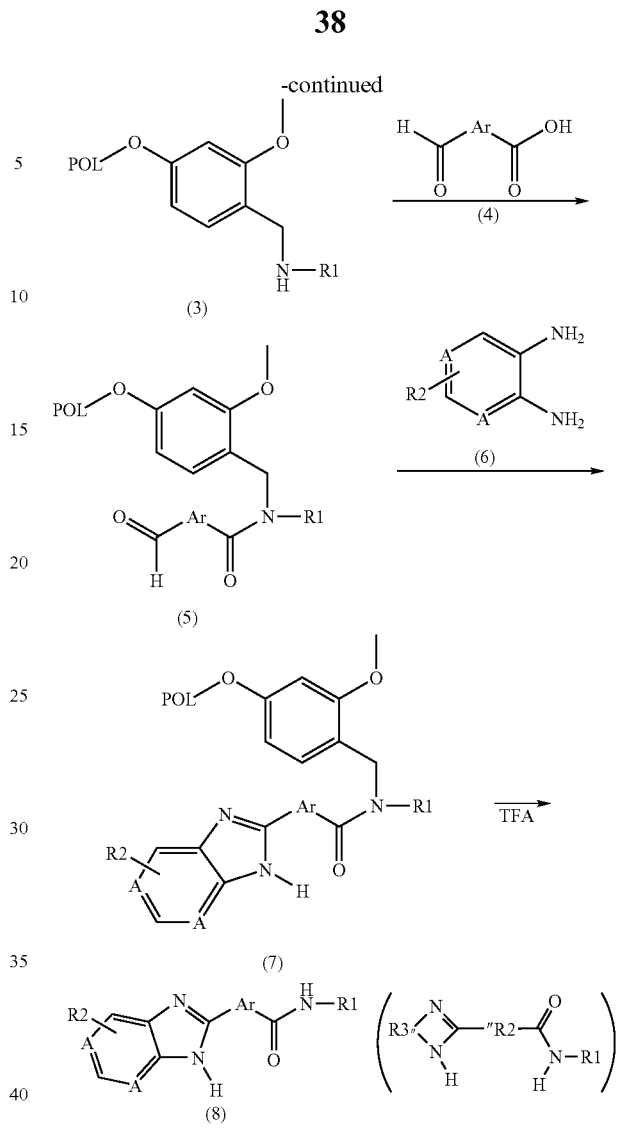

Step 1 Resin Attachment

Merrifield resin (250–300 um, 100 g, 0.2 mol) was suspended in dimethylacetamide (DMA, 1 l) along with 4-Hydroxy-2-methoxybenzaldehyde (2 eq, 60.8 g) and mixed with an overhead stirrer. Sodium hydride (60%, 2 eq, 16.0 g) was slowly added and the resulting brown suspension was heated at 80° C. for 18 h.

After cooling the resin was filtered and washed with DMF (×2), DCM:methanol 1:1 (×2), water (×1), methanol (×1), DCM (×1) and methanol (×3)(500 ml each wash). Drying in a vacuum oven gave the aldehyde (1) as a sand-coloured resin (121 g). Structure confirmed by MAS NMR, δ=10.3 ppm (aldehyde proton) and 67 =3.8 ppm (methoxy protons).

Step 2 Addition of R_s 12 batches of resin (1) (4 g, 6.48 mmol) were each suspended in 1% acetic acid in DMF (100 ml) along with the relevant amine (2) (5 eq, 32.4 mmol). Sodium triacetoxyborohydride (5 eq, 6.9 g) was then added gradually to each flask and the suspensions mixed on an orbital shaker for >19 h.

The resulting suspensions were filtered and each resin was washed with water (×1), DMF (×2), DCM (×2) and methanol (×2)(75 ml each wash). The resulting resins were analysed by MAS NMR; δ=10.3 ppm disappears to indicate complete conversion to (3).

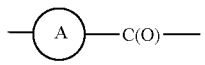

Step 3 Addition of Moiety

Each of the 12 amine-loaded resins (3) was added to 96 IRORI Microkans equipped with RF-tags (~42 mmol/kan) and these were sorted into 8 batches of 144 kans. Each batch was then suspended in DCM:DMF, 1:1 (120 ml) along with 1-Hydroxy-7-azabenzotriazole (5 eq, 4.0 g), the relevant carboxyaldehyde (4)(5 eq) and 1,3-Diisopropylcarbodiimide (5 eq, 4.7 ml). The suspensions were mixed on an orbital shaker for 22 h.

Step 4 Formation of Fused Heterocyclic Moiety

Each batch of 96 kans was suspended in 5% acetic acid in dioxane (~100 ml) along with the relevant 1,2-diamine (6). The suspensions were then warmed to 80° C. with stirring and heated for ~7 h.

The kans were then filtered and washed with NMP (×2), DCM:DMF 1:1 (×2), methanol (×1), DMA (×2), DCM:DMF 1:1 (×2), DCM (×1), methanol (×2) and ether (×2) (~500 ml each wash). The dried kans were resorted into 8×12 format ready for cleavage.

Step 5 Cleavage

The kans were arranged in cleavage blocks and each was suspended in TFA:DCM:water 16:3:1 (2 ml) and mixed on an orbital shaker for ~1 h. The cleavage solutions were then filtered into vials and DCM (1 ml) used to rinse the resin. The combined filtrates were concentrated on a vacuum centrifuge and the desired products isolated by purification using the Parallex HPLC system.

| $R_5$ Reagents | Mol. form. | Mol. Wt. | Equivs | Qty (g) |
|---|---|---|---|---|
| 4-AMINO-2,2,6,6-TETRAMETHYLPIPERIDINE | $C_9H_{20}N_2$ | 156.3 | 5 | 5.063 |
| 3-DIETHYLAMINOPROPYLAMINE | $C_7H_{18}N_2$ | 130.2 | 5 | 4.220 |
| N,N-DIETHYLETHYLENEDIAMINE | $C_6H_{16}N_2$ | 116.2 | 5 | 3.765 |
| 3-AMINOQUINUCLIDINE | $C_7H_{14}N_2$ | 199.1 | 5 | 6.452 |
| N-(3-AMINOPROPYL)MORPHOLINE | $C_7H_{16}N_2O$ | 144.2 | 5 | 4.673 |
| 4-AMINO-1-BENZYLPIPERIDINE | $C_{12}H_{18}N_2$ | 190.3 | 5 | 6.165 |
| 1-BOC-4-AMINOPIPERIDINE | $C_5H_{12}N_2$ | 200.3 | 5 | 6.489 |
| 3-[4-(3-CHLOROPHENYL)PIPERAZINYL]PROPYLAMINE | $C_{13}H_{20}ClN_3$ | 253.8 | 5 | 8.222 |
| 3-[4-(3-CHLORO-6-METHOXYPHENYL)PIPERAZINYL]PROPYLAMINE | $C_{14}H_{22}ClN_3O$ | 283.8 | 5 | 9.195 |
| MONO-N-(BOC)-PROPYLENEDIAMINE | $C_3H_{10}N_2$ | 174.2 | 5 | 5.645 |
| 3-(AMINOMETHYL)PYRIDINE | $C_6H_8N_2$ | 108.14 | 5 | 3.5 |

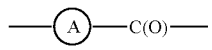

| Reagents | Mol. form. | Mol. Wt. | Equivs | Qty (g) |
|---|---|---|---|---|
| 4-CARBOXYBENZALDEHYDE | $C_8H_6O_3$ | 150.1 | 5 | 4.50 |
| 2-METHOXY-4-CARBOXYBENZALDEHYDE | $C_9H_8O_4$ | 180.2 | 5 | 5.40 |
| 2-ETHOXY-4-CARBOXYBENZALDEHYDE | $C_{10}H_{10}O_4$ | 194.2 | 5 | 5.82 |
| 2-METHYL-4-CARBOXYBENZALDEHYDE | $C_9H_8O_3$ | 164.2 | 5 | 4.92 |
| 2-FLUORO-4-CARBOXYBENZALDEHYDE | $C_8H_5FO_3$ | 168.1 | 5 | 5.04 |
| 2-BROMO-4-CARBOXYBENZALDEHYDE | $C_8H_5BrO_3$ | 229.0 | 5 | 6.86 |
| 5-FORMYL-2-THIOPHENECARBOXYLIC ACID | $C_6H_4O_3S$ | 156.2 | 5 | 4.68 |

| Fused heterocycle Reagents | Mol. form. | Mol. Wt. | Equivs | Qty (g) |
|---|---|---|---|---|
| *4-METHOXY-1,2-PHENYLENEDIAMINE | $C_7H_9N_2O$ | 139.2 | 10 | 5.31 |
| *5-BROMO-3,4-DIMETHYL-1,2-PHENYLENEDIAMINE | $C_8H_{10}BrN_2$ | 216.1 | 10 | 8.26 |
| *5-CHLORO-4-METHYL-1,2-PHENYLENEDIAMINE | $C_7H8ClN_2$ | 157.6 | 10 | 6.01 |
| *3-METHYL-1,2-PHENYLENEDIAMINE | $C_7H_9N_2$ | 123.2 | 10 | 4.69 |
| *4,5-DICHLORO-1,2-PHENYLENEDIAMINE | $C_6H_5Cl_2N_2$ | 178.0 | 10 | 6.80 |
| *4-FLUORO-5-CHLORO-1,2-PHENYLENEDIAMINE | $C_6H5ClFN_2$ | 161.6 | 10 | 6.17 |
| *3-CHLORO-5-TRIFLUOROMETHYL-1,2-PHENYLENEDIAMINE | $C_7H_5ClF3N_2$ | 211.6 | 10 | 8.09 |
| *2,3-DIAMINONAPHTHALENE | $C_{10}H_9N_2$ | 159.2 | 10 | 6.08 |
| *4-TRIFLUOROMETHYL-1,2-PHENYLENEDIAMINE | $C_7H6F_3N_2$ | 177.1 | 10 | 6.76 |
| *3-HYDROXY-1,2-PHENYLENEDIAMINE | $C_6H7N_2O$ | 125.1 | 10 | 4.77 |
| *3,4-DIAMINOPYRIDINE | $C_5H_6N_3$ | 110.1 | 10 | 4.19 |
| *4,5-DIAMINOPYRIMIDINE | $C_4H_5N_4$ | 111.1 | 10 | 4.23 |

The kans were then filtered and washed with DCM (×1), DMF (×2), methanol (×1), DCM (×2), DCM:methanol 1:1 (×1), methanol (×2) and ether (×2)(~500 ml each wash). The dried kans were resorted into 12 batches for the next step.

The compounds listed in Table 2 were prepared following the procedure described in Example 23, following Preparation 14. All of the library compounds gave the expected [M+H]+ pseudomolecular ion signal by mass spectrometry.

TABLE 2

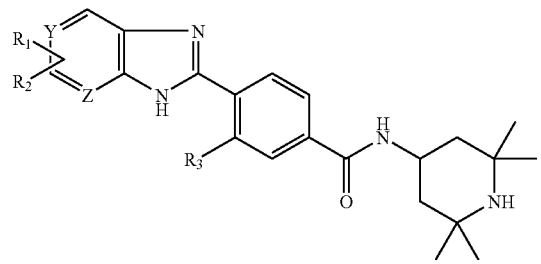

| Ex. No | Name | R₁ | R₂ | Y | Z | R₃ |
|---|---|---|---|---|---|---|
| 23 | 4-(5,6-Dichlorobenzimidazol-2-yl)-N-(2,2,6,6-tetramethylpiperidin-4-yl)benzamide | 5-Cl | 6-Cl | CH | CH | H |
| 24 | 4-(6-Methoxybenzimidazol-2-yl)-N-(2,2,6,6-tetramethylpiperidin-4-yl)benzamide | 6-OMe | H | CH | CH | H |
| 25 | 4-(5-Bromo-6,7-dimethylbenzimidazol-2-yl)-N-(2,2,6,6-tetramethylpiperidin-4-yl)benzamide | 5-Br | 6-Me | CH | C(Me) | H |
| 26 | 4-(5-Chloro-6-methylbenzimidazol-2-yl)-N-(2,2,6,6-tetramethylpiperidin-4-yl)benzamide | 5-Cl | 6-Me | CH | CH | H |
| 27 | 4-(4-Methylbenzimidazol-2-yl)-N-(2,2,6,6-tetramethylpiperidin-4-yl)benzamide | 4-Me | H | CH | CH | H |
| 28 | 4-(7-Hydroxybenzimidazol-2-yl)-N-(2,2,6,6-tetramethylpiperidin-4-yl)benzamide | 7-OH | H | CH | CH | H |
| 29 | 4-(5-Chloro-6-fluorobenzimidazol-2-yl)-N-(2,2,6,6-tetramethylpiperidin-4-yl)benzamide | 5-Cl | 6-F | CH | CH | H |
| 30 | 4-(4-Chloro-6-trifluoromethylbenzimidazol-2-yl)-N-(2,2,6,6-tetramethylpiperidin-4-yl)benzamide | 4-Cl | 6-CF₃ | CH | CH | H |
| 31 | 4-(1H-Naphth[2,3-d]imidazol-2-yl)-N-(2,2,6,6-tetramethylpiperidin-4-yl)benzamide | 5,6(—CH=CH—CH=CH—) | | CH | CH | H |
| 32 | 4-(6-Trifluoromethylbenzimidazol-2-yl)-N-(2,2,6,6-tetramethylpiperidin-4-yl)benzamide | 6-CF₃ | H | CH | CH | H |
| 33 | 4-(6-Methoxybenzimidazol-2-yl)-N-(2,2,6,6-tetramethylpiperidin-4-yl)-3-methoxybenzamide | 6-OMe | H | CH | CH | OMe |
| 34 | 4-(5-Bromo-6,7-dimethylbenzimidazol-2-yl)-N-(2,2,6,6-tetramethylpiperidin-4-yl)-3-methoxybenzamide | 5-Br | 6-Me | CH | C(Me) | OMe |
| 35 | 4-(5-Chloro-6-methylbenzimidazol-2-yl)-N-(2,2,6,6-tetramethylpiperidin-4-yl)-3-methoxybenzamide | 5-Cl | 6-Me | CH | CH | OMe |
| 36 | 4-(4-Methylbenzimidazol-2-yl)-N-(2,2,6,6-tetramethylpiperidin-4-yl)-3-methoxybenzamide | 4-Me | H | CH | CH | OMe |
| 37 | 4-(7-Hydroxybenzimidazol-2-yl)-N-(2,2,6,6-tetramethylpiperidin-4-yl)-3-methoxybenzamide | 7-OH | H | CH | CH | OMe |
| 38 | 4-(5-Chloro-6-fluorobenzimidazol-2-yl)-N-(2,2,6,6-tetramethylpiperidin-4-yl)-3-methoxybenzamide | 5-Cl | 6-F | CH | CH | OMe |
| 39 | 4-(4-Chloro-6-trifluoromethylbenzimidazol-2-yl)-N-(2,2,6,6-tetramethylpiperidin-4-yl)-3-methoxybenzamide | 4-Cl | 6-CF₃ | CH | CH | OMe |
| 40 | 4-(1H-Naphth[2,3-d]imidazol-2-yl)-N-(2,2,6,6-tetramethylpiperidin-4-yl)-3-methoxybenzamide | 5,6(—CH=CH—CH=CH—) | | CH | CH | OMe |
| 41 | 4-(6-Trifluoromethylbenzimidazol-2-yl)-N-(2,2,6,6-tetramethylpiperidin-4-yl)-3-methoxybenzamide | 6-CF₃ | H | CH | CH | OMe |
| 42 | 4-(1H-Imidazo[4,5-b]pyridin-2-yl)-N-(2,2,6,6-tetramethylpiperidin-4-yl)-3-methoxybenzamide | H | H | N | CH | OMe |
| 43 | 4-(1H-Purin-8-yl)-N-(2,2,6,6-tetramethylpiperidin-4-yl)-3-methoxybenzamide | H | H | N | N | OMe |
| 44 | 4-(6-Methoxybenzimidazol-2-yl)-N-(2,2,6,6-tetramethylpiperidin-4-yl)-3-ethoxybenzamide | 6-OMe | H | CH | CH | OEt |
| 45 | 4-(5-Bromo-6,7-dimethylbenzimidazol-2-yl)-N-(2,2,6,6-tetramethylpiperidin-4-yl)-3-ethoxybenzamide | 5-Br | 6-Me | CH | C(Me) | OEt |
| 46 | 4-(5-Chloro-6-methylbenzimidazol-2-yl)-N-(2,2,6,6-tetramethylpiperidin-4-yl)-3-ethoxybenzamide | 5-Cl | 6-Me | CH | CH | OEt |
| 47 | 4-(4-Methylbenzimidazol-2-yl)-N-(2,2,6,6-tetramethylpiperidin-4-yl)-3-ethoxybenzamide | 4-Me | H | CH | CH | OEt |
| 48 | 4-(7-Hydroxybenzimidazol-2-yl)-N-(2,2,6,6-tetramethylpiperidin-4-yl)-3-ethoxybenzamide | 7-OH | H | CH | CH | OEt |
| 49 | 4-(5-Chloro-6-fluorobenzimidazol-2-yl)-N-(2,2,6,6-tetramethylpiperidin-4-yl)-3-ethoxybenzamide | 5-Cl | 6-F | CH | CH | OEt |
| 50 | 4-(4-Chloro-6-trifluoromethylbenzimidazol-2-yl)-N-(2,2,6,6-tetramethylpiperidin-4-yl)-3-ethoxybenzamide | 4-Cl | 6-CF₃ | CH | CH | OEt |
| 51 | 4-(1H-Naphth[2,3-d]imidazol-2-yl)-N-(2,2,6,6-tetramethylpiperidin-4-yl)-3-ethoxybenzamide | 5,6(—CH=CH—CH=CH—) | | CH | CH | OEt |
| 52 | 4-(6-Trifluoromethylbenzimidazol-2-yl)-N-(2,2,6,6-tetramethylpiperidin-4-yl)-3-ethoxybenzamide | 6-CF₃ | H | CH | CH | OEt |
| 53 | 4-(1H-Imidazo[4,5-b]pyridin-2-yl)-N-(2,2,6,6-tetramethylpiperidin-4-yl)-3-ethoxybenzamide | H | H | N | CH | OEt |
| 54 | 4-(1H-Purin-8-yl)-N-(2,2,6,6-tetramethylpiperidin-4-yl)-3-ethoxybenzamide | H | H | N | N | OEt |
| 55 | 4-(5-Bromo-6,7-dimethylbenzimidazol-2-yl)-N-(2,2,6,6-tetramethylpiperidin-4-yl)-3-methylbenzamide | 5-Br | 6-Me | CH | C(Me) | Me |
| 56 | 4-(5-Chloro-6-methylbenzimidazol-2-yl)-N-(2,2,6,6-tetramethylpiperidin-4-yl)-3-methylbenzamide | 5-Cl | 6-Me | CH | CH | Me |
| 57 | 4-(4-Methylbenzimidazol-2-yl)-N-(2,2,6,6-tetramethylpiperidin-4-yl)-3-methylbenzamide | 4-Me | H | CH | CH | Me |
| 58 | 4-(7-Hydroxybenzimidazol-2-yl)-N-(2,2,6,6-tetramethylpiperidin-4-yl)-3-methylbenzamide | 7-OH | H | CH | CH | Me |
| 59 | 4-(5-Chloro-6-fluorobenzimidazol-2-yl)-N-(2,2,6,6-tetramethylpiperidin-4-yl)-3-methylbenzamide | 5-Cl | 6-F | CH | CH | Me |
| 60 | 4-(4-Chloro-6-trifluoromethylbenzimidazol-2-yl)-N-(2,2,6,6-tetramethylpiperidin-4-yl)-3-methylbenzamide | 4-Cl | 6-CF₃ | CH | CH | Me |
| 61 | 4-(1H-Naphth[2,3-d]imidazol-2-yl)-N-(2,2,6,6-tetramethylpiperidin-4-yl)-3-methylbenzamide | 5,6(—CH=CH—CH=CH—) | | CH | CH | Me |
| 62 | 4-(6-Trifluoromethylbenzimidazol-2-yl)-N-(2,2,6,6-tetramethylpiperidin-4-yl)-3-methylbenzamide | 6-CF₃ | H | CH | CH | Me |
| 63 | 4-(1H-Imidazo[4,5-b]pyridin-2-yl)-N-(2,2,6,6-tetramethylpiperidin-4-yl)-3-methylbenzamide | H | H | N | CH | Me |
| 64 | 4-(1H-Purin-8-yl)-N-(2,2,6,6-tetramethylpiperidin-4-yl)-3-methylbenzamide | H | H | N | N | Me |
| 65 | 4-(6-Methoxybenzimidazol-2-yl)-N-(2,2,6,6-tetramethylpiperidin-4-yl)-3-fluorobenzamide | 6-OMe | H | CH | CH | F |
| 66 | 4-(5-Bromo-6,7-dimethylbenzimidazol-2-yl)-N-(2,2,6,6-tetramethylpiperidin-4-yl)-3-fluorobenzamide | 5-Br | 6-Me | CH | C(Me) | F |

TABLE 2-continued

| Ex. No | Name | R₁ | R₂ | Y | Z | R₃ |
|---|---|---|---|---|---|---|
| 67 | 4-(5-Chloro-6-methylbenzimidazol-2-yl)-N-(2,2,6,6-tetramethylpiperidin-4-yl)-3-fluorobenzamide | 5-Cl | 6-Me | CH | CH | F |
| 68 | 4-(4-Methylbenzimidazol-2-yl)-N-(2,2,6,6-tetramethylpiperidin-4-yl)-3-fluorobenzamide | 4-Me | H | CH | CH | F |
| 69 | 4-(5,6-Dichlorobenzimidazol-2-yl)-N-(2,2,6,6-tetramethylpiperidin-4-yl)-3-fluorobenzamide | 5-Cl | 6-Cl | CH | CH | F |
| 70 | 4-(7-Hydroxybenzimidazol-2-yl)-N-(2,2,6,6-tetramethylpiperidin-4-yl)-3-fluorobenzamide | 7-OH | H | CH | CH | F |
| 71 | 4-(5-Chloro-6-fluorobenzimidazol-2-yl)-N-(2,2,6,6-tetramethylpiperidin-4-yl)-3-fluorobenzamide | 5-Cl | 6-F | CH | CH | F |
| 72 | 4-(4-Chloro-6-trifluoromethylbenzimidazol-2-yl)-N-(2,2,6,6-tetramethylpiperidin-4-yl)-3-fluorobenzamide | 4-Cl | 6-CF₃ | CH | CH | F |
| 73 | 4-(1H-Naphth[2,3-d]imidazol-2-yl)-N-(2,2,6,6-tetramethylpiperidin-4-yl)-3-fluorobenzamide | 5,6(—CH=CH—CH=CH—) | | CH | CH | F |
| 74 | 4-(6-Trifluoromethylbenzimidazol-2-yl)-N-(2,2,6,6-tetramethylpiperidin-4-yl)-3-fluorobenzamide | 6-CF₃ | H | CH | CH | F |
| 75 | 4-(1H-Imidazo[4,5-b]pyridin-2-yl)-N-(2,2,6,6-tetramethylpiperidin-4-yl)-3-fluorobenzamide | H | H | N | CH | F |
| 76 | 4-(6-Methoxybenzimidazol-2-yl)-N-(2,2,6,6-tetramethylpiperidin-4-yl)-3-fbromobenzamide | 6-OMe | H | CH | CH | Br |
| 77 | 4-(5-Bromo-6,7-dimethylbenzimidazol-2-yl)-N-(2,2,6,6-tetramethylpiperidin-4-yl)-3-bromobenzamide | 5-Br | 6-Me | CH | C(Me) | Br |
| 78 | 4-(5-Chloro-6-methylbenzimidazol-2-yl)-N-(2,2,6,6-tetramethylpiperidin-4-yl)-3-bromobenzamide | 5-Cl | 6-Me | CH | CH | Br |
| 79 | 4-(4-Methylbenzimidazol-2-yl)-N-(2,2,6,6-tetramethylpiperidin-4-yl)-3-bromobenzamide | 4-Me | H | CH | CH | Br |
| 80 | 4-(5,6-Dichlorobenzimidazol-2-yl)-N-(2,2,6,6-tetramethylpiperidin-4-yl)-3-bromobenzamide | 5-Cl | 6-Cl | CH | CH | Br |
| 81 | 4-(7-Hydroxybenzimidazol-2-yl)-N-(2,2,6,6-tetramethylpiperidin-4-yl)-3-bromobenzamide | 7-OH | H | CH | CH | Br |
| 82 | 4-(5-Chloro-6-fluorobenzimidazol-2-yl)-N-(2,2,6,6-tetramethylpiperidin-4-yl)-3-bromobenzamide | 5-Cl | 6-F | CH | CH | Br |
| 83 | 4-(4-Chloro-6-trifluoromethylbenzimidazol-2-yl)-N-(2,2,6,6-tetramethylpiperidin-4-yl)-3-bromobenzamide | 4-Cl | 6-CF₃ | CH | CH | Br |
| 84 | 4-(1H-Naphth[2,3-d]imidazol-2-yl)-N-(2,2,6,6-tetramethylpiperidin-4-yl)-3-bromobenzamide | 5,6(—CH=CH—CH=CH—) | | CH | CH | Br |
| 85 | 4-(6-Trifluoromethylbenzimidazol-2-yl)-N-(2,2,6,6-tetramethylpiperidin-4-yl)-3-bromobenzamide | 6-CF₃ | H | CH | CH | Br |
| 86 | 4-(1H-Imidazo[4,5-b]pyridin-2-yl)-N-(2,2,6,6-tetramethylpiperidin-4-yl)-3-bromobenzamide | H | H | N | CH | Br |

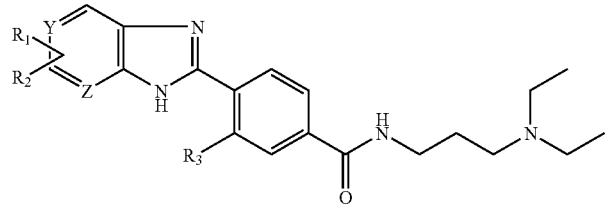

| Ex. No | Name | R₁ | R₂ | Y | Z | R₃ |
|---|---|---|---|---|---|---|
| 87 | 4-(5-Bromo-6,7-dimethylbenzimidazol-2-yl)-N-(3-diethylaminopropyl)benzamide | 5-Br | 6-Me | CH | C(Me) | H |
| 88 | 4-(5-Chloro-6-methylbenzimidazol-2-yl)-N-(3-diethylaminopropyl)benzamide | 5-Cl | 6-Me | CH | CH | H |
| 89 | 4-(4-Methylbenzimidazol-2-yl)-N-(3-diethylaminopropyl)benzamide | 4-Me | H | CH | CH | H |
| 90 | 4-(5,6-Dichlorobenzimidazol-2-yl)-N-(3-diethylaminopropyl)benzamide | 5-Cl | 6-Cl | CH | CH | H |
| 91 | 4-(7-Hydroxybenzimidazol-2-yl)-N-(3-diethylaminopropyl)benzamide | 7-OH | H | CH | CH | H |
| 92 | 4-(5-Chloro-6-fluorobenzimidazol-2-yl)-N-(3-diethylaminopropyl)benzamide | 5-Cl | 6-F | CH | CH | H |
| 93 | 4-(4-Chloro-6-trifluoromethylbenzimidazol-2-yl)-N-(3-diethylaminopropyl)benzamide | 4-Cl | 6-CF₃ | CH | CH | H |
| 94 | 4-(1H-Naphth[2,3-d]imidazol-2-yl)-N-(3-diethylaminopropyl)benzamide | 5,6(—CH=CH—CH=CH—) | | CH | CH | H |
| 95 | 4-(6-Trifluoromethylbenzimidazol-2-yl)-N-(3-diethylaminopropyl)benzamide | 6-CF₃ | H | CH | CH | H |
| 96 | 4-(6-Methoxybenzimidazol-2-yl)-N-(3-diethylaminopropyl)-3-methoxybenzamide | 6-OMe | H | CH | CH | OMe |
| 97 | 4-(5-Bromo-6,7-dimethylbenzimidazol-2-yl)-N-(3-diethylaminopropyl)-3-methoxybenzamide | 5-Br | 6-Me | CH | C(Me) | OMe |
| 98 | 4-(5-Chloro-6-methylbenzimidazol-2-yl)-N-(3-diethylaminopropyl)-3-methoxybenzamide | 5-Cl | 6-Me | CH | CH | OMe |
| 99 | 4-(5,6-Dichlorobenzimidazol-2-yl)-N-(3-diethylaminopropyl)-3-methoxybenzamide | 5-Cl | 6-Cl | CH | CH | OMe |
| 100 | 4-(7-Hydroxybenzimidazol-2-yl)-N-(3-diethylaminopropyl)-3-methoxybenzamide | 7-OH | H | CH | CH | OMe |
| 101 | 4-(5-Chloro-6-fluorobenzimidazol-2-yl)-N-(3-diethylaminopropyl)-3-methoxybenzamide | 5-Cl | 6-F | CH | CH | OMe |
| 102 | 4-(4-Chloro-6-trifluoromethylbenzimidazol-2-yl)-N-(3-diethylaminopropyl)-3-methoxybenzamide | 4-Cl | 6-CF₃ | CH | CH | OMe |
| 103 | 4-(1H-Naphth[2,3-d]imidazol-2-yl)-N-(3-diethylaminopropyl)-3-methoxybenzamide | 5,6(—CH=CH—CH=CH—) | | CH | CH | OMe |
| 104 | 4-(6-Trifluoromethylbenzimidazol-2-yl)-N-(3-diethylaminopropyl)-3-methoxybenzamide | 6-CF₃ | H | CH | CH | OMe |
| 105 | 4-(1H-Imidazo[4,5-b]pyridin-2-yl)-N-(3-diethylaminopropyl)-3-methoxybenzamide | H | H | N | CH | OMe |
| 106 | 4-(1H-Purin-8-yl)-N-(3-diethylaminopropyl)-3-methoxybenzamide | H | H | N | N | OMe |
| 107 | 4-(6-Methoxybenzimidazol-2-yl)-N-(3-diethylaminopropyl)-3-ethoxybenzamide | 6-OMe | H | CH | CH | OEt |
| 108 | 4-(5-Bromo-6,7-dimethylbenzimidazol-2-yl)-N-(3-diethylaminopropyl)-3-ethoxybenzamide | 5-Br | 6-Me | CH | C(Me) | OEt |
| 109 | 4-(5-Chloro-6-methylbenzimidazol-2-yl)-N-(3-diethylaminopropyl)-3-ethoxybenzamide | 5-Cl | 6-Me | CH | CH | OEt |
| 110 | 4-(4-Methylbenzimidazol-2-yl)-N-(3-diethylaminopropyl)-3-ethoxybenzamide | 4-Me | H | CH | CH | OEt |
| 111 | 4-(5,6-Dichlorobenzimidazol-2-yl)-N-(3-diethylaminopropyl)-3-ethoxybenzamide | 5-Cl | 6-Cl | CH | CH | OEt |
| 112 | 4-(7-Hydroxybenzimidazol-2-yl)-N-(3-diethylaminopropyl)-3-ethoxybenzamide | 7-OH | H | CH | CH | OEt |
| 113 | 4-(5-Chloro-6-fluorobenzimidazol-2-yl)-N-(3-diethylaminopropyl)-3-ethoxybenzamide | 5-Cl | 6-F | CH | CH | OEt |
| 114 | 4-(4-Chloro-6-trifluoromethylbenzimidazol-2-yl)-N-(3-diethylaminopropyl)-3-ethoxybenzamide | 4-Cl | 6-CF₃ | CH | CH | OEt |
| 115 | 4-(1H-Naphth[2,3-d]imidazol-2-yl)-N-(3-diethylaminopropyl)-3-ethoxybenzamide | 5,6(—CH=CH—CH=CH—) | | CH | CH | OEt |
| 116 | 4-(6-Trifluoromethylbenzimidazol-2-yl)-N-(3-diethylaminopropyl)-3-ethoxybenzamide | 6-CF₃ | H | CH | CH | OEt |
| 117 | 4-(1H-Purin-8-yl)-N-(3-diethylaminopropyl)-3-ethoxybenzamide | H | H | N | N | OEt |
| 118 | 4-(5-Bromo-6,7-dimethylbenzimidazol-2-yl)-N-(3-diethylaminopropyl)-3-methylbenzamide | 5-Br | 6-Me | CH | C(Me) | Me |
| 119 | 4-(5-Chloro-6-methylbenzimidazol-2-yl)-N-(3-diethylaminopropyl)-3-methylbenzamide | 5-Cl | 6-Me | CH | CH | Me |
| 120 | 4-(4-Methylbenzimidazol-2-yl)-N-(3-diethylaminopropyl)-3-methylbenzamide | 4-Me | H | CH | CH | Me |
| 121 | 4-(5,6-Dichlorobenzimidazol-2-yl)-N-(3-diethylaminopropyl)-3-methylbenzamide | 5-Cl | 6-Cl | CH | CH | Me |

TABLE 2-continued

| | | | | | | |
|---|---|---|---|---|---|---|
| 122 | 4-(7-Hydroxybenzimidazol-2-yl)-N-(3-diethylaminopropyl)-3-methylbenzamide | 7-OH | H | CH | CH | Me |
| 123 | 4-(5-Chloro-6-fluorobenzimidazol-2-yl)-N-(3-diethylaminopropyl)-3-methylbenzamide | 5-Cl | 6-F | CH | CH | Me |
| 124 | 4-(4-Chloro-6-trifluoromethylbenzimidazol-2-yl)-N-(3-diethylaminopropyl)-3-methylbenzamide | 4-Cl | 6-CF$_3$ | CH | CH | Me |
| 125 | 4-(1H-Naphth[2,3-d]imidazol-2-yl)-N-(3-diethylaminopropyl)-3-methylbenzamide | 5,6(—CH=CH—CH=CH—) | | CH | CH | Me |
| 126 | 4-(6-Trifluoromethylbenzimidazol-2-yl)-N-(3-diethylaminopropyl)-3-methylbenzamide | 6-CF$_3$ | H | CH | CH | Me |
| 127 | 4-(1H-Imidazo[4,5-b]pyridin-2-yl)-N-(3-diethylaminopropyl)-3-methylbenzamide | H | H | N | CH | Me |
| 128 | 4-(1H-Purin-8-yl)-N-(3-diethylaminopropyl)-3-methylbenzamide | H | H | N | N | Me |
| 129 | 4-(5-Bromo-6,7-dimethylbenzimidazol-2-yl)-N-(3-diethylaminopropyl)-3-fluorobenzamide | 5-Br | 6-Me | CH | C(Me) | F |
| 130 | 4-(5-Chloro-6-methylbenzimidazol-2-yl)-N-(3-diethylaminopropyl)-3-fluorobenzamide | 5-Cl | 6-Me | CH | CH | F |
| 131 | 4-(5,6-Dichlorobenzimidazol-2-yl)-N-(3-diethylaminopropyl)-3-fluorobenzamide | 5-Cl | 6-Cl | CH | CH | F |
| 132 | 4-(5-Chloro-6-fluorobenzimidazol-2-yl)-N-(3-diethylaminopropyl)-3-fluorobenzamide | 5-Cl | 6-F | CH | CH | F |
| 133 | 4-(4-Chloro-6-trifluoromethylbenzimidazol-2-yl)-N-(3-diethylaminopropyl)-3-fluorobenzamide | 4-Cl | 6-CF$_3$ | CH | CH | F |
| 134 | 4-(5-Bromo-6,7-dimethylbenzimidazol-2-yl)-N-(3-diethylaminopropyl)-3-bromobenzamide | 5-Br | 6-Me | CH | C(Me) | Br |
| 135 | 4-(5-Chloro-6-methylbenzimidazol-2-yl)-N-(3-diethylaminopropyl)-3-bromobenzamide | 5-Cl | 6-Me | CH | CH | Br |
| 136 | 4-(4-Methylbenzimidazol-2-yl)-N-(3-diethylaminopropyl)-3-bromobenzamide | 4-Me | H | CH | CH | Br |
| 137 | 4-(5-Chloro-6-fluorobenzimidazol-2-yl)-N-(3-diethylaminopropyl)-3-bromobenzamide | 5-Cl | 6-F | CH | CH | Br |
| 138 | 4-(1H-Naphth[2,3-d]imidazol-2-yl)-N-(3-diethylaminopropyl)-3-bromobenzamide | 5,6(—CH=CH—CH=CH—) | | CH | CH | Br |
| 139 | 4-(6-Trifluoromethylbenzimidazol-2-yl)-N-(3-diethylaminopropyl)-3-bromobenzamide | 6-CF$_3$ | H | CH | CH | Br |
| 140 | 4-(1H-Imidazo[4,5-b]pyridin-2-yl)-N-(3-diethylaminopropyl)-3-bromobenzamide | H | H | N | CH | Br |
| 141 | 4-(1H-Purin-8-yl)-N-(3-diethylaminopropyl)-3-bromobenzamide | H | H | N | N | Br |

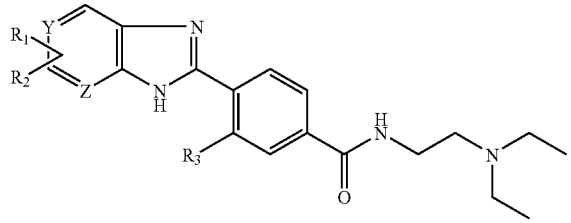

| Ex. No | Name | R$_1$ | R$_2$ | Y | Z | R$_3$ |
|---|---|---|---|---|---|---|
| 142 | 4-(5-Bromo-6,7-dimethylbenzimidazol-2-yl)-N-(3-diethylaminoethyl))benzamide | 5-Br | 6-Me | CH | C(Me) | H |
| 143 | 4-(5,6-Dichlorobenzimidazol-2-yl)-N-(3-diethylaminoethyl)benzamide | 5-Cl | 6-Cl | CH | CH | H |
| 144 | 4-(6-Trifluoromethylbenzimidazol-2-yl)-N-(3-diethylaminoethyl)benzamide | 6-CF$_3$ | H | CH | CH | H |
| 145 | 4-(5-Bromo-6,7-dimethylbenzimidazol-2-yl)-N-(3-diethylaminoethyl)-3-methoxybenzamide | 5-Br | 6-Me | CH | C(Me) | OMe |
| 146 | 4-(7-Hydroxybenzimidazol-2-yl)-N-(3-diethylaminoethyl)-3-methoxybenzamide | 7-OH | H | CH | CH | OMe |
| 147 | 4-(5-Chloro-6-fluorobenzimidazol-2-yl)-N-(3-diethylaminoethyl)-3-methoxybenzamide | 5-Cl | 6-F | CH | CH | OMe |
| 148 | 4-(4-Chloro-6-trifluoromethylbenzimidazol-2-yl)-N-(3-diethylaminoethyl)-3-methoxybenzamide | 4-Cl | 6-CF$_3$ | CH | CH | OMe |
| 149 | 4-(6-Trifluoromethylbenzimidazol-2-yl)-N-(3-diethylaminoethyl)-3-methoxybenzamide | 6-CF$_3$ | H | CH | CH | OMe |
| 150 | 4-(5-Bromo-6,7-dimethylbenzimidazol-2-yl)-N-(3-diethylaminoethyl)-3-ethoxybenzamide | 5-Br | 6-Me | CH | C(Me) | OEt |
| 151 | 4-(5-Chloro-6-methylbenzimidazol-2-yl)-N-(3-diethylaminoethyl)-3-ethoxybenzamide | 5-Cl | 6-Me | CH | CH | OEt |
| 152 | 4-(5,6-Dichlorobenzimidazol-2-yl)-N-(3-diethylaminoethyl)-3-ethoxybenzamide | 5-Cl | 6-Cl | CH | CH | OEt |
| 153 | 4-(5-Chloro-6-fluorobenzimidazol-2-yl)-N-(3-diethylaminoethyl)-3-ethoxybenzamide | 5-Cl | 6-F | CH | CH | OEt |
| 154 | 4-(4-Chloro-6-trifluoromethylbenzimidazol-2-yl)-N-(3-diethylaminoethyl)-3-ethoxybenzamide | 4-Cl | 6-CF$_3$ | CH | CH | OEt |
| 155 | 4-(5-Bromo-6,7-dimethylbenzimidazol-2-yl)-N-(3-diethylaminoethyl)-3-methylbenzamide | 5-Br | 6-Me | CH | C(Me) | Me |
| 156 | 4-(5-Chloro-6-methylbenzimidazol-2-yl)-N-(3-diethylaminoethyl)-3-methylbenzamide | 5-Cl | 6-Me | CH | CH | Me |
| 157 | 4-(5,6-Dichlorobenzimidazol-2-yl)-N-(3-diethylaminoethyl)-3-methylbenzamide | 5-Cl | 6-Cl | CH | CH | Me |
| 158 | 4-(7-Hydroxybenzimidazol-2-yl)-N-(3-diethylaminoethyl)-3-methylbenzamide | 7-OH | H | CH | CH | Me |
| 159 | 4-(5-Chloro-6-fluorobenzimidazol-2-yl)-N-(3-diethylaminoethyl)-3-methylbenzamide | 5-Cl | 6-F | CH | CH | Me |
| 160 | 4-(4-Chloro-6-trifluoromethylbenzimidazol-2-yl)-N-(3-diethylaminoethyl)-3-methylbenzamide | 4-Cl | 6-CF$_3$ | CH | CH | Me |
| 161 | 4-(1H-Naphth[2,3-d]imidazol-2-yl)-N-(3-diethylaminoethyl)-3-methylbenzamide | 5,6(—CH=CH—CH=CH—) | | CH | CH | Me |
| 162 | 4-(6-Trifluoromethylbenzimidazol-2-yl)-N-(3-diethylaminoethyl)-3-methylbenzamide | 6-CF$_3$ | H | CH | CH | Me |

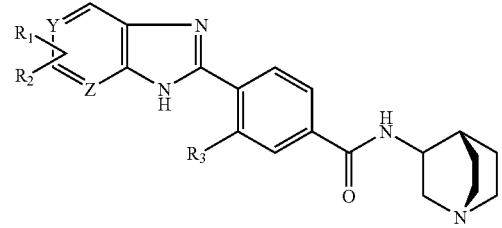

| Ex. No | Name | R$_1$ | R$_2$ | Y | Z | R$_3$ |
|---|---|---|---|---|---|---|
| 163 | 4-(6-Methoxybenzimidazol-2-yl)-N-(1-azabicyclo[2.2.2]octan-3-yl)benzamide | 6-OMe | H | CH | CH | H |
| 164 | 4-(5,6-Dichlorobenzimidazol-2-yl)-N-(1-azabicyclo[2.2.2]octan-3-yl)benzamide | 5-Cl | 6-Cl | CH | CH | H |

TABLE 2-continued

| Ex. No | Name | R₁ | R₂ | Y | Z | R₃ |
|---|---|---|---|---|---|---|
| 165 | 4-(1H-Naphth[2,3-d]imidazol-2-yl)-N-(1-azabicyclo[2.2.2]octan-3-yl)benzamide | 5,6(—CH=CH—CH=CH—) | | CH | CH | H |
| 166 | 4-(1H-Naphth[2,3-d]imidazol-2-yl)-N-(1-azabicyclo[2.2.2]octan-3-yl)-3-methoxybenzamide | 5,6(—CH=CH—CH=CH—) | | CH | CH | OMe |
| 167 | 4-(5-Chloro-6-fluorobenzimidazol-2-yl)-N-(1-azabicyclo[2.2.2]octan-3-yl)-3-ethoxybenzamide | 5-Cl | 6-F | CH | CH | OEt |
| 168 | 4-(1H-Naphth[2,3-d]imidazol-2-yl)-N-(1-azabicyclo[2.2.2]octan-3-yl)-3-ethoxybenzamide | 5,6(—CH=CH—CH=CH—) | | CH | CH | OEt |
| 169 | 4-(7-Hydroxybenzimidazol-2-yl)-N-(1-azabicyclo[2.2.2]octan-3-yl)-3-methylbenzamide | 7-OH | H | CH | CH | Me |
| 170 | 4-(5-Chloro-6-fluorobenzimidazol-2-yl)-N-(1-azabicyclo[2.2.2]octan-3-yl)-3-methylbenzamide | 5-Cl | 6-F | CH | CH | Me |
| 171 | 4-(1H-Naphth[2,3-d]imidazol-2-yl)-N-(1-azabicyclo[2.2.2]octan-3-yl)-3-methylbenzamide | 5,6(—CH=CH—CH=CH—) | | CH | CH | Me |
| 172 | 4-(1H-Naphth[2,3-d]imidazol-2-yl)-N-(1-azabicyclo[2.2.2]octan-3-yl)-3-fluorobenzamide | 5,6(—CH=CH—CH=CH—) | | CH | CH | F |
| 173 | 4-(5,6-Dichlorobenzimidazol-2-yl)-N-(1-azabicyclo[2.2.2]octan-3-yl)-3-bromobenzamide | 5-Cl | 6-Cl | CH | CH | Br |
| 174 | 4-(1H-Naphth[2,3-d]imidazol-2-yl)-N-(1-azabicyclo[2.2.2]octan-3-yl)-3-bromobenzamide | 5,6(—CH=CH—CH=CH—) | | CH | CH | Br |

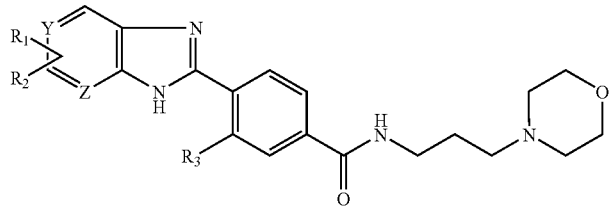

| Ex. No | Name | R₁ | R₂ | Y | Z | R₃ |
|---|---|---|---|---|---|---|
| 175 | 4-(6-Methoxybenzimidazol-2-yl)-N-[3-(morpholino)propyl]benzamide | 6-OMe | H | CH | CH | H |
| 176 | 4-(5-Bromo-6,7-dimethylbenzimidazol-2-yl)-N-[3-(morpholino)propyl]benzamide | 5-Br | 6-Me | CH | C(Me) | H |
| 177 | 4-(5-Chloro-6-methylbenzimidazol-2-yl)-N-[3-(morpholino)propyl]benzamide | 5-Cl | 6-Me | CH | CH | H |
| 178 | 4-(4-Methylbenzimidazol-2-yl)-N-[3-(morpholino)propyl]benzamide | 4-Me | H | CH | CH | H |
| 179 | 4-(5,6-Dichlorobenzimidazol-2-yl)-N-[3-(morpholino)propyl]benzamide | 5-Cl | 6-Cl | CH | CH | H |
| 180 | 4-(7-Hydroxybenzimidazol-2-yl)-N-[3-(morpholino)propyl]benzamide | 7-OH | H | CH | CH | H |
| 181 | 4-(5-Chloro-6-fluorobenzimidazol-2-yl)-N-[3-(morpholino)propyl]benzamide | 5-Cl | 6-F | CH | CH | H |
| 182 | 4-(4-Chloro-6-trifluoromethylbenzimidazol-2-yl)-N-[3-(morpholino)propyl]benzamide | 4-Cl | 6-CF₃ | CH | CH | H |
| 183 | 4-(1H-Naphth[2,3-d]imidazol-2-yl)-N-[3-(morpholino)propyl]benzamide | 5,6(—CH=CH—CH=CH—) | | CH | CH | H |
| 184 | 4-(6-Trifluoromethylbenzimidazol-2-yl)-N-[3-(morpholino)propyl]benzamide | 6-CF₃ | H | CH | CH | H |
| 185 | 4-(6-Methoxybenzimidazol-2-yl)-N-[3-(morpholino)propyl]-3-methoxybenzamide | 6-OMe | H | CH | CH | OMe |
| 186 | 4-(5-Bromo-6,7-dimethylbenzimidazol-2-yl)-N-[3-(morpholino)propyl]-3-methoxybenzamide | 5-Br | 6-Me | CH | C(Me) | OMe |
| 187 | 4-(5-Chloro-6-methylbenzimidazol-2-yl)-N-[3-(morpholino)propyl]-3-methoxybenzamide | 5-Cl | 6-Me | CH | CH | OMe |
| 188 | 4-(4-Methylbenzimidazol-2-yl)-N-[3-(morpholino)propyl]-3-methoxybenzamide | 4-Me | H | CH | CH | OMe |
| 189 | 4-(5,6-Dichlorobenzimidazol-2-yl)-N-[3-(morpholino)propyl]-3-methoxybenzamide | 5-Cl | 6-Cl | CH | CH | OMe |
| 190 | 4-(7-Hydroxybenzimidazol-2-yl)-N-[3-(morpholino)propyl]-3-methoxybenzamide | 7-OH | H | CH | CH | OMe |
| 191 | 4-(5-Chloro-6-fluorobenzimidazol-2-yl)-N-[3-(morpholino)propyl]-3-methoxybenzamide | 5-Cl | 6-F | CH | CH | OMe |
| 192 | 4-(4-Chloro-6-trifluoromethylbenzimidazol-2-yl)-N-[3-(morpholino)propyl]-3-methoxybenzamide | 4-Cl | 6-CF₃ | CH | CH | OMe |
| 193 | 4-(1H-Naphth[2,3-d]imidazol-2-yl)-N-[3-(morpholino)propyl]-3-methoxybenzamide | 5,6(—CH=CH—CH=CH—) | | CH | CH | OMe |
| 194 | 4-(6-Trifluoromethylbenzimidazol-2-yl)-N-(3-(morpholino)propyl)-3-methoxybenzamide | 6-CF₃ | H | CH | CH | OMe |
| 195 | 4-(1H-Imidazo[4,5-b]pyridin-2-yl)-N-[3-(morpholino)propyl]-3-methoxybenzamide | H | H | N | CH | OMe |
| 196 | 4-(6-Methoxybenzimidazol-2-yl)-N-[3-(morpholino)propyl]-3-ethoxybenzamide | 6-OMe | H | CH | CH | OEt |
| 197 | 4-(5-Bromo-6,7-dimethylbenzimidazol-2-yl)-N-[3-(morpholino)propyl]-3-ethoxybenzamide | 5-Br | 6-Me | CH | C(Me) | OEt |
| 198 | 4-(5-Chloro-6-methylbenzimidazol-2-yl)-N-[3-(morpholino)propyl]-3-ethoxybenzamide | 5-Cl | 6-Me | CH | CH | OEt |
| 199 | 4-(4-Methylbenzimidazol-2-yl)-N-[3-(morpholino)propyl]-3-ethoxybenzamide | 4-Me | H | CH | CH | OEt |
| 200 | 4-(5,6-Dichlorobenzimidazol-2-yl)-N-[3-(morpholino)propyl]-3-ethoxybenzamide | 5-Cl | 6-Cl | CH | CH | OEt |
| 201 | 4-(7-Hydroxybenzimidazol-2-yl)-N-[3-(morpholino)propyl]-3-ethoxybenzamide | 7-OH | H | CH | CH | OEt |
| 202 | 4-(5-Chloro-6-fluorobenzimidazol-2-yl)-N-[3-(morpholino)propyl]-3-ethoxybenzamide | 5-Cl | 6-F | CH | CH | OEt |
| 203 | 4-(4-Chloro-6-trifluoromethylbenzimidazol-2-yl)-N-[3-(morpholino)propyl]-3-ethoxybenzamide | 4-Cl | 6-CF₃ | CH | CH | OEt |
| 204 | 4-(1H-Naphth[2,3-d]imidazol-2-yl)-N-[3-(morpholino)propyl]-3-ethoxybenzamide | 5,6(—CH=CH—CH=CH—) | | CH | CH | OEt |
| 205 | 4-(6-Trifluoromethylbenzimidazol-2-yl)-N-[3-(morpholino)propyl]-3-ethoxybenzamide | 6-CF₃ | H | CH | CH | OEt |
| 206 | 4-(1H-Imidazo[4,5-b]pyridin-2-yl)-N-[3-(morpholino)propyl]-3-ethoxybenzamide | H | H | N | CH | OEt |
| 207 | 4-(1H-Purin-8-yl)-N-[3-(morpholino)propyl]-3-ethoxybenzamide | H | H | N | N | OEt |
| 208 | 4-(6-Methoxybenzimidazol-2-yl)-N-[3-(morpholino)propyl]-3-methylbenzamide | 6-OMe | H | CH | CH | Me |
| 209 | 4-(5-Bromo-6,7-dimethylbenzimidazol-2-yl)-N-[3-(morpholino)propyl]-3-methylbenzamide | 5-Br | 6-Me | CH | C(Me) | Me |
| 210 | 4-(5-Chloro-6-methylbenzimidazol-2-yl)-N-[3-(morpholino)propyl]-3-methylbenzamide | 5-Cl | 6-Me | CH | CH | Me |
| 211 | 4-(4-Methylbenzimidazol-2-yl)-N-[3-(morpholino)propyl]-3-methylbenzamide | 4-Me | H | CH | CH | Me |
| 212 | 4-(5,6-Dichlorobenzimidazol-2-yl)-N-[3-(morpholino)propyl]-3-methylbenzamide | 5-Cl | 6-Cl | CH | CH | Me |
| 213 | 4-(7-Hydroxybenzimidazol-2-yl)-N-(3-(morpholino)propyl)-3-methylbenzamide | 7-OH | H | CH | CH | Me |
| 214 | 4-(5-Chloro-6-fluorobenzimidazol-2-yl)-N-[3-(morpholino)propyl]-3-methylbenzamide | 5-Cl | 6-F | CH | CH | Me |
| 215 | 4-(4-Chloro-6-trifluoromethylbenzimidazol-2-yl)-N-[3-(morpholino)propyl]-3-methylbenzamide | 4-Cl | 6-CF₃ | CH | CH | Me |

TABLE 2-continued

| No | Name | R₁ | R₂ | Y | Z | |
|---|---|---|---|---|---|---|
| 216 | 4-(1H-Naphth[2,3-d]imidazol-2-yl)-N-[3-(morpholino)propyl]-3-methylbenzamide | 5,6(—CH=CH—CH=CH—) | | CH | CH | Me |
| 217 | 4-(6-Trifluoromethylbenzimidazol-2-yl)-N-[3-(morpholino)propyl]-3-methylbenzamide | 6-CF₃ | H | CH | CH | Me |
| 218 | 4-(1H-Imidazo[4,5-b]pyridin-2-yl)-N-[3-(morpholino)propyl]-3-methylbenzamide | H | H | N | CH | Me |
| 219 | 4-(1H-Purin-8-yl)-N-[3-(morpholino)propyl]-3-methylbenzamide | H | H | N | N | Me |
| 220 | 4-(6-Methoxybenzimidazol-2-yl)-N-[3-(morpholino)propyl]-3-fluorobenzamide | 6-OMe | H | CH | CH | F |
| 221 | 4-(5-Bromo-6,7-dimethylbenzimidazol-2-yl)-N-[3-(morpholino)propyl]-3-fluorobenzamide | 5-Br | 6-Me | CH | C(Me) | F |
| 222 | 4-(5-Chloro-6-methylbenzimidazol-2-yl)-N-[3-(morpholino)propyl]-3-fluorobenzamide | 5-Cl | 6-Me | CH | CH | F |
| 223 | 4-(4-Methylbenzimidazol-2-yl)-N-[3-(morpholino)propyl]-3-fluorobenzamide | 4-Me | H | CH | CH | F |
| 224 | 4-(5,6-Dichlorobenzimidazol-2-yl)-N-[3-(morpholino)propyl]-3-fluorobenzamide | 5-Cl | 6-Cl | CH | CH | F |
| 225 | 4-(5-Chloro-6-fluorobenzimidazol-2-yl)-N-[3-(morpholino)propyl]-3-fluorobenzamide | 5-Cl | 6-F | CH | CH | F |
| 226 | 4-(4-Chloro-6-trifluoromethylbenzimidazol-2-yl)-N-[3-(morpholino)propyl]-3-fluorobenzamide | 4-Cl | 6-CF₃ | CH | CH | F |
| 227 | 4-(1H-Naphth[2,3-d]imidazol-2-yl)-N-[3-(morpholino)propyl]-3-fluorobenzamide | 5,6(—CH=CH—CH=CH—) | | CH | CH | F |
| 228 | 4-(6-Trifluoromethylbenzimidazol-2-yl)-N-[3-(morpholino)propyl]-3-fluorobenzamide | 6-CF₃ | H | CH | CH | F |
| 229 | 4-(1H-Imidazo[4,5-b]pyridin-2-yl)-N-[3-(morpholino)propyl]-3-fluorobenzamide | H | H | N | CH | F |
| 230 | 4-(6-Methoxybenzimidazol-2-yl)-N-[3-(morpholino)propyl]-3-bromobenzamide | 6-OMe | H | CH | CH | Br |
| 231 | 4-(5-Bromo-6,7-dimethylbenzimidazol-2-yl)-N-[3-(morpholino)propyl]-3-bromobenzamide | 5-Br | 6-Me | CH | C(Me) | Br |
| 232 | 4-(5-Chloro-6-methylbenzimidazol-2-yl)-N-[3-(morpholino)propyl]-3-bromobenzamide | 5-Cl | 6-Me | CH | CH | Br |
| 233 | 4-(4-Methylbenzimidazol-2-yl)-N-[3-(morpholino)propyl]-3-bromobenzamide | 4-Me | H | CH | CH | Br |
| 234 | 4-(5,6-Dichlorobenzimidazol-2-yl)-N-[3-(morpholino)propyl]-3-bromobenzamide | 5-Cl | 6-Cl | CH | CH | Br |
| 235 | 4-(5-Chloro-6-fluorobenzimidazol-2-yl)-N-[3-(morpholino)propyl]-3-bromobenzamide | 5-Cl | 6-F | CH | CH | Br |
| 236 | 4-(4-Chloro-6-trifluoromethylbenzimidazol-2-yl)-N-[3-(morpholino)propyl]-3- | 4-Cl | 6-CF₃ | CH | CH | Br |
| 237 | 4-(6-Trifluoromethylbenzimidazol-2-yl)-N-[3-(morpholino)propyl]-3-bromobenzamide | 6-CF₃ | H | CH | CH | Br |

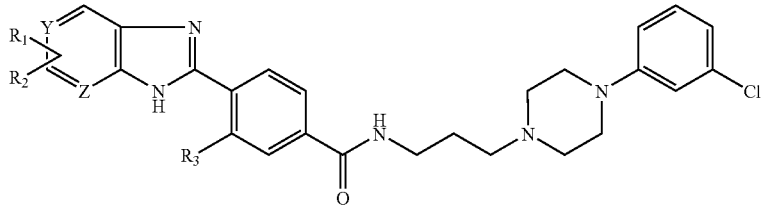

| Ex. No | Name | R₁ | R₂ | Y | Z | R₃ |
|---|---|---|---|---|---|---|
| 238 | 4-(6-Methoxybenzimidazol-2-yl)-N-[3-[4-(3-chlorophenyl)piperazinyl]propyl]benzamide | 6-OMe | H | CH | CH | H |
| 239 | 4-(5-Bromo-6,7-dimethylbenzimidazol-2-yl)-N-[3-[4-(3-chlorophenyl)piperazinyl]propyl]benzamide | 5-Br | 6-Me | CH | C(Me) | H |
| 240 | 4-(5-Chloro-6-methylbenzimidazol-2-yl)-N-[3-[4-(3-chlorophenyl)piperazinyl]propyl]benzamide | 5-Cl | 6-Me | CH | CH | H |
| 241 | 4-(4-Methylbenzimidazol-2-yl)-N-[3-[4-(3-chlorophenyl)piperazinyl]propyl]benzamide | 4-Me | H | CH | CH | H |
| 242 | 4-(5,6-Dichlorobenzimidazol-2-yl)-N-[3-[4-(3-chlorophenyl)piperazinyl]propyl]benzamide | 5-Cl | 6-Cl | CH | CH | H |
| 243 | 4-(7-Hydroxybenzimidazol-2-yl)-N-[3-[4-(3-chlorophenyl)piperazinyl]propyl]benzamide | 7-OH | H | CH | CH | H |
| 244 | 4-(5-Chloro-6-fluorobenzimidazol-2-yl)-N-[3-[4-(3-chlorophenyl)piperazinyl]propyl]benzamide | 5-Cl | 6-F | CH | CH | H |
| 245 | 4-(4-Chloro-6-trifluoromethylbenzimidazol-2-yl)-N-[3-[4-(3-chlorophenyl)piperazinyl]propyl]benzamide | 4-Cl | 6-CF₃ | CH | CH | H |
| 246 | 4-(1H-Naphth[2,3-d]imidazol-2-yl)-N-[3-[4-(3-chlorophenyl)piperazinyl]propyl]benzamide | 5,6(—CH=CH—CH=CH—) | | CH | CH | H |
| 247 | 4-(6-Trifluoromethylbenzimidazol-2-yl)-N-[3-[4-(3-chlorophenyl)piperazinyl]propyl]benzamide | 6-CF₃ | H | CH | CH | H |
| 248 | 4-(1H-Imidazo[4,5-b]pyridin-2-yl)-N-[3-[4-(3-chlorophenyl)piperazinyl]propyl]benzamide | H | H | N | CH | H |
| 249 | 4-(1H-Purin-8-yl)-N-[3-[4-(3-chlorophenyl)piperazinyl]propyl]benzamide | H | H | N | N | H |
| 250 | 4-(6-Methoxybenzimidazol-2-yl)-N-[3-[4-(3-chlorophenyl)piperazinyl]propyl]-3-methoxybenzamide | 6-OMe | H | CH | CH | OMe |
| 251 | 4-(5-Chloro-6-methylbenzimidazol-2-yl)-N-[3-[4-(3-chlorophenyl)piperazinyl]propyl]-3-methoxybenzamide | 5-Cl | 6-Me | CH | CH | OMe |
| 252 | 4-(4-Methylbenzimidazol-2-yl)-N-[3-[4-(3-chlorophenyl)piperazinyl]propyl]-3-methoxybenzamide | 4-Me | H | CH | CH | OMe |
| 253 | 4-(5,6-Dichlorobenzimidazol-2-yl)-N-[3-[4-(3-chlorophenyl)piperazinyl]propyl]-3-methoxybenzamide | 5-Cl | 6-Cl | CH | CH | OMe |
| 254 | 4-(7-Hydroxybenzimidazol-2-yl)-N-[3-[4-(3-chlorophenyl)piperazinyl]propyl]-3-methoxybenzamide | 7-OH | H | CH | CH | OMe |
| 255 | 4-(5-Chloro-6-fluorobenzimidazol-2-yl)-N-[3-[4-(3-chlorophenyl)piperazinyl]propyl]-3-methoxybenzamide | 5-Cl | 6-F | CH | CH | OMe |
| 256 | 4-(4-Chloro-6-trifluoromethylbenzimidazol-2-yl)-N-[3-[4-(3-chlorophenyl)piperazinyl]propyl]-3-methoxybenzamide | 4-Cl | 6-CF₃ | CH | CH | OMe |
| 257 | 4-(1H-Naphth[2,3-d]imidazol-2-yl)-N-[3-[4-(3-chlorophenyl)piperazinyl]propyl]-3-methoxybenzamide | 5,6(—CH=CH—CH=CH—) | | CH | CH | OMe |
| 258 | 4-(6-Trifluoromethylbenzimidazol-2-yl)-N-[3-[4-(3-chlorophenyl)piperazinyl]propyl]-3-methoxybenzamide | 6-CF₃ | H | CH | CH | OMe |
| 259 | 4-(1H-Imidazo[4,5-b]pyridin-2-yl)-N-[3-[4-(3-chlorophenyl)piperazinyl]propyl]-3-methoxybenzamide | H | H | N | CH | OMe |
| 260 | 4-(1H-Purin-8-yl)-N-[3-[4-(3-chlorophenyl)piperazinyl]propyl]-3-methoxybenzamide | H | H | N | N | OMe |

TABLE 2-continued

| | | | | | | |
|---|---|---|---|---|---|---|
| 261 | 4-(6-Methoxybenzimidazol-2-yl)-N-[3-[4-(3-chlorophenyl)piperazinyl]propyl]-3-ethoxybenzamide | 6-OMe | H | CH | CH | OEt |
| 262 | 4-(5-Bromo-6,7-dimethylbenzimidazol-2-yl)-N-[3-[4-(3-chlorophenyl)piperazinyl]propyl]-3-ethoxybenzamide | 5-Br | 6-Me | CH | C(Me) | OEt |
| 263 | 4-(5-Chloro-6-methylbenzimidazol-2-yl)-N-[3-[4-(3-chlorophenyl)piperazinyl]propyl]-3-ethoxybenzamide | 5-Cl | 6-Me | CH | CH | OEt |
| 264 | 4-(4-Methylbenzimidazol-2-yl)-N-[3-[4-(3-chlorophenyl)piperazinyl]propyl]-3-ethoxybenzamide | 4-Me | H | CH | CH | OEt |
| 265 | 4-(5,6-Dichlorobenzimidazol-2-yl)-N-[3-[4-(3-chlorophenyl)piperazinyl]propyl]-3-ethoxybenzamide | 5-Cl | 6-Cl | CH | CH | OEt |
| 266 | 4-(7-Hydroxybenzimidazol-2-yl)-N-[3-[4-(3-chlorophenyl)piperazinyl]propyl]-3-ethoxybenzamide | 7-OH | H | CH | CH | OEt |
| 267 | 4-(5-Chloro-6-fluorobenzimidazol-2-yl)-N-[3-[4-(3-chlorophenyl)piperazinyl]propyl]-3-ethoxybenzamide | 5-Cl | 6-F | CH | CH | OEt |
| 268 | 4-(4-Chloro-6-trifluoromethylbenzimidazol-2-yl)-N-[3-[4-(3-chlorophenyl)piperazinyl]propyl]-3-ethoxybenzamide | 4-Cl | 6-CF$_3$ | CH | CH | OEt |
| 269 | 4-(1H-Naphth[2,3-d]imidazol-2-yl)-N-[3-[4-(3-chlorophenyl)piperazinyl]propyl]-3-ethoxybenzamide | 5,6-(—CH=CH—CH=CH—) | | CH | CH | OEt |
| 270 | 4-(6-Trifluoromethylbenzimidazol-2-yl)-N-[3-[4-(3-chlorophenyl)piperazinyl]propyl]-3-ethoxybenzamide | 6-CF$_3$ | H | CH | CH | OEt |
| 271 | 4-(1H-Imidazo[4,5-b]pyridin-2-yl)-N-[3-[4-(3-chlorophenyl)piperazinyl]propyl]-3-ethoxybenzamide | H | H | N | CH | OEt |
| 272 | 4-(1H-Purin-8-yl)-N-[3-[4-(3-chlorophenyl)piperazinyl]propyl]-3-ethoxybenzamide | H | H | N | N | OEt |
| 273 | 4-(6-Methoxybenzimidazol-2-yl)-N-[3-[4-(3-chlorophenyl)piperazinyl]propyl]-3-methylbenzamide | 6-OMe | H | CH | CH | Me |
| 274 | 4-(5-Bromo-6,7-dimethylbenzimidazol-2-yl)-N-[3-[4-(3-chlorophenyl)piperazinyl]propyl]-3-methylbenzamide | 5-Br | 6-Me | CH | C(Me) | Me |
| 275 | 4-(5-Chloro-6-methylbenzimidazol-2-yl)-N-[3-[4-(3-chlorophenyl)piperazinyl]propyl]-3-methylbenzamide | 5-Cl | 6-Me | CH | CH | Me |
| 276 | 4-(4-Methylbenzimidazol-2-yl)-N-[3-[4-(3-chlorophenyl)piperazinyl]propyl]-3-methylbenzamide | 4-Me | H | CH | CH | Me |
| 277 | 4-(5,6-Dichlorobenzimidazol-2-yl)-N-[3-[4-(3-chlorophenyl)piperazinyl]propyl]-3-methylbenzamide | 5-Cl | 6-Cl | CH | CH | Me |
| 278 | 4-(7-Hydroxybenzimidazol-2-yl)-N-[3-[4-(3-chlorophenyl)piperazinyl]propyl]-3-methylbenzamide | 7-OH | H | CH | CH | Me |
| 279 | 4-(5-Chloro-6-fluorobenzimidazol-2-yl)-N-[3-[4-(3-chlorophenyl)piperazinyl]propyl]-3-methylbenzamide | 5-Cl | 6-F | CH | CH | Me |
| 280 | 4-(4-Chloro-6-trifluoromethylbenzimidazol-2-yl)-N-[3-[4-(3-chlorophenyl)piperazinyl]propyl]-3-methylbenzamide | 4-Cl | 6-CF$_3$ | CH | CH | Me |
| 281 | 4-(1H-Naphth[2,3-d]imidazol-2-yl)-N-[3-[4-(3-chlorophenyl)piperazinyl]propyl]-3-methylbenzamide | 5,6-(—CH=CH—CH=CH—) | | CH | CH | Me |
| 282 | 4-(6-Trifluoromethylbenzimidazol-2-yl)-N-[3-[4-(3-chlorophenyl)piperazinyl]propyl]-3-methylbenzamide | 6-CF$_3$ | H | CH | CH | Me |
| 283 | 4-(1H-Imidazo[4,5-b]pyridin-2-yl)-N-[3-[4-(3-chlorophenyl)piperazinyl]propyl]-3-methylbenzamide | H | H | N | CH | Me |
| 284 | 4-(1H-Purin-8-yl)-N-[3-[4-(3-chlorophenyl)piperazinyl]propyl]-3-methylbenzamide | H | H | N | N | Me |
| 285 | 4-(6-Methoxybenzimidazol-2-yl)-N-[3-[4-(3-chlorophenyl)piperazinyl]propyl]-3-fluorobenzamide | 6-OMe | H | CH | CH | F |
| 286 | 4-(5-Bromo-6,7-dimethylbenzimidazol-2-yl)-N-[3-[4-(3-chlorophenyl)piperazinyl]propyl]-3-fluorobenzamide | 5-Br | 6-Me | CH | C(Me) | F |
| 287 | 4-(5-Chloro-6-methylbenzimidazol-2-yl)-N-[3-[4-(3-chlorophenyl)piperazinyl]propyl]-3-fluorobenzamide | 5-Cl | 6-Me | CH | CH | F |
| 288 | 4-(4-Methylbenzimidazol-2-yl)-N-[3-[4-(3-chlorophenyl)piperazinyl]propyl]-3-fluorobenzamide | 4-Me | H | CH | CH | F |
| 289 | 4-(5,6-Dichlorobenzimidazol-2-yl)-N-[3-[4-(3-chlorophenyl)piperazinyl]propyl]-3-fluorobenzamide | 5-Cl | 6-Cl | CH | CH | F |
| 290 | 4-(7-Hydroxybenzimidazol-2-yl)-N-[3-[4-(3-chlorophenyl)piperazinyl]propyl]-3-fluorobenzamide | 7-OH | H | CH | CH | F |
| 291 | 4-(5-Chloro-6-fluorobenzimidazol-2-yl)-N-[3-[4-(3-chlorophenyl)piperazinyl]propyl]-3-fluorobenzamide | 5-Cl | 6-F | CH | CH | F |
| 292 | 4-(4-Chloro-6-trifluoromethylbenzimidazol-2-yl)-N-[3-[4-(3-chlorophenyl)piperazinyl]propyl]-3-fluorobenzamide | 4-Cl | 6-CF$_3$ | CH | CH | F |
| 293 | 4-(1H-Naphth[2,3-d]imidazol-2-yl)-N-[3-[4-(3-chlorophenyl)piperazinyl]propyl]-3-fluorobenzamide | 5,6-(—CH=CH—CH=CH—) | | CH | CH | F |
| 294 | 4-(6-Trifluoromethylbenzimidazol-2-yl)-N-[3-[4-(3-chlorophenyl)piperazinyl]propyl]-3-fluorobenzamide | 6-CF$_3$ | H | CH | CH | F |
| 295 | 4-(1H-Imidazo[4,5-b]pyridin-2-yl)-N-[3-[4-(3-chlorophenyl)piperazinyl]propyl]-3-fluorobenzamide | H | H | N | CH | F |
| 296 | 4-(1H-Purin-8-yl)-N-[3-[4-(3-chlorophenyl)piperazinyl]propyl]-3-fluorobenzamide | H | H | N | N | F |
| 297 | 4-(6-Methoxybenzimidazol-2-yl)-N-[3-[4-(3-chlorophenyl)piperazinyl]propyl]-3-bromobenzamide | 6-OMe | H | CH | CH | Br |
| 298 | 4-(5-Bromo-6,7-dimethylbenzimidazol-2-yl)-N-[3-[4-(3-chlorophenyl)piperazinyl]propyl]-3-bromobenzamide | 5-Br | 6-Me | CH | C(Me) | Br |
| 299 | 4-(5-Chloro-6-methylbenzimidazol-2-yl)-N-[3-[4-(3-chlorophenyl)piperazinyl]propyl]-3-bromobenzamide | 5-Cl | 6-Me | CH | CH | Br |
| 300 | 4-(4-Methylbenzimidazol-2-yl)-N-[3-[4-(3-chlorophenyl)piperazinyl]propyl]-3-bromobenzamide | 4-Me | H | CH | CH | Br |
| 301 | 4-(5,6-Dichlorobenzimidazol-2-yl)-N-[3-[4-(3-chlorophenyl)piperazinyl]propyl]-3-bromobenzamide | 5-Cl | 6-Cl | CH | CH | Br |

TABLE 2-continued

| Ex. No | Name | R₁ | R₂ | Y | Z | R₃ |
|---|---|---|---|---|---|---|
| 302 | 4-(7-Hydroxybenzimidazol-2-yl)-N-[3-[4-(3-chlorophenyl)piperazinyl]propyl]-3-bromobenzamide | 7-OH | H | CH | CH | Br |
| 303 | 4-(5-Chloro-6-fluorobenzimidazol-2-yl)-N-[3-[4-(3-chlorophenyl)piperazinyl]propyl]-3-bromobenzamide | 5-Cl | 6-F | CH | CH | Br |
| 304 | 4-(4-Chloro-6-trifluoromethylbenzimidazol-2-yl)-N-[3-[4-(3-chlorophenyl)piperazinyl]propyl]-3-bromobenzamide | 4-Cl | 6-CF₃ | CH | CH | Br |
| 305 | 4-(1H-Naphth[2,3-d]imidazol-2-yl)-N-[3-[4-(3-chlorophenyl)piperazinyl]propyl]-3-bromobenzamide | 5,6(—CH=CH—CH=CH—) | | CH | CH | Br |
| 306 | 4-(6-Trifluoromethylbenzimidazol-2-yl)-N-[3-[4-(3-chlorophenyl)piperazinyl]propyl]-3-bromobenzamide | 6-CF₃ | H | CH | CH | Br |
| 307 | 4-(1H-Imidazo[4,5-b]pyridin-2-yl)-N-[3-[4-(3-chlorophenyl)piperazinyl]propyl]-3-bromobenzamide | H | H | N | CH | Br |
| 308 | 4-(1H-Purin-8-yl)-N-[3-[4-(3-chlorophenyl)piperazinyl]propyl]-3-bromobenzamide | H | H | N | N | Br |

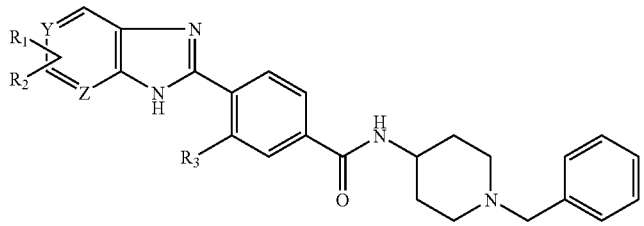

| Ex. No | Name | R₁ | R₂ | Y | Z | R₃ |
|---|---|---|---|---|---|---|
| 309 | 4-(5-Bromo-6,7-dimethylbenzimidazol-2-yl)-N-(1-phenylmethylpiperidinyl-4-yl)benzamide | 5-Br | 6-Me | CH | C(Me) | H |
| 310 | 4-(5-Chloro-6-methylbenzimidazol-2-yl)-N-(1-phenylmethylpiperidinyl-4-yl)benzamide | 5-Cl | 6-Me | CH | CH | H |
| 311 | 4-(4-Methylbenzimidazol-2-yl)-N-(1-phenylmethylpiperidinyl-4-yl)benzamide | 4-Me | H | CH | CH | H |
| 312 | 4-(5,6-Dichlorobenzimidazol-2-yl)-N-(1-phenylmethylpiperidinyl-4-yl)benzamide | 5-Cl | 6-Cl | CH | CH | H |
| 313 | 4-(7-Hydroxybenzimidazol-2-yl)-N-(1-phenylmethylpiperidinyl-4-yl)benzamide | 7-OH | H | CH | CH | H |
| 314 | 4-(5-Chloro-6-fluorobenzimidazol-2-yl)-N-(1-phenylmethylpiperidinyl-4-yl)benzamide | 5-Cl | 6-F | CH | CH | H |
| 315 | 4-(4-Chloro-6-trifluoromethylbenzimidazol-2-yl)-N-(1-phenylmethylpiperidinyl-4-yl)benzamide | 4-Cl | 6-CF₃ | CH | CH | H |
| 316 | 4-(1H-Naphth[2,3-d]imidazol-2-yl)-N-(1-phenylmethylpiperidinyl-4-yl)benzamide | 5,6(—CH=CH—CH=CH—) | | CH | CH | H |
| 317 | 4-(6-Trifluoromethylbenzimidazol-2-yl)-N-(1-phenylmethylpiperidinyl-4-yl)benzamide | 6-CF₃ | H | CH | CH | H |
| 318 | 4-(1H-Imidazo[4,5-b]pyridin-2-yl)-N-(1-phenylmethylpiperidinyl-4-yl)benzamide | H | H | N | CH | H |
| 319 | 4-(1H-Purin-8-yl)-N-(1-phenylmethylpiperidinyl-4-yl)benzamide | H | H | N | N | H |
| 320 | 4-(6-Methoxybenzimidazol-2-yl)-N-(1-phenylmethylpiperidinyl-4-yl)-3-methoxybenzamide | 6-OMe | H | CH | CH | OMe |
| 321 | 4-(5-Bromo-6,7-dimethylbenzimidazol-2-yl)-N-(1-phenylmethylpiperidinyl-4-yl)-3-methoxybenzamide | 5-Br | 6-Me | CH | C(Me) | OMe |
| 322 | 4-(5-Chloro-6-methylbenzimidazol-2-yl)-N-(1-phenylmethylpiperidinyl-4-yl)-3-methoxybenzamide | 5-Cl | 6-Me | CH | CH | OMe |
| 323 | 4-(4-Methylbenzimidazol-2-yl)-N-(1-phenylmethylpiperidinyl-4-yl)-3-methoxybenzamide | 4-Me | H | CH | CH | OMe |
| 324 | 4-(5,6-Dichlorobenzimidazol-2-yl)-N-(1-phenylmethylpiperidinyl-4-yl)-3-methoxybenzamide | 5-Cl | 6-Cl | CH | CH | OMe |
| 325 | 4-(7-Hydroxybenzimidazol-2-yl)-N-(1-phenylmethylpiperidinyl-4-yl)-3-methoxybenzamide | 7-OH | H | CH | CH | OMe |
| 326 | 4-(5-Chloro-6-fluorobenzimidazol-2-yl)-N-(1-phenylmethylpiperidinyl-4-yl)-3-methoxybenzamide | 5-Cl | 6-F | CH | CH | OMe |
| 327 | 4-(4-Chloro-6-trifluoromethylbenzimidazol-2-yl)-N-(1-phenylmethylpiperidinyl-4-yl)-3-methoxybenzamide | 4-Cl | 6-CF₃ | CH | CH | OMe |
| 328 | 4-(1H-Naphth[2,3-d]imidazol-2-yl)-N-(1-phenylmethylpiperidinyl-4-yl)-3-methoxybenzamide | 5,6(—CH=CH—CH=CH—) | | CH | CH | OMe |
| 329 | 4-(6-Trifluoromethylbenzimidazol-2-yl)-N-(1-phenylmethylpiperidinyl-4-yl)-3-methoxybenzamide | 6-CF₃ | H | CH | CH | OMe |
| 330 | 4-(1H-Imidazo[4,5-b]pyridin-2-yl)-N-(1-phenylmethylpiperidinyl-4-yl)-3-methoxybenzamide | H | H | N | CH | OMe |
| 331 | 4-(1H-Purin-8-yl)-N-(1-phenylmethylpiperidinyl-4-yl)-3-methoxybenzamide | H | H | N | N | OMe |
| 332 | 4-(6-Methoxybenzimidazol-2-yl)-N-(1-phenylmethylpiperidinyl-4-yl)-3-ethoxybenzamide | 6-OMe | H | CH | CH | OEt |
| 333 | 4-(5-Bromo-6,7-dimethylbenzimidazol-2-yl)-N-(1-phenylmethylpiperidinyl-4-yl)-3-ethoxybenzamide | 5-Br | 6-Me | CH | C(Me) | OEt |
| 334 | 4-(5-Chloro-6-methylbenzimidazol-2-yl)-N-(1-phenylmethylpiperidinyl-4-yl)-3-ethoxybenzamide | 5-Cl | 6-Me | CH | CH | OEt |
| 335 | 4-(4-Methylbenzimidazol-2-yl)-N-(1-phenylmethylpiperidinyl-4-yl)-3-ethoxybenzamide | 4-Me | H | CH | CH | OEt |
| 336 | 4-(5,6-Dichlorobenzimidazol-2-yl)-N-(1-phenylmethylpiperidinyl-4-yl)-3-ethoxybenzamide | 5-Cl | 6-Cl | CH | CH | OEt |
| 337 | 4-(7-Hydroxybenzimidazol-2-yl)-N-(1-phenylmethylpiperidinyl-4-yl)-3-ethoxybenzamide | 7-OH | H | CH | CH | OEt |
| 338 | 4-(5-Chloro-6-fluorobenzimidazol-2-yl)-N-(1-phenylmethylpiperidinyl-4-yl)-3-ethoxybenzamide | 5-Cl | 6-F | CH | CH | OEt |
| 339 | 4-(4-Chloro-6-trifluoromethylbenzimidazol-2-yl)-N-(1-phenylmethylpiperidinyl-4-yl)-3-ethoxybenzamide | 4-Cl | 6-CF₃ | CH | CH | OEt |
| 340 | 4-(1H-Naphth[2,3-d]imidazol-2-yl)-N-(1-phenylmethylpiperidinyl-4-yl)-3-ethoxybenzamide | 5,6(—CH=CH—CH=CH—) | | CH | CH | OEt |
| 341 | 4-(6-Trifluoromethylbenzimidazol-2-yl)-N-(1-phenylmethylpiperidinyl-4-yl)-3-ethoxybenzamide | 6-CF₃ | H | CH | CH | OEt |
| 342 | 4-(1H-Imidazo[4,5-b]pyridin-2-yl)-N-(1-phenylmethylpiperidinyl-4-yl)-3-ethoxybenzamide | H | H | N | CH | OEt |
| 343 | 4-(1H-Purin-8-yl)-N-(1-phenylmethylpiperidinyl-4-yl)-3-ethoxybenzamide | H | H | N | N | OEt |

TABLE 2-continued

| Ex. No | Name | R1 | R2 | Y | Z | R3 |
|---|---|---|---|---|---|---|
| 344 | 4-(6-Methoxybenzimidazol-2-yl)-N-(1-phenylmethylpiperidinyl-4-yl)-3-methylbenzamide | 6-OMe | H | CH | CH | Me |
| 345 | 4-(5-Bromo-6,7-dimethylbenzimidazol-2-yl)-N-(1-phenylmethylpiperidinyl-4-yl)-3-methylbenzamide | 5-Br | 6-Me | CH | C(Me) | Me |
| 346 | 4-(5-Chloro-6-methylbenzimidazol-2-yl)-N-(1-phenylmethylpiperidinyl-4-yl)-3-methylbenzamide | 5-Cl | 6-Me | CH | CH | Me |
| 347 | 4-(4-Methylbenzimidazol-2-yl)-N-(1-phenylmethylpiperidinyl-4-yl)-3-methylbenzamide | 4-Me | H | CH | CH | Me |
| 348 | 4-(5,6-Dichlorobenzimidazol-2-yl)-N-(1-phenylmethylpiperidinyl-4-yl)-3-methylbenzamide | 5-Cl | 6-Cl | CH | CH | Me |
| 349 | 4-(7-Hydroxybenzimidazol-2-yl)-N-(1-phenylmethylpiperidinyl-4-yl)-3-methylbenzamide | 7-OH | H | CH | CH | Me |
| 350 | 4-(5-Chloro-6-fluorobenzimidazol-2-yl)-N-(1-phenylmethylpiperidinyl-4-yl)-3-methylbenzamide | 5-Cl | 6-F | CH | CH | Me |
| 351 | 4-(4-Chloro-6-trifluoromethylbenzimidazol-2-yl)-N-(1-phenylmethylpiperidinyl-4-yl)-3-methylbenzamide | 4-Cl | 6-$CF_3$ | CH | CH | Me |
| 352 | 4-(1H-Naphth[2,3-d]imidazol-2-yl)-N-(1-phenylmethylpiperidinyl-4-yl)-3-methylbenzamide | 5,6(—CH=CH—CH=CH—) | | CH | CH | Me |
| 353 | 4-(6-Trifluoromethylbenzimidazol-2-yl)-N-(1-phenylmethylpiperidinyl-4-yl)-3-methylbenzamide | 6-$CF_3$ | H | CH | CH | Me |
| 354 | 4-(1H-Imidazo[4,5-b]pyridin-2-yl)-N-(1-phenylmethylpiperidinyl-4-yl)-3-methylbenzamide | H | H | N | CH | Me |
| 355 | 4-(1H-Purin-8-yl)-N-(1-phenylmethylpiperidinyl-4-yl)-3-methylbenzamide | H | H | N | N | Me |
| 356 | 4-(6-Methoxybenzimidazol-2-yl)-N-(1-phenylmethylpiperidinyl-4-yl)-3-fluorobenzamide | 6-OMe | H | CH | CH | F |
| 357 | 4-(5-Bromo-6,7-dimethylbenzimidazol-2-yl)-N-(1-phenylmethylpiperidinyl-4-yl)-3-fluorobenzamide | 5-Br | 6-Me | CH | C(Me) | F |
| 358 | 4-(5-Chloro-6-methylbenzimidazol-2-yl)-N-(1-phenylmethylpiperidinyl-4-yl)-3-fluorobenzamide | 5-Cl | 6-Me | CH | CH | F |
| 359 | 4-(4-Methylbenzimidazol-2-yl)-N-(1-phenylmethylpiperidinyl-4-yl)-3-fluorobenzamide | 4-Me | H | CH | CH | F |
| 360 | 4-(5,6-Dichlorobenzimidazol-2-yl)-N-(1-phenylmethylpiperidinyl-4-yl)-3-fluorobenzamide | 5-Cl | 6-Cl | CH | CH | F |
| 361 | 4-(7-Hydroxybenzimidazol-2-yl)-N-(1-phenylmethylpiperidinyl-4-yl)-3-fluorobenzamide | 7-OH | H | CH | CH | F |
| 362 | 4-(5-Chloro-6-fluorobenzimidazol-2-yl)-N-(1-phenylmethylpiperidinyl-4-yl)-3-fluorobenzamide | 5-Cl | 6-F | CH | CH | F |
| 363 | 4-(4-Chloro-6-trifluoromethylbenzimidazol-2-yl)-N-(1-phenylmethylpiperidinyl-4-yl)-3-fluorobenzamide | 4-Cl | 6-$CF_3$ | CH | CH | F |
| 364 | 4-(1H-Naphth[2,3-d]imidazol-2-yl)-N-(1-phenylmethylpiperidinyl-4-yl)-3-fluorobenzamide | 5,6(—CH=CH—CH=CH—) | | CH | CH | F |
| 365 | 4-(6-Trifluoromethylbenzimidazol-2-yl)-N-(1-phenylmethylpiperidinyl-4-yl)-3-fluorobenzamide | 6-$CF_3$ | H | CH | CH | F |
| 366 | 4-(1H-Imidazo[4,5-b]pyridin-2-yl)-N-(1-phenylmethylpiperidinyl-4-yl)-3-fluorobenzamide | H | H | N | CH | F |
| 367 | 4-(1H-Purin-8-yl)-N-(1-phenylmethylpiperidinyl-4-yl)-3-fluorobenzamide | H | H | N | N | F |
| 368 | 4-(6-Methoxybenzimidazol-2-yl)-N-(1-phenylmethylpiperidinyl-4-yl)-3-bromobenzamide | 6-OMe | H | CH | CH | Br |
| 369 | 4-(5-Bromo-6,7-dimethylbenzimidazol-2-yl)-N-(1-phenylmethylpiperidinyl-4-yl)-3-bromobenzamide | 5-Br | 6-Me | CH | C(Me) | Br |
| 370 | 4-(5-Chloro-6-methylbenzimidazol-2-yl)-N-(1-phenylmethylpiperidinyl-4-yl)-3-bromobenzamide | 5-Cl | 6-Me | CH | CH | Br |
| 371 | 4-(4-Methylbenzimidazol-2-yl)-N-(1-phenylmethylpiperidinyl-4-yl)-3-bromobenzamide | 4-Me | H | CH | CH | Br |
| 372 | 4-(5,6-Dichlorobenzimidazol-2-yl)-N-(1-phenylmethylpiperidinyl-4-yl)-3-bromobenzamide | 5-Cl | 6-Cl | CH | CH | Br |
| 373 | 4-(7-Hydroxybenzimidazol-2-yl)-N-(1-phenylmethylpiperidinyl-4-yl)-3-bromobenzamide | 7-OH | H | CH | CH | Br |
| 374 | 4-(4-Chloro-6-trifluoromethylbenzimidazol-2-yl)-N-(1-phenylmethylpiperidinyl-4-yl)-3-bromobenzamide | 4-Cl | 6-$CF_3$ | CH | CH | Br |
| 375 | 4-(1H-Naphth[2,3-d]imidazol-2-yl)-N-(1-phenylmethylpiperidinyl-4-yl)-3-bromobenzamide | 5,6(—CH=CH—CH=CH—) | | CH | CH | Br |
| 376 | 4-(6-Trifluoromethylbenzimidazol-2-yl)-N-(1-phenylmethylpiperidinyl-4-yl)-3-bromobenzamide | 6-$CF_3$ | H | CH | CH | Br |
| 377 | 4-(1H-Imidazo[4,5-b]pyridin-2-yl)-N-(1-phenylmethylpiperidinyl-4-yl)-3-bromobenzamide | H | H | N | CH | Br |
| 378 | 4-(1H-Purin-8-yl)-N-(1-phenylmethylpiperidinyl-4-yl)-3-bromobenzamide | H | H | N | N | Br |

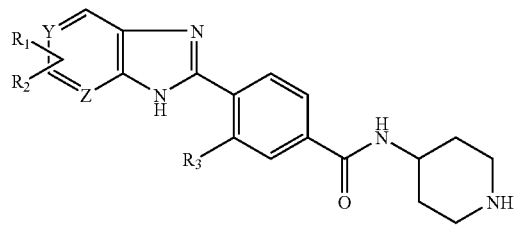

| Ex. No | Name | R1 | R2 | Y | Z | R3 |
|---|---|---|---|---|---|---|
| 379 | 4-(6-Methoxybenzimidazol-2-yl)-N-(piperidinyl-4-yl)benzamide | 6-OMe | H | CH | CH | H |
| 380 | 4-(5-Bromo-6,7-dimethylbenzimidazol-2-yl)-N-(piperidinyl-4-yl)benzamide | 5-Br | 6-Me | CH | C(Me) | H |

TABLE 2-continued

| | | | | | | |
|---|---|---|---|---|---|---|
| 381 | 4-(5-Chloro-6-methylbenzimidazol-2-yl)-N-(piperidinyl-4-yl)benzamide | 5-Cl | 6-Me | CH | CH | H |
| 382 | 4-(4-Methylbenzimidazol-2-yl)-N-(piperidinyl-4-yl)benzamide | 4-Me | H | CH | CH | H |
| 383 | 4-(5,6-Dichlorobenzimidazol-2-yl)-N-(piperidinyl-4-yl)benzamide | 5-Cl | 6-Cl | CH | CH | H |
| 384 | 4-(7-Hydroxybenzimidazol-2-yl)-N-(piperidinyl-4-yl)benzamide | 7-OH | H | CH | CH | H |
| 385 | 4-(5-Chloro-6-fluorobenzimidazol-2-yl)-N-(piperidinyl-4-yl)benzamide | 5-Cl | 6-F | CH | CH | H |
| 386 | 4-(4-Chloro-6-trifluoromethylbenzimidazol-2-yl)-N-(piperidinyl-4-yl)benzamide | 4-Cl | 6-CF$_3$ | CH | CH | H |
| 387 | 4-(1H-Naphth[2,3-d]imidazol-2-yl)-N-(piperidinyl-4-yl)benzamide | 5,6(—CH=CH—CH=CH—) | | CH | CH | H |
| 388 | 4-(6-Trifluoromethylbenzimidazol-2-yl)-N-(piperidinyl-4-yl)benzamide | 6-CF$_3$ | H | CH | CH | H |
| 389 | 4-(1H-Imidazo[4,5-b]pyridin-2-yl)-N-(piperidinyl-4-yl)benzamide | H | H | N | CH | H |
| 390 | 4-(1H-Purin-8-yl)-N-(piperidinyl-4-yl)benzamide | H | H | N | N | H |
| 391 | 4-(5-Bromo-6,7-dimethylbenzimidazol-2-yl)-N-(piperidinyl-4-yl)-3-methoxybenzamide | 5-Br | 6-Me | CH | C(Me) | OMe |
| 392 | 4-(5-Chloro-6-methylbenzimidazol-2-yl)-N-(piperidinyl-4-yl)-3-methoxybenzamide | 5-Cl | 6-Me | CH | CH | OMe |
| 393 | 4-(4-Methylbenzimidazol-2-yl)-N-(piperidinyl-4-yl)-3-methoxybenzamide | 4-Me | H | CH | CH | OMe |
| 394 | 4-(5,6-Dichlorobenzimidazol-2-yl)-N-(piperidinyl-4-yl)-3-methoxybenzamide | 5-Cl | 6-Cl | CH | CH | OMe |
| 395 | 4-(7-Hydroxybenzimidazol-2-yl)-N-(piperidinyl-4-yl)-3-methoxybenzamide | 7-OH | H | CH | CH | OMe |
| 396 | 4-(5-Chloro-6-fluorobenzimidazol-2-yl)-N-(piperidinyl-4-yl)-3-methoxybenzamide | 5-Cl | 6-F | CH | CH | OMe |
| 397 | 4-(4-Chloro-6-trifluoromethylbenzimidazol-2-yl)-N-(piperidinyl-4-yl)-3-methoxybenzamide | 4-Cl | 6-CF$_3$ | CH | CH | OMe |
| 398 | 4-(1H-Naphth[2,3-d]imidazol-2-yl)-N-(piperidinyl-4-yl)-3-methoxybenzamide | 5,6(—CH=CH—CH=CH—) | | CH | CH | OMe |
| 399 | 4-(6-Trifluoromethylbenzimidazol-2-yl)-N-(piperidinyl-4-yl)-3-methoxybenzamide | 6-CF$_3$ | H | CH | CH | OMe |
| 400 | 4-(1H-Imidazo[4,5-b]pyridin-2-yl)-N-(piperidinyl-4-yl)-3-methoxybenzamide | H | H | N | CH | OMe |
| 401 | 4-(1H-Purin-8-yl)-N-(piperidinyl-4-yl)-3-methoxybenzamide | H | H | N | N | OMe |
| 402 | 4-(6-Methoxybenzimidazol-2-yl)-N-(piperidinyl-4-yl)-3-ethoxybenzamide | 6-OMe | H | CH | CH | OEt |
| 403 | 4-(5-Bromo-6,7-dimethylbenzimidazol-2-yl)-N-(piperidinyl-4-yl)-3-ethoxybenzamide | 5-Br | 6-Me | CH | C(Me) | OEt |
| 404 | 4-(5-Chloro-6-methylbenzimidazol-2-yl)-N-(piperidinyl-4-yl)-3-ethoxybenzamide | 5-Cl | 6-Me | CH | CH | OEt |
| 405 | 4-(4-Methylbenzimidazol-2-yl)-N-(piperidinyl-4-yl)-3-ethoxybenzamide | 4-Me | H | CH | CH | OEt |
| 406 | 4-(5,6-Dichlorobenzimidazol-2-yl)-N-(piperidinyl-4-yl)-3-ethoxybenzamide | 5-Cl | 6-Cl | CH | CH | OEt |
| 407 | 4-(7-Hydroxybenzimidazol-2-yl)-N-(piperidinyl-4-yl)-3-ethoxybenzamide | 7-OH | H | CH | CH | OEt |
| 408 | 4-(5-Chloro-6-fluorobenzimidazol-2-yl)-N-(piperidinyl-4-yl)-3-ethoxybenzamide | 5-Cl | 6-F | CH | CH | OEt |
| 409 | 4-(4-Chloro-6-trifluoromethylbenzimidazol-2-yl)-N-(piperidinyl-4-yl)-3-ethoxybenzamide | 4-Cl | 6-CF$_3$ | CH | CH | OEt |
| 410 | 4-(1H-Naphth[2,3-d]imidazol-2-yl)-N-(piperidinyl-4-yl)-3-ethoxybenzamide | 5,6(—CH=CH—CH=CH—) | | CH | CH | OEt |
| 411 | 4-(6-Trifluoromethylbenzimidazol-2-yl)-N-(piperidinyl-4-yl)-3-ethoxybenzamide | 6-CF$_3$ | H | CH | CH | OEt |
| 412 | 4-(1H-Imidazo[4,5-b]pyridin-2-yl)-N-(piperidinyl-4-yl)-3-ethoxybenzamide | H | H | N | CH | OEt |
| 413 | 4-(1H-Purin-8-yl)-N-(piperidinyl-4-yl)-3-ethoxybenzamide | H | H | N | N | OEt |
| 414 | 4-(6-Methoxybenzimidazol-2-yl)-N-(piperidinyl-4-yl)-3-methylbenzamide | 6-OMe | H | CH | CH | Me |
| 415 | 4-(5-Bromo-6,7-dimethylbenzimidazol-2-yl)-N-(piperidinyl-4-yl)-3-methylbenzamide | 5-Br | 6-Me | CH | C(Me) | Me |
| 416 | 4-(5-Chloro-6-methylbenzimidazol-2-yl)-N-(piperidinyl-4-yl)-3-methylbenzamide | 5-Cl | 6-Me | CH | CH | Me |
| 417 | 4-(4-Methylbenzimidazol-2-yl)-N-(piperidinyl-4-yl)-3-methylbenzamide | 4-Me | H | CH | CH | Me |
| 418 | 4-(5,6-Dichlorobenzimidazol-2-yl)-N-(piperidinyl-4-yl)-3-methylbenzamide | 5-Cl | 6-Cl | CH | CH | Me |
| 419 | 4-(7-Hydroxybenzimidazol-2-yl)-N-(piperidinyl-4-yl)-3-methylbenzamide | 7-OH | H | CH | CH | Me |
| 420 | 4-(5-Chloro-6-fluorobenzimidazol-2-yl)-N-(piperidinyl-4-yl)-3-methylbenzamide | 5-Cl | 6-F | CH | CH | Me |
| 421 | 4-(4-Chloro-6-trifluoromethylbenzimidazol-2-yl)-N-(piperidinyl-4-yl)-3-methylbenzamide | 4-Cl | 6-CF$_3$ | CH | CH | Me |
| 422 | 4-(1H-Naphth[2,3-d]imidazol-2-yl)-N-(piperidinyl-4-yl)-3-methylbenzamide | 5,6(—CH=CH—CH=CH—) | | CH | CH | Me |
| 423 | 4-(6-Trifluoromethylbenzimidazol-2-yl)-N-(piperidinyl-4-yl)-3-methylbenzamide | 6-CF$_3$ | H | CH | CH | Me |
| 424 | 4-(1H-Imidazo[4,5-b]pyridin-2-yl)-N-(piperidinyl-4-yl)-3-methylbenzamide | H | H | N | CH | Me |
| 425 | 4-(6-Methoxybenzimidazol-2-yl)-N-(piperidinyl-4-yl)-3-fluorobenzamide | 6-OMe | H | CH | CH | F |
| 426 | 4-(5-Bromo-6,7-dimethylbenzimidazol-2-yl)-N-(piperidinyl-4-yl)-3-fluorobenzamide | 5-Br | 6-Me | CH | C(Me) | F |
| 427 | 4-(5-Chloro-6-methylbenzimidazol-2-yl)-N-(piperidinyl-4-yl)-3-fluorobenzamide | 5-Cl | 6-Me | CH | CH | F |
| 428 | 4-(4-Methylbenzimidazol-2-yl)-N-(piperidinyl-4-yl)-3-fluorobenzamide | 4-Me | H | CH | CH | F |
| 429 | 4-(5,6-Dichlorobenzimidazol-2-yl)-N-(piperidinyl-4-yl)-3-fluorobenzamide | 5-Cl | 6-Cl | CH | CH | F |
| 430 | 4-(5-Chloro-6-fluorobenzimidazol-2-yl)-N-(piperidinyl-4-yl)-3-fluorobenzamide | 5-Cl | 6-F | CH | CH | F |
| 431 | 4-(4-Chloro-6-trifluoromethylbenzimidazol-2-yl)-N-(piperidinyl-4-yl)-3-fluorobenzamide | 4-Cl | 6-CF$_3$ | CH | CH | F |
| 432 | 4-(1H-Naphth[2,3-d]imidazol-2-yl)-N-(piperidinyl-4-yl)-3-fluorobenzamide | 5,6(—CH=CH—CH=CH—) | | CH | CH | F |
| 433 | 4-(6-Trifluoromethylbenzimidazol-2-yl)-N-(piperidinyl-4-yl)-3-fluorobenzamide | 6-CF$_3$ | H | CH | CH | F |
| 434 | 4-(1H-Imidazo[4,5-b]pyridin-2-yl)-N-(piperidinyl-4-yl)-3-fluorobenzamide | H | H | N | CH | F |
| 435 | 4-(6-Methoxybenzimidazol-2-yl)-N-(piperidinyl-4-yl)-3-bromobenzamide | 6-OMe | H | CH | CH | Br |
| 436 | 4-(5-Bromo-6,7-dimethylbenzimidazol-2-yl)-N-(piperidinyl-4-yl)-3-bromobenzamide | 5-Br | 6-Me | CH | C(Me) | Br |
| 437 | 4-(5-Chloro-6-methylbenzimidazol-2-yl)-N-(piperidinyl-4-yl)-3-bromobenzamide | 5-Cl | 6-Me | CH | CH | Br |
| 438 | 4-(4-Methylbenzimidazol-2-yl)-N-(piperidinyl-4-yl)-3-bromobenzamide | 4-Me | H | CH | CH | Br |
| 439 | 4-(5,6-Dichlorobenzimidazol-2-yl)-N-(piperidinyl-4-yl)-3-bromobenzamide | 5-Cl | 6-Cl | CH | CH | Br |
| 440 | 4-(7-Hydroxybenzimidazol-2-yl)-N-(piperidinyl-4-yl)-3-bromobenzamide | 7-OH | H | CH | CH | Br |
| 441 | 4-(5-Chloro-6-fluorobenzimidazol-2-yl)-N-(piperidinyl-4-yl)-3-bromobenzamide | 5-Cl | 6-F | CH | CH | Br |
| 442 | 4-(4-Chloro-6-trifluoromethylbenzimidazol-2-yl)-N-(piperidinyl-4-yl)-3-bromobenzamide | 4-Cl | 6-CF$_3$ | CH | CH | Br |
| 443 | 4-(1H-Naphth[2,3-d]imidazol-2-yl)-N-(piperidinyl-4-yl)-3-bromobenzamide | 5,6(—CH=CH—CH=CH—) | | CH | CH | Br |
| 444 | 4-(6-Trifluoromethylbenzimidazol-2-yl)-N-(piperidinyl-4-yl)-3-bromobenzamide | 6-CF$_3$ | H | CH | CH | Br |
| 445 | 4-(1H-Imidazo[4,5-b]pyridin-2-yl)-N-(piperidinyl-4-yl)-3-bromobenzamide | H | H | N | CH | Br |

TABLE 2-continued

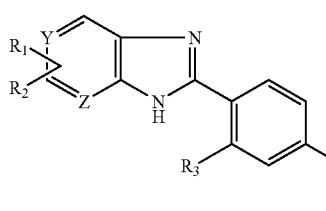

| Ex. No | Name | R₁ | R₂ | Y | Z | R₃ |
|---|---|---|---|---|---|---|
| 446 | 4-(6-Methoxybenzimidazol-2-yl)-N-[3-[4-(2-methoxy-5-chlorophenyl)piperazinyl]propyl]benzamide | 6-OMe | H | CH | CH | H |
| 447 | 4-(5-Bromo-6,7-dimethylbenzimidazol-2-yl)-N-[3-[4-(2-methoxy-5-chlorophenyl)piperazinyl]propyl]benzamide | 5-Br | 6-Me | CH | C(Me) | H |
| 448 | 4-(5-Chloro-6-methylbenzimidazol-2-yl)-N-[3-[4-(2-methoxy-5-chlorophenyl)piperazinyl]propyl]benzamide | 5-Cl | 6-Me | CH | CH | H |
| 449 | 4-(4-Methylbenzimidazol-2-yl)-N-[3-[4-(2-methoxy-5-chlorophenyl)piperazinyl]propyl]benzamide | 4-Me | H | CH | CH | H |
| 450 | 4-(5,6-Dichlorobenzimidazol-2-yl)-N-[3-[4-(2-methoxy-5-chlorophenyl)piperazinyl]propyl]benzamide | 5-Cl | 6-Cl | CH | CH | H |
| 451 | 4-(7-Hydroxybenzimidazol-2-yl)-N-[3-[4-(2-methoxy-5-chlorophenyl)piperazinyl]propyl]benzamide | 7-OH | H | CH | CH | H |
| 452 | 4-(5-Chloro-6-fluorobenzimidazol-2-yl)-N-[3-[4-(2-methoxy-5-chlorophenyl)piperazinyl]propyl]benzamide | 5-Cl | 6-F | CH | CH | H |
| 453 | 4-(4-Chloro-6-trifluoromethylbenzimidazol-2-yl)-N-[3-[4-(2-methoxy-5-chlorophenyl)piperazinyl]propyl]benzamide | 4-Cl | 6-CF₃ | CH | CH | H |
| 454 | 4-(1H-Naphth[2,3-d]imidazol-2-yl)-N-[3-[4-(2-methoxy-5-chlorophenyl)piperazinyl]propyl]benzamide | 5,6-(—CH=CH—CH=CH—) | | CH | CH | H |
| 455 | 4-(6-Trifluoromethylbenzimidazol-2-yl)-N-[3-[4-(2-methoxy-5-chlorophenyl)piperazinyl]propyl]benzamide | 6-CF₃ | H | CH | CH | H |
| 456 | 4-(1H-Purin-8-yl)-N-[3-[4-(2-methoxy-5-chlorophenyl)piperazinyl]propyl]benzamide | H | H | N | N | H |
| 457 | 4-(6-Methoxybenzimidazol-2-yl)-N-[3-[4-(2-methoxy-5-chlorophenyl)piperazinyl]propyl]-3-methoxybenzamide | 6-OMe | H | CH | CH | OMe |
| 458 | 4-(5-Bromo-6,7-dimethylbenzimidazol-2-yl)-N-[3-[4-(2-methoxy-5-chlorophenyl)piperazinyl]propyl]-3-methoxybenzamide | 5-Br | 6-Me | CH | C(Me) | OMe |
| 459 | 4-(4-Methylbenzimidazol-2-yl)-N-[3-[4-(2-methoxy-5-chlorophenyl)piperazinyl]propyl]-3-methoxybenzamide | 4-Me | H | CH | CH | OMe |
| 460 | 4-(5,6-Dichlorobenzimidazol-2-yl)-N-[3-[4-(2-methoxy-5-chlorophenyl)piperazinyl]propyl]-3-methoxybenzamide | 5-Cl | 6-Cl | CH | CH | OMe |
| 461 | 4-(7-Hydroxybenzimidazol-2-yl)-N-[3-[4-(2-methoxy-5-chlorophenyl)piperazinyl]propyl]-3-methoxybenzamide | 7-OH | H | CH | CH | OMe |
| 462 | 4-(5-Chloro-6-fluorobenzimidazol-2-yl)-N-[3-[4-(2-methoxy-5-chlorophenyl)piperazinyl]propyl]-3-methoxybenzamide | 5-Cl | 6-F | CH | CH | OMe |
| 463 | 4-(4-Chloro-6-trifluoromethylbenzimidazol-2-yl)-N-[3-[4-(2-methoxy-5-chlorophenyl)piperazinyl]propyl]-3-methoxybenzamide | 4-Cl | 6-CF₃ | CH | CH | OMe |
| 464 | 4-(1H-Naphth[2,3-d]imidazol-2-yl)-N-[3-[4-(2-methoxy-5-chlorophenyl)piperazinyl]propyl]-3-methoxybenzamide | 5,6-(—CH=CH—CH=CH—) | | CH | CH | OMe |
| 465 | 4-(6-Trifluoromethylbenzimidazol-2-yl)-N-[3-[4-(2-methoxy-5-chlorophenyl)piperazinyl]propyl]-3-methoxybenzamide | 6-CF₃ | H | CH | CH | OMe |
| 466 | 4-(1H-Imidazo[4,5-b]pyridin-2-yl)-N-[3-[4-(2-methoxy-5-chlorophenyl)piperazinyl]propyl]-3-methoxybenzamide | H | H | N | CH | OMe |
| 467 | 4-(1H-Purin-8-yl)-N-[3-[4-(2-methoxy-5-chlorophenyl)piperazinyl]propyl]-3-methoxybenzamide | H | H | N | N | OMe |
| 468 | 4-(6-Methoxybenzimidazol-2-yl)-N-[3-[4-(2-methoxy-5-chlorophenyl)piperazinyl]propyl]-3-ethoxybenzamide | 6-OMe | H | CH | CH | OEt |
| 469 | 4-(5-Bromo-6,7-dimethylbenzimidazol-2-yl)-N-[3-[4-(2-methoxy-5-chlorophenyl)piperazinyl]propyl]-3-ethoxybenzamide | 5-Br | 6-Me | CH | C(Me) | OEt |
| 470 | 4-(5-Chloro-6-methylbenzimidazol-2-yl)-N-[3-[4-(2-methoxy-5-chlorophenyl)piperazinyl]propyl]-3-ethoxybenzamide | 5-Cl | 6-Me | CH | CH | OEt |
| 471 | 4-(5,6-Dichlorobenzimidazol-2-yl)-N-[3-[4-(2-methoxy-5-chlorophenyl)piperazinyl]propyl]-3-ethoxybenzamide | 5-Cl | 6-Cl | CH | CH | OEt |
| 472 | 4-(7-Hydroxybenzimidazol-2-yl)-N-[3-[4-(2-methoxy-5-chlorophenyl)piperazinyl]propyl]-3-ethoxybenzamide | 7-OH | H | CH | CH | OEt |
| 473 | 4-(5-Chloro-6-fluorobenzimidazol-2-yl)-N-[3-[4-(2-methoxy-5-chlorophenyl)piperazinyl]propyl]-3-ethoxybenzamide | 5-Cl | 6-F | CH | CH | OEt |
| 474 | 4-(4-Chloro-6-trifluoromethylbenzimidazol-2-yl)-N-[3-[4-(2-methoxy-5-chlorophenyl)piperazinyl]propyl]-3-ethoxybenzamide | 4-Cl | 6-CF₃ | CH | CH | OEt |

TABLE 2-continued

| # | Name | | | | | |
|---|---|---|---|---|---|---|
| 475 | 4-(1H-Naphth[2,3-d]imidazol-2-yl)-N-[3-[4-(2-methoxy-5-chlorophenyl)piperazinyl]propyl]-3-ethoxybenzamide | 5,6(—CH=CH—CH=CH—) | | CH | CH | OEt |
| 476 | 4-(1H-Imidazo[4,5-b]pyridin-2-yl)-N-[3-(4-(2-methoxy-5-chlorophenyl)piperazinyl]propyl]-3-ethoxybenzamide | H | H | N | CH | OEt |
| 477 | 4-(1H-Purin-8-yl)-N-[3-[4-(2-methoxy-5-chlorophenyl)piperazinyl]propyl]-3-ethoxybenzamide | H | H | N | N | OEt |
| 478 | 4-(6-Methoxybenzimidazol-2-yl)-N-[3-[4-(2-methoxy-5-chlorophenyl)piperazinyl]propyl]-3-methylbenzamide | 6-OMe | H | CH | CH | Me |
| 479 | 4-(5-Bromo-6,7-dimethylbenzimidazol-2-yl)-N-[3-[4-(2-methoxy-5-chlorophenyl)piperazinyl]propyl]-3-methylbenzamide | 5-Br | 6-Me | CH | C(Me) | Me |
| 480 | 4-(5-Chloro-6-methylbenzimidazol-2-yl)-N-[3-[4-(2-methoxy-5-chlorophenyl)piperazinyl]propyl]-3-methylbenzamide | 5-Cl | 6-Me | CH | CH | Me |
| 481 | 4-(5,6-Dichlorobenzimidazol-2-yl)-N-[3-[4-(2-methoxy-5-chlorophenyl)piperazinyl]propyl]-3-methylbenzamide | 5-Cl | 6-Cl | CH | CH | Me |
| 482 | 4-(7-Hydroxybenzimidazol-2-yl)-N-[3-[4-(2-methoxy-5-chlorophenyl)piperazinyl]propyl]-3-methylbenzamide | 7-OH | H | CH | CH | Me |
| 483 | 4-(5-Chloro-6-fluorobenzimidazol-2-yl)-N-[3-[4-(2-methoxy-5-chlorophenyl)piperazinyl]propyl]-3-methylbenzamide | 5-Cl | 6-F | CH | CH | Me |
| 484 | 4-(4-Chloro-6-trifluoromethylbenzimidazol-2-yl)-N-[3-[4-(2-methoxy-5-chlorophenyl)piperazinyl]propyl]-3-methylbenzamide | 4-Cl | 6-$CF_3$ | CH | CH | Me |
| 485 | 4-(6-Trifluoromethylbenzimidazol-2-yl)-N-[3-[4-(2-methoxy-5-chlorophenyl)piperazinyl]propyl]-3-methylbenzamide | 6-$CF_3$ | H | CH | CH | Me |
| 486 | 4-(1H-Imidazo[4,5-b]pyridin-2-yl)-N-[3-[4-(2-methoxy-5-chlorophenyl)piperazinyl]propyl]-3-methylbenzamide | H | H | N | CH | Me |
| 487 | 4-(1H-Purin-8-yl)-N-[3-[4-(2-methoxy-5-chlorophenyl)piperazinyl]propyl]-3-methylbenzamide | H | H | N | N | Me |
| 488 | 4-(6-Methoxybenzimidazol-2-yl)-N-[3-[4-(2-methoxy-5-chlorophenyl)piperazinyl]propyl]-3-fluorobenzamide | 6-OMe | H | CH | CH | F |
| 489 | 4-(5-Bromo-6,7-dimethylbenzimidazol-2-yl)-N-[3-[4-(2-methoxy-5-chlorophenyl)piperazinyl]propyl]-3-fluorobenzamide | 5-Br | 6-Me | CH | C(Me) | F |
| 490 | 4-(5-Chloro-6-methylbenzimidazol-2-yl)-N-[3-[4-(2-methoxy-5-chlorophenyl)piperazinyl]propyl]-3-fluorobenzamide | 5-Cl | 6-Me | CH | CH | F |
| 491 | 4-(4-Methylbenzimidazol-2-yl)-N-[3-[4-(2-methoxy-5-chlorophenyl)piperazinyl]propyl]-3-fluorobenzamide | 4-Me | H | CH | CH | F |
| 492 | 4-(5,6-Dichlorobenzimidazol-2-yl)-N-[3-[4-(2-methoxy-5-chlorophenyl)piperazinyl]propyl]-3-fluorobenzamide | 5-Cl | 6-Cl | CH | CH | F |
| 493 | 4-(7-Hydroxybenzimidazol-2-yl)-N-[3-[4-(2-methoxy-5-chlorophenyl)piperazinyl]propyl]-3-fluorobenzamide | 7-OH | H | CH | CH | F |
| 494 | 4-(5-Chloro-6-fluorobenzimidazol-2-yl)-N-[3-[4-(2-methoxy-5-chlorophenyl)piperazinyl]propyl]-3-fluorobenzamide | 5-Cl | 6-F | CH | CH | F |
| 495 | 4-(4-Chloro-6-trifluoromethylbenzimidazol-2-yl)-N-[3-[4-(2-methoxy-5-chlorophenyl)piperazinyl]propyl]-3-fluorobenzamide | 4-Cl | 6-$CF_3$ | CH | CH | F |
| 496 | 4-(1H-Naphth[2,3-d]imidazol-2-yl)-N-[3-[4-(2-methoxy-5-chlorophenyl)piperazinyl]propyl]-3-fluorobenzamide | 5,6(—CH=CH—CH=CH—) | | CH | CH | F |
| 497 | 4-(6-Trifluoromethylbenzimidazol-2-yl)-N-[3-[4-(2-methoxy-5-chlorophenyl)piperazinyl]propyl]-3-fluorobenzamide | 6-$CF_3$ | H | CH | CH | F |
| 498 | 4-(1H-Imidazo[4,5-b]pyridin-2-yl)-N-[3-[4-(2-methoxy-5-chlorophenyl)piperazinyl]propyl]-3-fluorobenzamide | H | H | N | CH | F |
| 499 | 4-(1H-Purin-8-yl)-N-[3-[4-(2-methoxy-5-chlorophenyl)piperazinyl]propyl]-3-fluorobenzamide | H | H | N | N | F |
| 500 | 4-(6-Methoxybenzimidazol-2-yl)-N-[3-[4-(2-methoxy-5-chlorophenyl)piperazinyl]propyl]-3-bromobenzamide | 6-OMe | H | CH | CH | Br |
| 501 | 4-(5-Bromo-6,7-dimethylbenzimidazol-2-yl)-N-[3-[4-(2-methoxy-5-chlorophenyl)piperazinyl]propyl]-3-bromobenzamide | 5-Br | 6-Me | CH | C(Me) | Br |
| 502 | 4-(5-Chloro-6-methylbenzimidazol-2-yl)-N-[3-[4-(2-methoxy-5-chlorophenyl)piperazinyl]propyl]-3-bromobenzamide | 5-Cl | 6-Me | CH | CH | Br |
| 503 | 4-(4-Methylbenzimidazol-2-yl)-N-[3-[4-(2-methoxy-5-chlorophenyl)piperazinyl]propyl]-3-bromobenzamide | 4-Me | H | CH | CH | Br |
| 504 | 4-(5,6-Dichlorobenzimidazol-2-yl)-N-[3-[4-(2-methoxy-5-chlorophenyl)piperazinyl]propyl]-3-bromobenzamide | 5-Cl | 6-Cl | CH | CH | Br |
| 505 | 4-(7-Hydroxybenzimidazol-2-yl)-N-[3-[4-(2-methoxy-5-chlorophenyl)piperazinyl]propyl]-3-bromobenzamide | 7-OH | H | CH | CH | Br |
| 506 | 4-(5-Chloro-6-fluorobenzimidazol-2-yl)-N-[3-[4-(2-methoxy-5-chlorophenyl)piperazinyl]propyl]-3-bromobenzamide | 5-Cl | 6-F | CH | CH | Br |
| 507 | 4-(4-Chloro-6-trifluoromethylbenzimidazol-2-yl)-N-[3-[4-(2-methoxy-5-chlorophenyl)piperazinyl]propyl]-3-bromobenzamide | 4-Cl | 6-$CF_3$ | CH | CH | Br |
| 508 | 4-(1H-Naphth[2,3-d]imidazol-2-yl)-N-[3-[4-(2-methoxy-5-chlorophenyl)piperazinyl]propyl]-3-bromobenzamide | 5,6(—CH=CH—CH=CH—) | | CH | CH | Br |
| 509 | 4-(6-Trifluoromethylbenzimidazol-2-yl)-N-[3-[4-(2-methoxy-5-chlorophenyl)piperazinyl]propyl]-3-bromobenzamide | 6-$CF_3$ | H | CH | CH | Br |
| 510 | 4-(1H-Imidazo[4,5-b]pyridin-2-yl)-N-[3-[4-(2-methoxy-5-chlorophenyl)piperazinyl]propyl]-3-bromobenzamide | H | H | N | CH | Br |
| 511 | 4-(1H-Purin-8-yl)-N-[3-[4-(2-methoxy-5-chlorophenyl)piperazinyl]propyl]-3-bromobenzamide | H | H | N | N | Br |

TABLE 2-continued

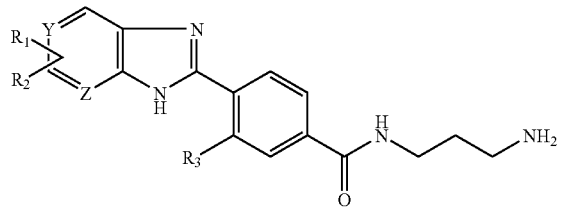

| Ex. No | Name | R₁ | R₂ | Y | Z | R₃ |
|---|---|---|---|---|---|---|
| 512 | 4-(6-Methoxybenzimidazol-2-yl)-N-(3-aminopropyl)benzamide | 6-OMe | H | CH | CH | H |
| 513 | 4-(5-Bromo-6,7-dimethylbenzimidazol-2-yl)-N-(3-aminopropyl)benzamide | 5-Br | 6-Me | CH | C(Me) | H |
| 514 | 4-(5-Chloro-6-methylbenzimidazol-2-yl)-N-(3-aminopropyl)benzamide | 5-Cl | 6-Me | CH | CH | H |
| 515 | 4-(4-Methylbenzimidazol-2-yl)-N-(3-aminopropyl)benzamide | 4-Me | H | CH | CH | H |
| 516 | 4-(5,6-Dichlorobenzimidazol-2-yl)-N-(3-aminopropyl)benzamide | 5-Cl | 6-Cl | CH | CH | H |
| 517 | 4-(7-Hydroxybenzimidazol-2-yl)-N-(3-aminopropyl)benzamide | 7-OH | H | CH | CH | H |
| 518 | 4-(5-Chloro-6-fluorobenzimidazol-2-yl)-N-(3-aminopropyl)benzamide | 5-Cl | 6-F | CH | CH | H |
| 519 | 4-(4-Chloro-6-trifluoromethylbenzimidazol-2-yl)-N-(3-aminopropyl)benzamide | 4-Cl | 6-CF₃ | CH | CH | H |
| 520 | 4-(1H-Naphth[2,3-d]imidazol-2-yl)-N-(3-aminopropyl)benzamide | 5,6(—CH=CH—CH=CH—) | | CH | CH | H |
| 521 | 4-(6-Trifluoromethylbenzimidazol-2-yl)-N-(3-aminopropyl)benzamide | 6-CF₃ | H | CH | CH | H |
| 522 | 4-(6-Methoxybenzimidazol-2-yl)-N-(3-aminopropyl)-3-methoxybenzamide | 6-OMe | H | CH | CH | OMe |
| 523 | 4-(5-Bromo-6,7-dimethylbenzimidazol-2-yl)-N-(3-aminopropyl)-3-methoxybenzamide | 5-Br | 6-Me | CH | C(Me) | OMe |
| 524 | 4-(5-Chloro-6-methylbenzimidazol-2-yl)-N-(3-aminopropyl)-3-methoxybenzamide | 5-Cl | 6-Me | CH | CH | OMe |
| 525 | 4-(4-Methylbenzimidazol-2-yl)-N-(3-aminopropyl)-3-methoxybenzamide | 4-Me | H | CH | CH | OMe |
| 526 | 4-(5,6-Dichlorobenzimidazol-2-yl)-N-(3-aminopropyl)-3-methoxybenzamide | 5-Cl | 6-Cl | CH | CH | OMe |
| 527 | 4-(7-Hydroxybenzimidazol-2-yl)-N-(3-aminopropyl)-3-methoxybenzamide | 7-OH | H | CH | CH | OMe |
| 528 | 4-(5-Chloro-6-fluorobenzimidazol-2-yl)-N-(3-aminopropyl)-3-methoxybenzamide | 5-Cl | 6-F | CH | CH | OMe |
| 529 | 4-(4-Chloro-6-trifluoromethylbenzimidazol-2-yl)-N-(3-aminopropyl)-3-methoxybenzamide | 4-Cl | 6-CF₃ | CH | CH | OMe |
| 530 | 4-(1H-Naphth[2,3-d]imidazol-2-yl)-N-(3-aminopropyl)-3-methoxybenzamide | 5,6(—CH=CH—CH=CH—) | | CH | CH | OMe |
| 531 | 4-(6-Trifluoromethylbenzimidazol-2-yl)-N-(3-aminopropyl)-3-methoxybenzamide | 6-CF₃ | H | CH | CH | OMe |
| 532 | 4-(1H-Purin-8-yl)-N-(3-aminopropyl)-3-methoxybenzamide | H | H | N | N | OMe |
| 533 | 4-(6-Methoxybenzimidazol-2-yl)-N-(3-aminopropyl)-3-ethoxybenzamide | 6-OMe | H | CH | CH | OEt |
| 534 | 4-(5-Bromo-6,7-dimethylbenzimidazol-2-yl)-N-(3-aminopropyl)-3-ethoxybenzamide | 5-Br | 6-Me | CH | C(Me) | OEt |
| 535 | 4-(5-Chloro-6-methylbenzimidazol-2-yl)-N-(3-aminopropyl)-3-ethoxybenzamide | 5-Cl | 6-Me | CH | CH | OEt |
| 536 | 4-(4-Methylbenzimidazol-2-yl)-N-(3-aminopropyl)-3-ethoxybenzamide | 4-Me | H | CH | CH | OEt |
| 537 | 4-(5,6-Dichlorobenzimidazol-2-yl)-N-(3-aminopropyl)-3-ethoxybenzamide | 5-Cl | 6-Cl | CH | CH | OEt |
| 538 | 4-(7-Hydroxybenzimidazol-2-yl)-N-(3-aminopropyl)-3-ethoxybenzamide | 7-OH | H | CH | CH | OEt |
| 539 | 4-(5-Chloro-6-fluorobenzimidazol-2-yl)-N-(3-aminopropyl)-3-ethoxybenzamide | 5-Cl | 6-F | CH | CH | OEt |
| 540 | 4-(4-Chloro-6-trifluoromethylbenzimidazol-2-yl)-N-(3-aminopropyl)-3-ethoxybenzamide | 4-Cl | 6-CF₃ | CH | CH | OEt |
| 541 | 4-(1H-Naphth[2,3-d]imidazol-2-yl)-N-(3-aminopropyl)-3-ethoxybenzamide | 5,6(—CH=CH—CH=CH—) | | CH | CH | OEt |
| 542 | 4-(6-Trifluoromethylbenzimidazol-2-yl)-N-(3-aminopropyl)-3-ethoxybenzamide | 6-CF₃ | H | CH | CH | OEt |
| 543 | 4-(1H-Imidazo[4,5-b]pyridin-2-yl)-N-(3-aminopropyl)-3-ethoxybenzamide | H | H | N | CH | OEt |
| 544 | 4-(1H-Purin-8-yl)-N-(3-aminopropyl)-3-ethoxybenzamide | H | H | N | N | OEt |
| 545 | 4-(6-Methoxybenzimidazol-2-yl)-N-(3-aminopropyl)-3-methylbenzamide | 6-OMe | H | CH | CH | Me |
| 546 | 4-(5-Bromo-6,7-dimethylbenzimidazol-2-yl)-N-(3-aminopropyl)-3-methylbenzamide | 5-Br | 6-Me | CH | C(Me) | Me |
| 547 | 4-(5-Chloro-6-methylbenzimidazol-2-yl)-N-(3-aminopropyl)-3-methylbenzamide | 5-Cl | 6-Me | CH | CH | Me |
| 548 | 4-(4-Methylbenzimidazol-2-yl)-N-(3-aminopropyl)-3-methylbenzamide | 4-Me | H | CH | CH | Me |
| 549 | 4-(5,6-Dichlorobenzimidazol-2-yl)-N-(3-aminopropyl)-3-methylbenzamide | 5-Cl | 6-Cl | CH | CH | Me |
| 550 | 4-(7-Hydroxybenzimidazol-2-yl)-N-(3-aminopropyl)-3-methylbenzamide | 7-OH | H | CH | CH | Me |
| 551 | 4-(5-Chloro-6-fluorobenzimidazol-2-yl)-N-(3-aminopropyl)-3-methylbenzamide | 5-Cl | 6-F | CH | CH | Me |
| 552 | 4-(4-Chloro-6-trifluoromethylbenzimidazol-2-yl)-N-(3-aminopropyl)-3-methylbenzamide | 4-Cl | 6-CF₃ | CH | CH | Me |
| 553 | 4-(1H-Naphth[2,3-d]imidazol-2-yl)-N-(3-aminopropyl)-3-methylbenzamide | 5,6(—CH=CH—CH=CH—) | | CH | CH | Me |
| 554 | 4-(6-Trifluoromethylbenzimidazol-2-yl)-N-(3-aminopropyl)-3-methylbenzamide | 6-CF₃ | H | CH | CH | Me |
| 555 | 4-(6-Methoxybenzimidazol-2-yl)-N-(3-aminopropyl)-3-fluorobenzamide | 6-OMe | H | CH | CH | F |
| 556 | 4-(5-Bromo-6,7-dimethylbenzimidazol-2-yl)-N-(3-aminopropyl)-3-fluorobenzamide | 5-Br | 6-Me | CH | C(Me) | F |
| 557 | 4-(5-Chloro-6-methylbenzimidazol-2-yl)-N-(3-aminopropyl)-3-fluorobenzamide | 5-Cl | 6-Me | CH | CH | F |
| 558 | 4-(4-Methylbenzimidazol-2-yl)-N-(3-aminopropyl)-3-fluorobenzamide | 4-Me | H | CH | CH | F |
| 559 | 4-(5,6-Dichlorobenzimidazol-2-yl)-N-(3-aminopropyl)-3-fluorobenzamide | 5-Cl | 6-Cl | CH | CH | F |
| 560 | 4-(7-Hydroxybenzimidazol-2-yl)-N-(3-aminopropyl)-3-fluorobenzamide | 7-OH | H | CH | CH | F |
| 561 | 4-(5-Chloro-6-fluorobenzimidazol-2-yl)-N-(3-aminopropyl)-3-fluorobenzamide | 5-Cl | 6-F | CH | CH | F |
| 562 | 4-(4-Chloro-6-trifluoromethylbenzimidazol-2-yl)-N-(3-aminopropyl)-3-fluorobenzamide | 4-Cl | 6-CF₃ | CH | CH | F |
| 563 | 4-(1H-Naphth[2,3-d]imidazol-2-yl)-N-(3-aminopropyl)-3-fluorobenzamide | 5,6(—CH=CH—CH=CH—) | | CH | CH | F |
| 564 | 4-(6-Trifluoromethylbenzimidazol-2-yl)-N-(3-aminopropyl)-3-fluorobenzamide | 6-CF₃ | H | CH | CH | F |
| 565 | 4-(6-Methoxybenzimidazol-2-yl)-N-(3-aminopropyl)-3-bromobenzamide | 6-OMe | H | CH | CH | Br |
| 566 | 4-(5-Bromo-6,7-dimethylbenzimidazol-2-yl)-N-(3-aminopropyl)-3-bromobenzamide | 5-Br | 6-Me | CH | C(Me) | Br |
| 567 | 4-(5-Chloro-6-methylbenzimidazol-2-yl)-N-(3-aminopropyl)-3-bromobenzamide | 5-Cl | 6-Me | CH | CH | Br |
| 568 | 4-(4-Methylbenzimidazol-2-yl)-N-(3-aminopropyl)-3-bromobenzamide | 4-Me | H | CH | CH | Br |
| 569 | 4-(5,6-Dichlorobenzimidazol-2-yl)-N-(3-aminopropyl)-3-bromobenzamide | 5-Cl | 6-Cl | CH | CH | Br |
| 570 | 4-(7-Hydroxybenzimidazol-2-yl)-N-(3-aminopropyl)-3-bromobenzamide | 7-OH | H | CH | CH | Br |
| 571 | 4-(5-Chloro-6-fluorobenzimidazol-2-yl)-N-(3-aminopropyl)-3-bromobenzamide | 5-Cl | 6-F | CH | CH | Br |

TABLE 2-continued

| | | | | | | |
|---|---|---|---|---|---|---|
| 572 | 4-(4-Chloro-6-trifluoromethylbenzimidazol-2-yl)-N-(3-aminopropyl)-3-bromobenzamide | 4-Cl | 6-CF$_3$ | CH | CH | Br |
| 573 | 4-(1H-Naphth[2,3-d]imidazol-2-yl)-N-(3-aminopropyl)-3-bromobenzamide | 5,6(—CH=CH—CH=CH—) | | CH | CH | Br |
| 574 | 4-(6-Trifluoromethylbenzimidazol-2-yl)-N-(3-aminopropyl)-3-bromobenzamide | 6-CF$_3$ | H | CH | CH | Br |

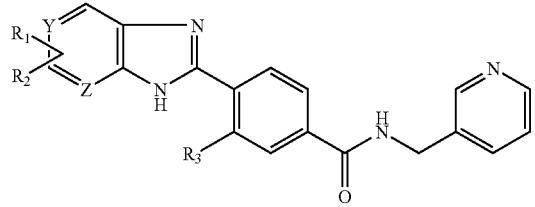

| Ex. No | Name | R$_1$ | R$_2$ | Y | Z | R$_3$ |
|---|---|---|---|---|---|---|
| 575 | 4-(6-Methoxybenzimidazol-2-yl)-N-((piridyn-3-yl)methyl)benzamide | 6-OMe | H | CH | CH | H |
| 576 | 4-(5-Bromo-6,7-dimethylbenzimidazol-2-yl)-N-((piridyn-3-yl)methyl)benzamide | 5-Br | 6-Me | CH | C(Me) | H |
| 577 | 4-(5-Chloro-6-methylbenzimidazol-2-yl)-N-((piridyn-3-yl)methyl)benzamide | 5-Cl | 6-Me | CH | CH | H |
| 578 | 4-(4-Methylbenzimidazol-2-yl)-N-((piridyn-3-yl)methyl)benzamide | 4-Me | H | CH | CH | H |
| 579 | 4-(5,6-Dichlorobenzimidazol-2-yl)-N-((piridyn-3-yl)methyl)benzamide | 5-Cl | 6-Cl | CH | CH | H |
| 580 | 4-(7-Hydroxybenzimidazol-2-yl)-N-((piridyn-3-yl)methyl)benzamide | 7-OH | H | CH | CH | H |
| 581 | 4-(5-Chloro-6-fluorobenzimidazol-2-yl)-N-((piridyn-3-yl)methyl)benzamide | 5-Cl | 6-F | CH | CH | H |
| 582 | 4-(4-Chloro-6-trifluoromethylbenzimidazol-2-yl)-N-((piridyn-3-yl)methyl)benzamide | 4-Cl | 6-CF$_3$ | CH | CH | H |
| 583 | 4-(1H-Naphth[2,3-d]imidazol-2-yl)-N-((piridyn-3-yl)methyl)benzamide | 5,6(—CH=CH—CH=CH—) | | CH | CH | H |
| 584 | 4-(6-Trifluoromethylbenzimidazol-2-yl)-N-((piridyn-3-yl)methyl)benzamide | 6-CF$_3$ | H | CH | CH | H |
| 585 | 4-(1H-Imidazo[4,5-b]pyridin-2-yl)-N-((piridyn-3-yl)methyl)benzamide | H | H | N | CH | H |
| 586 | 4-(6-Methoxybenzimidazol-2-yl)-N-((piridyn-3-yl)methyl)-3-methoxybenzamide | 6-OMe | H | CH | CH | OMe |
| 587 | 4-(5-Bromo-6,7-dimethylbenzimidazol-2-yl)-N-((piridyn-3-yl)methyl)-3-methoxybenzamide | 5-Br | 6-Me | CH | C(Me) | OMe |
| 588 | 4-(5-Chloro-6-methylbenzimidazol-2-yl)-N-((piridyn-3-yl)methyl)-3-methoxybenzamide | 5-Cl | 6-Me | CH | CH | OMe |
| 589 | 4-(4-Methylbenzimidazol-2-yl)-N-((piridyn-3-yl)methyl)-3-methoxybenzamide | 4-Me | H | CH | CH | OMe |
| 590 | 4-(5,6-Dichlorobenzimidazol-2-yl)-N-((piridyn-3-yl)methyl)-3-methoxybenzamide | 5-Cl | 6-Cl | CH | CH | OMe |
| 591 | 4-(7-Hydroxybenzimidazol-2-yl)-N-((piridyn-3-yl)methyl)-3-methoxybenzamide | 7-OH | H | CH | CH | OMe |
| 592 | 4-(5-Chloro-6-fluorobenzimidazol-2-yl)-N-((piridyn-3-yl)methyl)-3-methoxybenzamide | 5-Cl | 6-F | CH | CH | OMe |
| 593 | 4-(4-Chloro-6-trifluoromethylbenzimidazol-2-yl)-N-((piridyn-3-yl)methyl)-3-methoxybenzamide | 4-Cl | 6-CF$_3$ | CH | CH | OMe |
| 594 | 4-(1H-Naphth[2,3-d]imidazol-2-yl)-N-((piridyn-3-yl)methyl)-3-methoxybenzamide | 5,6(—CH=CH—CH=CH—) | | CH | CH | OMe |
| 595 | 4-(6-Trifluoromethylbenzimidazol-2-yl)-N-((piridyn-3-yl)methyl)-3-methoxybenzamide | 6-CF$_3$ | H | CH | CH | OMe |
| 596 | 4-(1H-Imidazo[4,5-b]pyridin-2-yl)-N-((piridyn-3-yl)methyl)-3-methoxybenzamide | H | H | N | CH | OMe |
| 597 | 4-(6-Methoxybenzimidazol-2-yl)-N-((piridyn-3-yl)methyl)-3-ethoxybenzamide | 6-OMe | H | CH | CH | OEt |
| 598 | 4-(5-Bromo-6,7-dimethylbenzimidazol-2-yl)-N-((piridyn-3-yl)methyl)-3-ethoxybenzamide | 5-Br | 6-Me | CH | C(Me) | OEt |
| 599 | 4-(5-Chloro-6-methylbenzimidazol-2-yl)-N-((piridyn-3-yl)methyl)-3-ethoxybenzamide | 5-Cl | 6-Me | CH | CH | OEt |
| 600 | 4-(4-Methylbenzimidazol-2-yl)-N-((piridyn-3-yl)methyl)-3-ethoxybenzamide | 4-Me | H | CH | CH | OEt |
| 601 | 4-(5,6-Dichlorobenzimidazol-2-yl)-N-((piridyn-3-yl)methyl)-3-ethoxybenzamide | 5-Cl | 6-Cl | CH | CH | OEt |
| 602 | 4-(7-Hydroxybenzimidazol-2-yl)-N-((piridyn-3-yl)methyl)-3-ethoxybenzamide | 7-OH | H | CH | CH | OEt |
| 603 | 4-(5-Chloro-6-fluorobenzimidazol-2-yl)-N-((piridyn-3-yl)methyl)-3-ethoxybenzamide | 5-Cl | 6-F | CH | CH | OEt |
| 604 | 4-(4-Chloro-6-trifluoromethylbenzimidazol-2-yl)-N-((piridyn-3-yl)methyl)-3-ethoxybenzamide | 4-Cl | 6-CF$_3$ | CH | CH | OEt |
| 605 | 4-(1H-Naphth[2,3-d]imidazol-2-yl)-N-((piridyn-3-yl)methyl)-3-ethoxybenzamide | 5,6(—CH=CH—CH=CH—) | | CH | CH | OEt |
| 606 | 4-(6-Trifluoromethylbenzimidazol-2-yl)-N-((piridyn-3-yl)methyl)-3-ethoxybenzamide | 6-CF$_3$ | H | CH | CH | OEt |
| 607 | 4-(1H-Imidazo[4,5-b]pyridin-2-yl)-N-((piridyn-3-yl)methyl)-3-ethoxybenzamide | H | H | N | CH | OEt |
| 608 | 4-(6-Methoxybenzimidazol-2-yl)-N-((piridyn-3-yl)methyl)-3-methylbenzamide | 6-OMe | H | CH | CH | Me |
| 609 | 4-(5-Bromo-6,7-dimethylbenzimidazol-2-yl)-N-((piridyn-3-yl)methyl)-3-methylbenzamide | 5-Br | 6-Me | CH | C(Me) | Me |
| 610 | 4-(5-Chloro-6-methylbenzimidazol-2-yl)-N-((piridyn-3-yl)methyl)-3-methylbenzamide | 5-Cl | 6-Me | CH | CH | Me |
| 611 | 4-(4-Methylbenzimidazol-2-yl)-N-((piridyn-3-yl)methyl)-3-methylbenzamide | 4-Me | H | CH | CH | Me |
| 612 | 4-(5,6-Dichlorobenzimidazol-2-yl)-N-((piridyn-3-yl)methyl)-3-methylbenzamide | 5-Cl | 6-Cl | CH | CH | Me |
| 613 | 4-(7-Hydroxybenzimidazol-2-yl)-N-((piridyn-3-yl)methyl)-3-methylbenzamide | 7-OH | H | CH | CH | Me |
| 614 | 4-(5-Chloro-6-fluorobenzimidazol-2-yl)-N-((piridyn-3-yl)methyl)-3-methylbenzamide | 5-Cl | 6-F | CH | CH | Me |
| 615 | 4-(4-Chloro-6-trifluoromethylbenzimidazol-2-yl)-N-((piridyn-3-yl)methyl)-3-methylbenzamide | 4-Cl | 6-CF$_3$ | CH | CH | Me |
| 616 | 4-(1H-Naphth[2,3-d]imidazol-2-yl)-N-((piridyn-3-yl)methyl)-3-methylbenzamide | 5,6(—CH=CH—CH=CH—) | | CH | CH | Me |
| 617 | 4-(6-Trifluoromethylbenzimidazol-2-yl)-N-((piridyn-3-yl)methyl)-3-methylbenzamide | 6-CF$_3$ | H | CH | CH | Me |
| 618 | 4-(1H-Imidazo[4,5-b]pyridin-2-yl)-N-((piridyn-3-yl)methyl)-3-methylbenzamide | H | H | N | CH | Me |
| 619 | 4-(5-Bromo-6,7-dimethylbenzimidazol-2-yl)-N-((piridyn-3-yl)methyl)-3-fluorobenzamide | 5-Br | 6-Me | CH | C(Me) | F |
| 620 | 4-(5-Chloro-6-methylbenzimidazol-2-yl)-N-((piridyn-3-yl)methyl)-3-fluorobenzamide | 5-Cl | 6-Me | CH | CH | F |
| 621 | 4-(4-Methylbenzimidazol-2-yl)-N-((piridyn-3-yl)methyl)-3-fluorobenzamide | 4-Me | H | CH | CH | F |
| 622 | 4-(5,6-Dichlorobenzimidazol-2-yl)-N-((piridyn-3-yl)methyl)-3-fluorobenzamide | 5-Cl | 6-Cl | CH | CH | F |
| 623 | 4-(5-Chloro-6-fluorobenzimidazol-2-yl)-N-((piridyn-3-yl)methyl)-3-fluorobenzamide | 5-Cl | 6-F | CH | CH | F |
| 624 | 4-(4-Chloro-6-trifluoromethylbenzimidazol-2-yl)-N-((piridyn-3-yl)methyl)-3-fluorobenzamide | 4-Cl | 6-CF$_3$ | CH | CH | F |
| 625 | 4-(1H-Naphth[2,3-d]imidazol-2-yl)-N-((piridyn-3-yl)methyl)-3-fluorobenzamide | 5,6(—CH=CH—CH=CH—) | | CH | CH | F |
| 626 | 4-(6-Trifluoromethylbenzimidazol-2-yl)-N-((piridyn-3-yl)methyl)-3-fluorobenzamide | 6-CF$_3$ | H | CH | CH | F |
| 627 | 4-(6-Methoxybenzimidazol-2-yl)-N-((piridyn-3-yl)methyl)-3-bromobenzamide | 6-OMe | H | CH | CH | Br |
| 628 | 4-(5-Bromo-6,7-dimethylbenzimidazol-2-yl)-N-((piridyn-3-yl)methyl)-3-bromobenzamide | 5-Br | 6-Me | CH | C(Me) | Br |

TABLE 2-continued

| | | | | | | | |
|---|---|---|---|---|---|---|---|
| 629 | 4-(5-Chloro-6-methylbenzimidazol-2-yl)-N-((piridyn-3-yl)methyl)-3-bromobenzamide | 5-Cl | 6-Me | CH | CH | Br | |
| 630 | 4-(4-Methylbenzimidazol-2-yl)-N-((piridyn-3-yl)methyl)-3-bromobenzamide | 4-Me | H | CH | CH | Br | |
| 631 | 4-(5,6-Dichlorobenzimidazol-2-yl)-N-((piridyn-3-yl)methyl)-3-bromobenzamide | 5-Cl | 6-Cl | CH | CH | Br | |
| 632 | 4-(4-Chloro-6-trifluoromethylbenzimidazol-2-yl)-N-((piridyn-3-yl)methyl)-3-bromobenzamide | 4-Cl | 6-$CF_3$ | CH | CH | Br | |
| 633 | 4-(1H-Naphth[2,3-d]imidazol-2-yl)-N-((piridyn-3-yl)methyl)-3-bromobenzamide | 5,6(—CH=CH—CH=CH—) | | CH | CH | Br | |
| 634 | 4-(6-Trifluoromethylbenzimidazol-2-yl)-N-((piridyn-3-yl)methyl)-3-bromobenzamide | 6-$CF_3$ | H | CH | CH | Br | |

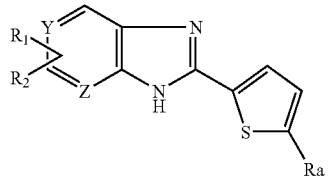

| Ex. No | Name | $R_1$ | $R_2$ | Y | Z | $R_a$ |
|---|---|---|---|---|---|---|
| 635 | 5-(6-Methoxybenzimidazol-2-yl)-N-(2,2,6,6-etramethylpiperidin-4-yl)-2-thiophenamide | 6-OMe | H | CH | CH | |
| 636 | 5-(5-Bromo-6,7-dimethylbenzimidazol-2-yl)-N-(2,2,6,6-tetramethylpiperidin-4-yl)-2-thiophenamide | 5-Br | 6-Me | CH | C(Me) | |
| 637 | 5-(5-Chloro-6-methylbenzimidazol-2-yl-N-(2,2,6,6-tetramethylpiperidin-4-yl)-2-thiophenamide | 5-Cl | 6-Me | CH | CH | |
| 638 | 5-(4-Methylbenzimidazol-2-yl)-N-(2,2,6,6-tetramethylpiperidin-4-yl)-2-thiophenamide | 4-Me | H | CH | CH | |
| 639 | 5-(5,6-Dichlorobenzimidazol-2-yl)-N-(2,2,6,6-tetramethylpiperidin-4-yl)-2-thiophenamide | 5-Cl | 6-Cl | CH | CH | |
| 640 | 5-(7-Hydroxybenzimidazol-2-yl)-N-(2,2,6,6-tetramethylpiperidin-4-yl)-2-thiophenamide | 7-OH | H | CH | CH | |
| 641 | 5-(5-Chloro-6-fluorobenzimidazol-2-yl)-N-(2,2,6,6-tetramethylpiperidin-4-yl)-2-thiophenamide | 5-Cl | 6-F | CH | CH | |

TABLE 2-continued

| | | | | | | |
|---|---|---|---|---|---|---|
| 642 | 5-(4-Chloro-6-trifluoro-methylbenzimidazol-2-yl)-N-(2,2,6,6-tetramethylpiperidin-4-yl)-2-thiophenamide | 4-Cl | 6-CF₃ | CH | CH | |
| 643 | 5-(1H-Naphth[2,3-d]imidazol-2-yl)-N-(2,2,6,6-tetramethyl-piperidin-4-yl)-2-thiophenamide | 5,6-(—CH=CH—CH=CH—) | | CH | CH | |
| 644 | 5-(6-Trifluoromethylbenzimidazol-2-yl)-N-(2,2,6,6-tetramethylpiperidin-4-yl)-2-thiophenamide | 6-CF₃ | H | CH | CH | |
| 645 | 5-(1H-Imidazo[4,5-b]pyridin-2-yl)-N-(2,2,6,6-tetramethylpiperidin-4-yl)-2-thiophenamide | H | H | N | CH | |
| 646 | 5-(6-Methoxybenzimidazol-2-yl)-N-(3-diethylaminopropyl)-2-thiophenamide | 6-OMe | H | CH | CH | |
| 647 | 5-(5-Bromo-6,7-dimethyl-benzimidazol-2-yl)-N-(3-diethylaminopropyl)-2-thiophenamide | 5-Br | 6-Me | CH | C(Me) | |
| 648 | 5-(5-Chloro-6-methyl-benzimidazol-2-yl)-N-(3-diethylaminopropyl)-2-thiophenamide | 5-Cl | 6-Me | CH | CH | |
| 649 | 5-(4-Methylbenzimidazol-2-yl)-N-(3-diethylaminopropyl)-2-thiophenamide | 4-Me | H | CH | CH | |
| 650 | 5-(5,6-Dichlorobenzimidazol-2-yl)-N-(3-diethylaminopropyl)-2-thiophenamide | 5-Cl | 6-Cl | CH | CH | |
| 651 | 5-(5-Chloro-6-fluorobenzimidazol-2-yl)-N-(3-diethylaminopropyl)-2-thiophenamide | 5-Cl | 6-F | CH | CH | |

TABLE 2-continued

| | | | | | |
|---|---|---|---|---|---|
| 652 | 5-(1H-Naphth[2,3-d]imidazol-2-yl)-N-(3-diethylaminopropyl)-2-thiophenamide | 5,6(—CH=CH—CH=CH—) | | CH | CH |
| 653 | 5-(6-Trifluoromethyl-benzimidazol-2-yl)-N-(3-diethylaminopropyl)-2-thiophenamide | 6-CF$_3$ | H | CH | CH |
| 654 | 5-(5-Bromo-6,7-dimethyl-benzimidazol-2-yl)-N-(3-diethylaminoethyl)-2-thiophenamide | 5-Br | 6-Me | CH | C(Me) |
| 655 | 5-(5,6-Dichlorobenzimidazol-2-yl)-N-(3-diethylaminoethyl)-2-thiophenamide | 5-Cl | 6-Cl | CH | CH |
| 656 | 5-(5-Chloro-6-fluoro-benzimidazol-2-yl)-N-(3-diethylaminoethyl)-2-thiophenamide | 5-Cl | 6-F | CH | CH |
| 657 | 5-(4-Chloro-6-trifluoromethylbenzimidazol-2-yl)-N-(3-diethylaminoethyl)-2-thiophenamide | 4-Cl | 6-CF$_3$ | CH | CH |
| 658 | 5-(1H-Naphth[2,3-d]imidazol-2-yl)-N-(3-diethylaminoethyl)-2-thiophenamide | 5,6(—CH=CH—CH=CH—) | | CH | CH |
| 659 | 5-(6-Trifluoromethyl-benzimidazol-2-yl)-N-(3-diethylaminoethyl)-2-thiophenamide | 6-CF$_3$ | H | CH | CH |
| 660 | 5-(1H-Naphth[2,3-d]imidazol-2-yl)-N-(1-azabicyclo[2.2.2]octan-3-yl)-2-thiophenamide | 5,6(—CH=CH—CH=CH—) | | CH | CH |
| 661 | 5-(6-Trifluoromethyl-benzimidazol-2-yl)-N-(1-azabicyclo[2.2.2]octan-3-yl)-2-thiophenamide | 6-CF$_3$ | H | CH | CH |
| 662 | 5-(6-Methoxybenzimidazol-2-yl)-N-[3-(morpholino)propyl]-2-thiophenamide | 6-OMe | H | CH | CH |

TABLE 2-continued

| | | | | | | |
|---|---|---|---|---|---|---|
| 663 | 5-(5-Bromo-6,7-dimethyl-benzimidazol-2-yl)-N-[3-(morpholino)propyl]-2-thiophenamide | 5-Br | 6-Me | CH | C(Me) | 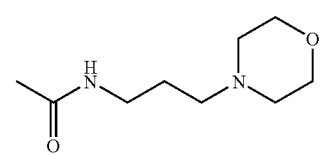 |
| 664 | 5-(5-Chloro-6-methyl-benzimidazol-2-yl)-N-[3-(morpholino)propyl]-2-thiophenamide | 5-Cl | 6-Me | CH | CH | 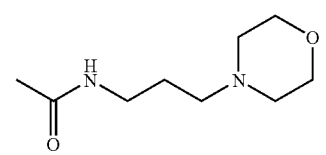 |
| 665 | 5-(4-Methylbenzimidazol-2-yl)-N-[3-(morpholino)propyl]-2-thiophenamide | 4-Me | H | CH | CH | 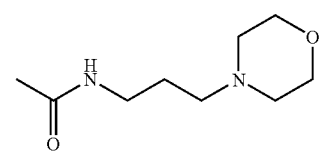 |
| 666 | 5-(5,6-Dichlorobenzimidazol-2-yl)-N-[3-(morpholino)propyl]-2-thiophenamide | 5-Cl | 6-Cl | CH | CH | 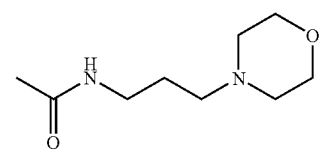 |
| 667 | 5-(5-Chloro-6-fluoro-benzimidazol-2-yl)-N-[3-(morpholino)propyl]-2-thiophenamide | 5-Cl | 6-F | CH | CH | 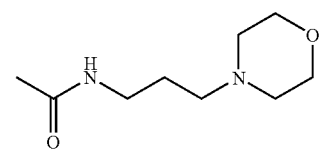 |
| 668 | 5-(4-Chloro-6-trifluoromethylbenzimidazol-2-yl)-N-[3-(morpholino)propyl]-2-thiophenamide | 4-Cl | 6-CF$_3$ | CH | CH | 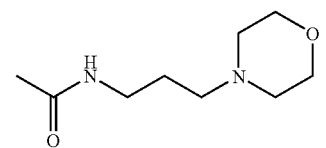 |
| 669 | 5-(1H-Naphth[2,3-d]imidazol-2-yl)-N-[3-(morpholino)propyl]-2-thiophenamide | 5,6(—CH=CH—CH=CH—) | | CH | CH | 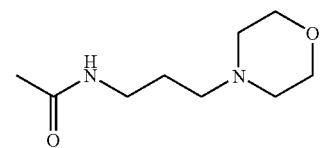 |
| 670 | 5-(6-Trifluoromethyl-benzimidazol-2-yl)-N-[3-(morpholino)propyl]-2-thiophenamide | 6-CF$_3$ | H | CH | CH | 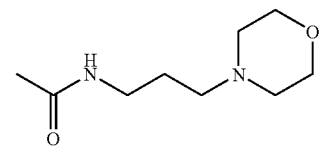 |
| 671 | 5(6-Methoxybenzimidazol-2-yl)-N-[3-[4-(3-chlorophenyl)piperazinyl]propyl]-2-thiophenamide | 6-OMe | H | CH | CH | 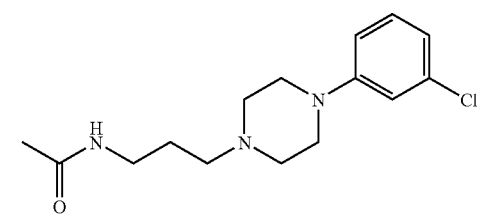 |

TABLE 2-continued

| | | | | | | |
|---|---|---|---|---|---|---|
| 672 | 5-(5-Chloro-6-methylbenzimidazol-2-yl)-N-[3-[4-(3-chlorophenyl)piperazinyl]propyl]-2-thiophenamide | 5-Cl | 6-Me | CH | CH | |
| 673 | 5-(4-Methylbenzimidazol-2-yl)-N-[3-[4-(3-chlorophenyl)piperazinyl]propyl]-2-thiophenamide | 4-Me | H | CH | CH | |
| 674 | 5-(5,6-Dichlorobenzimidazol-2-yl)-N-[3-[4-(3-chlorophenyl)piperazinyl]propyl]-2-thiophenamide | 5-Cl | 6-Cl | CH | CH | |
| 675 | 5-(7-Hydroxybenzimidazol-2-yl)-N-[3-[4-(3-chlorophenyl)piperazinyl]propyl]-2-thiophenamide | 7-OH | H | CH | CH | |
| 676 | 5-(5-Chloro-6-fluorobenzimidazol-2-yl)-N-[3-[4-(3-chlorophenyl)piperazinyl]propyl]-2-thiophenamide | 5-Cl | 6-F | CH | CH | |
| 677 | 5-(4-Chloro-6-trifluoromethylbenzimidazol-2-yl)-N-[3-[4-(3-chlorophenyl)piperazinyl]propyl]-2-thiophenamide | 4-Cl | 6-CF$_3$ | CH | CH | |
| 678 | 5-(1H-Naphth[2,3-d]imidazol-2-yl)-N-[3-[4-(3-chlorophenyl)piperazinyl]propyl]-2-thiophenamide | 5,6(—CH=CH—CH=CH—) | | CH | CH | |

TABLE 2-continued

| | | | | | | |
|---|---|---|---|---|---|---|
| 679 | 5-(6-Trifluoromethyl-benzimidazol-2-yl)-N-[3-[4-(3-chlorophenyl)piperazinyl]propyl]-2-thiophenamide | 6-CF$_3$ | H | CH | CH | 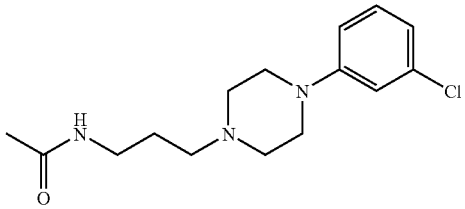 |
| 680 | 5-(1H-Imidazo[4,5-b]pyridin-2-yl)-N-[3-[4-(3-chlorophenyl)piperazinyl]propyl]-2-thiophenamide | H | H | N | CH | 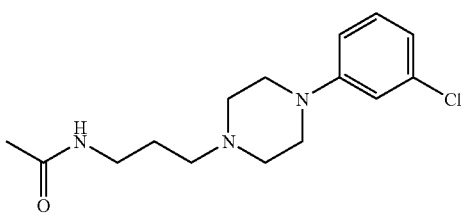 |
| 681 | 5-(6-Methoxybenzimidazol-2-yl)-N-(1-phenylmethylpiperidinyl-4-yl)-2-thiophenamide | 6-OMe | H | CH | CH | 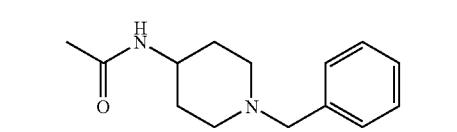 |
| 682 | 5-(5-Bromo-6,7-dimethyl-benzimidazol-2-yl)-N-(1-phenylmethylpiperidinyl-4-yl)-2-thiophenamide | 5-Br | 6-Me | CH | C(Me) | 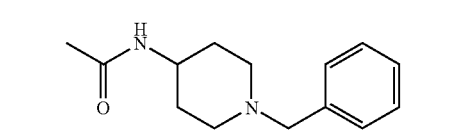 |
| 683 | 5-(5-Chloro-6-methyl-benzimidazol-2-yl)-N-(1-phenylmethyl-piperidinyl-4-yl)-2-thiophenamide | 5-Cl | 6-Me | CH | CH | 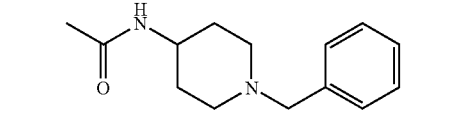 |
| 684 | 5-(5,6-Dichlorobenzimidazol-2-yl)-N-(1-phenylmethylpiperidinyl-4-yl)-2-thiophenamide | 5-Cl | 6-Cl | CH | CH | 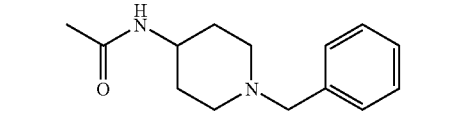 |
| 685 | 5-(7-Hydroxybenzimidazol-2-yl)-N-(1-phenylmethylpiperidinyl-4-yl)-2-thiophenamide | 7-OH | H | CH | CH | 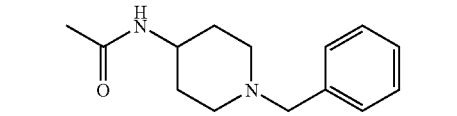 |
| 686 | 5-(5-Chloro-6-fluoro-benzimidazol-2-yl)-N-(1-phenylmethylpiperidinyl-4-yl)-2-thiophenamide | 5-Cl | 6-F | CH | CH | 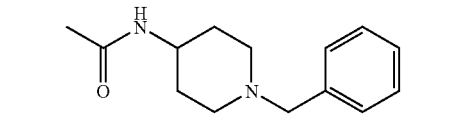 |
| 687 | 5-(4-Chloro-6-trifluoromethylbenzimidazol-2-yl)-N-(1-phenylmethylpiperidinyl-4-yl)-2-thiophenamide | 4-Cl | 6-CF$_3$ | CH | CH | 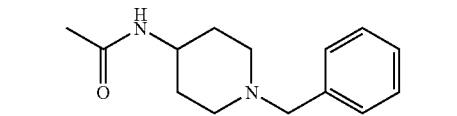 |
| 688 | 5-(1H-Naphth[2,3-d]imidazol-2-yl)-N-(1-phenylmethylpiperidinyl-4-yl)-2-thiophenamide | 5,6(—CH=CH—CH=CH—) | | CH | CH | 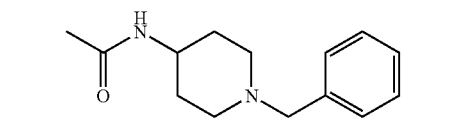 |

TABLE 2-continued

| | | | | | |
|---|---|---|---|---|---|
| 689 | 5-(6-Trifluoromethyl-benzimidazol-2-yl)-N-(1-phenylmethylpiperi-dinyl-4-yl)-2-thiophenamide | 6-CF$_3$ | H | CH | CH |
| 690 | 5-(1H-Imidazo[4,5-b]pyridin-2-yl)-N-(1-phenylmethylpiperi-dinyl-4-yl)-2-thiophenamide | H | H | N | CH |
| 691 | 5-(1H-Purin-8-yl)-N-(1-phenylmethylpiperi-dinyl-4-yl)-2-thiophenamide | H | H | N | N |
| 692 | 5-(6-Methoxybenzi-midazol-2-yl)-N-[(3-pyridyl)methyl]-2-thiophenamide | 6-OMe | H | CH | CH |
| 693 | 5-(5-Bromo-6,7-dimethyl-benzimidazol-2-yl)-N-[(3-pyridyl)methyl]-2-thiophenamide | 5-Br | 6-Me | CH | C(Me) |
| 694 | 5-(5-Chloro-6-methylbenzi-midazol-2-yl)-N-[(3-pyridyl)methyl]-2-thiophenamide | 5-Cl | 6-Me | CH | CH |
| 695 | 5-(4-Methylbenzi-midazol-2-yl)-N-[(3-pyridyl)methyl]-2-thiophenamide | 4-Me | H | CH | CH |
| 696 | 5-(5,6-Dichlorobenzi-midazol-2-yl)-N-[(3-pyridyl)methyl]-2-thiophenamide | 5-Cl | 6-Cl | CH | CH |
| 697 | 5-(5-Chloro-6-fluoro-benzimidazol-2-yl)-N-[(3-pyridyl)methyl]-2-thiophenamide | 5-Cl | 6-F | CH | CH |
| 698 | 5-(4-Chloro-6-trifluoro-methylbenzi-midazol-2-yl)-N-[(3-pyridyl)methyl]-2-thiophenamide | 4-Cl | 6-CF$_3$ | CH | CH |

TABLE 2-continued

| | | | | | | |
|---|---|---|---|---|---|---|
| 699 | 5-(1H-Naphth[2,3-d]imidazol-2-yl)-N-[(3-pyridyl)methyl]-2-thiophenamide | 5,6(—CH=CH—CH=CH—) | | CH | CH | |
| 700 | 5-(6-Trifluoromethyl-benzimidazol-2-yl)-N-[(3-pyridyl)methyl]-2-thiophenamide | 6-CF$_3$ | H | CH | CH | |
| 701 | 5-(1H-Imidazo[4,5-b]pyridin-2-yl)-N-[(3-pyridyl)methyl]-2-thiophenamide | H | H | N | CH | |
| 702 | 5-(6-Methoxybenzimidazol-2-yl)-N-(piperidinyl-4-yl)-2-thiophenamide | 6-OMe | H | CH | CH | |
| 703 | 5-(5-Bromo-6,7-methyl-benzimidazol-2-yl)-N-(piperidinyl-4-yl)-2-thiophenamide | 5-Br | 6-Me | CH | C(Me) | |
| 704 | 5-(5-Chloro-6-methyl-benzimidazol-2-yl)-N-(piperidinyl-4-yl)-2-thiophenamide | 5-Cl | 6-Me | CH | CH | |
| 705 | 5-(4-Methylbenzimidazol-2-yl)-N-(piperidinyl-4-yl)-2-thiophenamide | 4-Me | H | CH | CH | |
| 706 | 5-(5,6-Dichlorobenzimidazol-2-yl)-N-(piperidinyl-4-yl)-2-thiophenamide | 5-Cl | 6-Cl | CH | CH | |
| 707 | 5-(5-Chloro-6-fluoro-benzimidazol-2-yl)-N-(piperidinyl-4-yl)-2-thiophenamide | 5-Cl | 6-F | CH | CH | |
| 708 | 5-(4-Chloro-6-trifluoromethylbenzimidazol-2-yl)-N-(piperidinyl-4-yl)-2-thiophenamide | 4-Cl | 6-CF$_3$ | CH | CH | |
| 709 | 5-(1H-Naphth[2,3-d]imidazol-2-yl)-N-(piperidinyl-4-yl)-2-thiophenamide | 5,6-(—CH=CH—CH=CH—) | | CH | CH | |

TABLE 2-continued

| | | | | | | |
|---|---|---|---|---|---|---|
| 710 | 5-(6-Trifluoromethyl-benzimidazol-2-yl)-N-(piperidinyl-4-yl)-2-thiophenamide | 6-CF$_3$ | H | CH | CH | 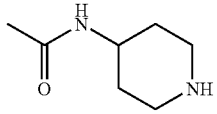 |
| 711 | 5-(1H-Imidazo[4,5-b]pyridin-2-yl)-N-(piperidinyl-4-yl)-2-thiophenamide | H | H | N | CH | 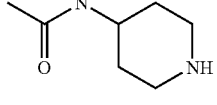 |
| 712 | 5-(6-Methoxybenzimidazol-2-yl)-N-[3-[4-(2-methoxy-5-chlorophenyl)piperazinyl]propyl]-2-thiophenamide | 6-OMe | H | CH | CH | 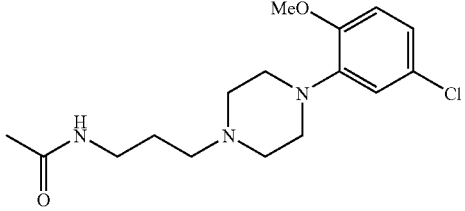 |
| 713 | 5-(5-Chloro-6-methyl-benzimidazol-2-yl)-N-[3-[4-(2-methoxy-5-chloro-phenyl)piperazinyl]propyl]-2-thiophenamide | 5-Cl | 6-Me | CH | CH | 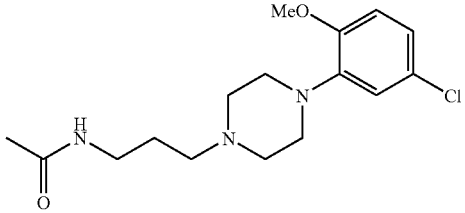 |
| 714 | 5-(4-Methylbenzimidazol-2-yl)-N-[3-[4-(2-methoxy-5-chlorophenyl)piperazinyl]propyl]-2-thiophenamide | 4-Me | H | CH | CH | 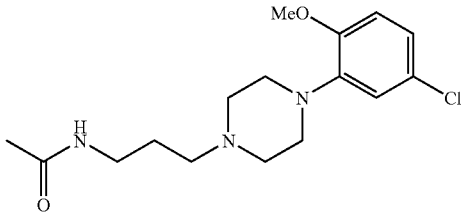 |
| 715 | 5-(5,6-Dichlorobenzimidazol-2-yl)-N-[3-[4-(2-methoxy-5-chlorophenyl)piperazinyl]propyl]-2-thiophenamide | 5-Cl | 6-Cl | CH | CH | 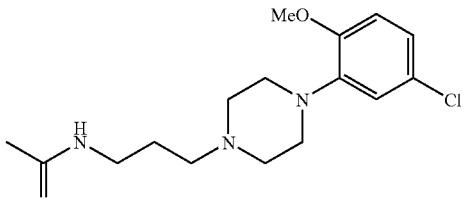 |
| 716 | 5-(7-Hydroxybenzimidazol-2-yl)-N-[3-[4-(2-methoxy-5-chlorophenyl)piperazinyl]propyl]-2-thiophenamide | 7-OH | H | CH | CH | 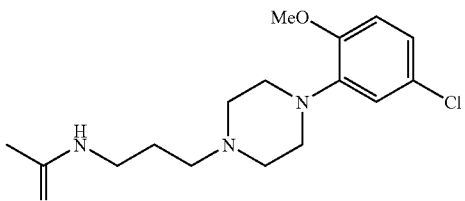 |
| 717 | 5-(5-Chloro-6-fluoro-benzimidazol-2-yl)-N-[3-[4-(2-methoxy-5-chlorophenyl)piperazinyl]propyl]-2-thiophenamide | 5-Cl | 6-F | CH | CH | 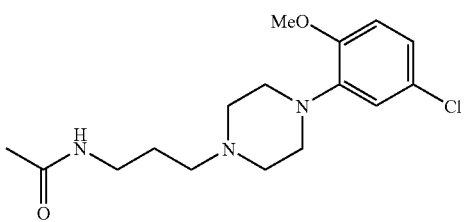 |

TABLE 2-continued

| | | | | | | |
|---|---|---|---|---|---|---|
| 718 | 5-(4-Chloro-6-trifluoro-methylbenzimi-dazol-2-yl)-N-[3-[4-(2-methoxy-5-chlorophenyl)pipera-zinyl]propyl]-2-thiophenamide | 4-Cl | 6-CF$_3$ | CH | CH | 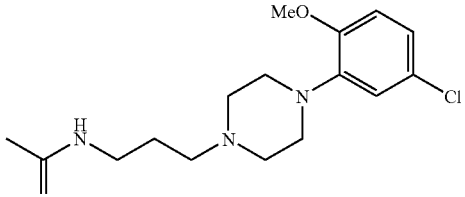 |
| 719 | 5-(1H-Naphth[2,3-d]imidazol-2-yl)-N-[3-[4-(2-methoxy-5-chlorophenyl)pipera-zinyl]propyl]-2-thiophenamide | 5,6(—CH=CH—CH=CH—) | | CH | CH | 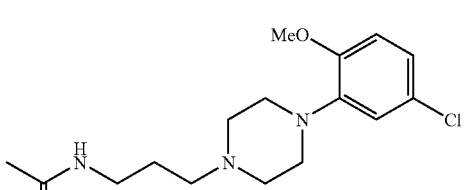 |
| 720 | 5-(6-Trifluoromethyl-benzimidazol-2-yl)-N-[3-[4-(2-methoxy-5-chloro-phenyl)pipera-zinyl]propyl]-2-thiophenamide | 6-CF$_3$ | H | CH | CH | 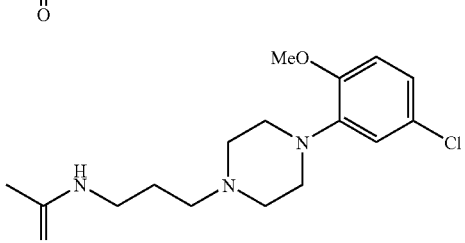 |
| 721 | 5-(1H-Imidazo[4,5-b]pyridin-2-yl)-N-[3-[4-(2-methoxy-5-chlorophenyl)pipera-zinyl]propyl]-2-thiophenamide | H | H | N | CH | 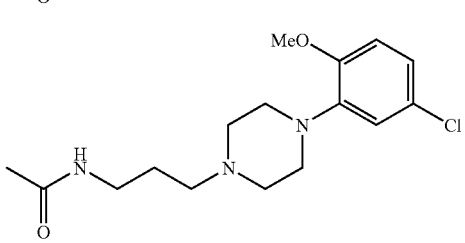 |
| 722 | 5-(1H-Purin-8-yl)-N-[3-[4-(2-methoxy-5-chlorophenyl)pipera-zinyl]propyl]-2-thiophenamide | H | H | N | N | 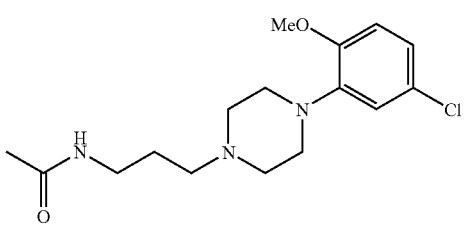 |
| 723 | 5-(5-Bromo-6,7-dimethyl-benezimidazol-2-yl)-N-(3-aminopropyl)-2-thiophenamide | 5-Br | 6-Me | CH | C(Me) | 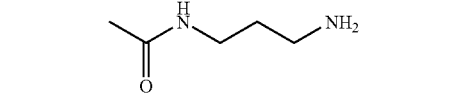 |
| 724 | 5-(5-Chloro-6-methyl-benzimidazol-2-yl)-N-(3-aminopropyl)-2-thiophenamide | 5-Cl | 6-Me | CH | CH | 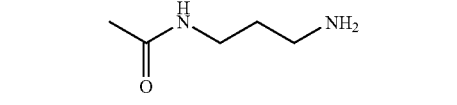 |
| 725 | 5-(4-Methylbenzi-midazol-2-yl)-N-(3-aminopropyl)-2-thiophenamide | 4-Me | H | CH | CH | 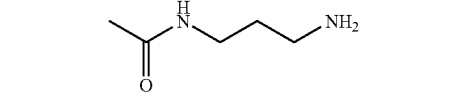 |
| 726 | 5-(5,6-Dichlorobenzi-midazol-2-yl)-N-(3-aminopropyl)-2-thiophenamide | 5-Cl | 6-Cl | CH | CH | 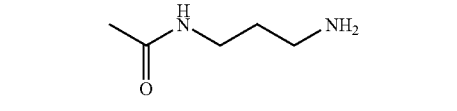 |

TABLE 2-continued

| | | | | | | |
|---|---|---|---|---|---|---|
| 727 | 5-(5-Chloro-6-fluoro-benzimidazol-2-yl)-N-(3-aminopropyl)-2-thiophenamide | 5-Cl | 6-F | CH | CH | ![structure](acetamide with NH-CH2CH2CH2-NH2) |
| 728 | 5-(4-Chloro-6-trifluoro-methylbenzimidazol-2-yl)-N-(3-amino-propyl)-2-thiophenamide | 4-Cl | 6-CF$_3$ | CH | CH | (same sidechain) |
| 729 | 5-(1H-Naphth[2,3-d]imidazol-2-yl)-N-(3-amino-propyl)-2-thiopheamide | 5,6(—CH=CH—CH=CH—) | | CH | CH | (same sidechain) |
| 730 | 5-(6-Trifluoro-methylbenzi-midazol-2-yl)-N-(3-aminopropyl)-2-thiophenamide | 6-CF$_3$ | H | CH | CH | (same sidechain) |

Biological Assays

Background. It is known that, upon attachment to bone, an electrogenic H$^+$-adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., *Science*, 245, 855 (1989)] and than confirmed by Bekker [P. J. Bekker et al., *J. Bone Min. Res.*, 5, 569 (1990)] and Väänänen [H. K. Väänänen et al., *J. Cell. Biol.*, 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin A$_1$, a selective inhibitor of vacuolar H$^+$-ATPases [J. E. Bowman et al., *Proc. Natl. Acad. Sci. USA*, 85, 7972 (1988)], whilst it was not inhibited by ouabain, an inhibitor of Na$^+$/K$^+$-ATPases; sodium orthovanadate, an inhibitor of P-ATPases, or by omeprazole or SCH 28080, both of which are inhibitors of gastric H$^+$/K$^+$-ATPase [J. P. Mattsson et al., *Acta Physiol. Scand.*, 146, 253 (1992)].

It is known that specific inhibitors of vacuolar ATPases, such as bafilomycin A$_1$, are able to inhibit bone resorption in osteoclast cultures [K. Sundquist et al., *Biochem. Biophys. Res. Commun.* 168, 309–313 (1990)]

Inhibition of Proton Transport and v-ATPase Activity in Membrane Vesicles

Preparation of human osteoclast microsomal vesicles. Osteoclast-like giant cells isolated from osteoclastoma tumor were homogenized with a glass-teflon homogenizer (1000 rpm×20 strokes), and the material was centrifuged at 6000×gmax for 20 minutes. The resulting pellet was then spun at 100000×gmax for 60 minutes to pellet the microsomal fraction. Resuspended in 1 ml of isolation medium pH 7.4, frozen by liquid nitrogen immersion and stored at −80° C. until used.

Proton transport in membrane vesicles was assessed, semi-quantitatively, by measuring the initial slope of fluorescence quench of acridine orange (excitation 490 nm; emission 530 nm) after addition of 5–20 µl of membrane vesicles in 1 ml of buffer containing 0.2 M sucrose, 50 mM KCl, 10 mM Hepes pH 7.4, 1 mM ATP.Na2, 1 mM CDTA, 5 µM valinomycin and 4 µM acridine orange. The reaction was started by addition of 5 mM MgSO$_4$. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin A1. The reaction medium contained 1 mM ATP, 10 mM HEPES-Tris pH 8, 50 mM KCl, 5 uM valinomycin, 5 uM nigericin, 1 mM CDTA-Tris, 100 uM ammonium molybdate, 0.2 M sucrose and membranes (20 ug protein/ml). The reaction was initiated by MgSO$_4$ (8-arm pipette) and stopped, after 30 min, by addition of 4 volumes of the malachite green reagent (96-arm pipette) prepared according to Chan [*Anal. Biochem.* 157, 375 (1986)]. Absorbance at 650 nm was measured after 2 min using a microplate reader. Results are expressed as nmol (Pi)×mg protein$^{-1}$×min$^{-1}$ and, for each experiment, represent the mean±sem of triplicates.

Pharmacological Data

Compounds described in the present invention are able to inhibit bafilomycin-sensitive ATPase of human osteoclasts in a range from 2 nM to 15 µM.

What is claimed is:

1. A compound of formula (I)

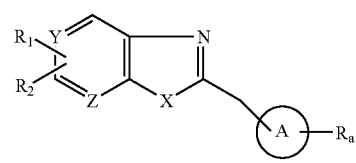

(I)

or a salt thereof, or a solvate thereof, wherein;

X represents NR$_b$, wherein R$_b$ represents hydrogen, unsubstituted or substituted C$_{1-6}$ alkyl or unsubstituted or substituted C$_{1-6}$ alkylcarbonyl;

Y and Z each independently represent, CH, $CR_1$ or $CR_2$;

A represents an unsubstituted or substituted aryl group;

$R_a$ represents —$C(O)NR_sR_t$ wherein $R_s$ represents substituted aryl, unsubstituted or substituted aryl $C_{1-6}$ alkyl, unsubstituted or substituted heterocyclyl or an unsubstituted heterocyclyl $C_{1-6}$ alkyl group, $R_t$ represents hydrogen, unsubstituted or substituted $C_{1-6}$ alkyl, unsubstituted or substituted $C_{3-8}$ cycloalkyl, unsubstituted or substituted $C_{1-6}$ alkenyl;

$R_1$ and $R_2$ each independently represents hydrogen, hydroxy, amino, $C_{1-6}$ alkoxy, unsubstituted or substituted aryloxy, unsubstituted or substituted benzyloxy, $C_{1-6}$ alkylamino, di($C_{1-6}$ alkyl)amino, halo, trifluoromethyl, trifluoromethoxy, nitro, $C_{1-6}$ alkyl, carboxy, alkoxycarbonyl, carbamoyl, $C_{1-6}$ alkylcarbamoyl, or $R_1$ and $R_2$ together represent methylenedioxy, —$(CH=CH)_{2-3}$—, carbonyldioxy or carbonyldiamino.

2. A process for the preparation of a compound of formula (I) according to claim 1, or a salt thereof or a solvate thereof, wherein said process comprises the steps of:

(a) amidation of a carboxylic acid having the formula:

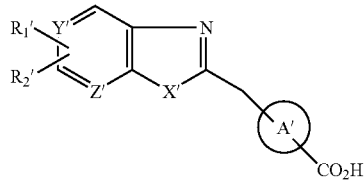

wherein X', Y', Z', A', $R_{1'}$, and $R_{2'}$ each respectively represent X, Y, Z, A, $R_1$ and $R_2$ as defined in claim 1 or a protected form thereof, with an amine having the formula:

HNR$_{s'}$R$_{t'}$ wherein $R_{s'}$ and $R_{t'}$ each respectively represent $R_s$ and $R_t$ as defined in claim 1 or a protected form thereof, and (b) optionally preparing a salt or solvate thereof.

3. A process for the preparation of a compound of formula (I) according to claim 2, further comprising the steps of:

(i) converting the compound of formula (I) formed in step (a) or step (b) into another compound of formula (I);

(ii) removing any protecting group; and (iii) preparing a salt or a solvate thereof.

4. A process for the preparation of a compound of formula (I) according to claim 1, or a salt thereof or a solvate thereof, wherein said process comprises cleavage of a compound of formula (VIII) at the N-Resin bond

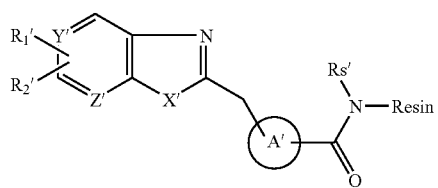

wherein X', Y', Z', A', $R_{1'}$, $R_{2'}$ and $R_{s'}$ each respectively represent X, Y, Z, A, $R_1$, $R_2$ and $R_s$ as defined in claim 1.

5. A pharmaceutical composition comprising a compound of formula (I) according to claim 1 or a pharmaceutically acceptable salt thereof or a pharmaceutically acceptable solvate thereof, and a pharmaceutically acceptable carrier therefor.

6. A method for the treatment of osteoporosis and related osteopenic diseases in a human or non-human mammal, which comprises administering an effective, non-toxic, amount of a compound of formula (I) according to claim 1 or a pharmaceutically acceptable salt thereof or a pharmaceutically acceptable solvate thereof, to a human or non-human mammal in need thereof.

7. A method for the treatment of melanoma, breast cancer, liver cancer, colon cancer and ovarian cancer, in a human or non-human mammal, which method comprises administering an effective, non-toxic, amount of a compound of formula (I) according to claim 1 or a pharmaceutically acceptable salt thereof or a pharmaceutically acceptable solvate thereof, to a human or non-human mammal in need thereof.

8. A compound of formula (I)

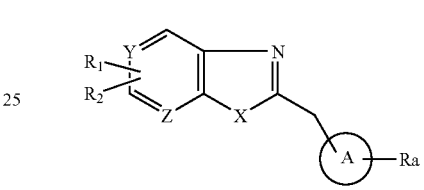

(I)

or a salt thereof, or a solvate thereof, wherein;

X represents $NR_b$, wherein $R_b$ represents hydrogen, unsubstituted or substituted $C_{1-6}$ alkyl or unsubstituted or substituted $C_{1-6}$ alkylcarbonyl;

Y and Z each independently represent CH, $CR_1$ or $CR_2$;

A represents an unsubstituted or substituted aryl group;

$R_a$ represents —$C(O)NR_sR_t$ wherein $R_s$ represents substituted aryl, unsubstituted or substituted aryl $C_{1-6}$ alkyl, unsubstituted or substituted heterocyclyl or an unsubstituted heterocyclyl $C_{1-6}$ alkyl group;

$R_t$ represents hydrogen, unsubstituted or substituted $C_{1-6}$ alkyl, unsubstituted or substituted $C_{3-8}$ cycloalkyl, unsubstituted or substituted $C_{1-6}$ alkenyl;

$R_1$ and $R_2$ each independently represents hydrogen, hydroxy, amino, $C_{1-6}$ alkoxy, unsubstituted or substituted aryloxy, unsubstituted or substituted benzyloxy, $C_{1-6}$ alkylamino, di($C_{1-6}$ alkyl)amino, halo, trifluoromethyl, trifluoromethoxy, nitro, $C_{1-6}$ alkyl, carboxy, alkoxycarbonyl, carbamoyl, $C_{1-6}$ alkylcarbamoyl, or $R_1$ and $R_2$ together represent methylenedioxy, —$(CH=CH)_{2-3}$—, carbonyldioxy or carbonyldiamino, wherein:

said heterocyclic groups are selected from aromatic and non-aromatic, single and fused rings containing 4–7 ring members and up to four heteroatoms in each ring selected from oxygen, nitrogen and sulphur, which rings may be unsubstituted or substituted by up to three substituents;

said substituted aryl and substituted heterocyclyl groups are substituted with up to three substituents selected from aryl, arylcarbonyl, alkylthio, halo, alkyl, alkenyl, substituted alkenyl, arylalkyl, alkoxy, alkoxyalkyl, haloalkyl, haloalkyloxy, hydroxy, hydroxyalkyl, nitro, amino, cyano, cyanoalkyl, mono- and di-N-alkylamino, acyl, acylamino, N-alkylacylamino, acyloxy, carboxy, carboxyalkyl, carboxyalkenyl, carbamoyl, mono- and di-N-alkylcarbamoyl, alkoxycarbonyl, aryloxy, arylthio, aralkyloxy, aryloxycarbonyl, aminosulphonyl, alkylaminosulphonyl, alkylthio, alkylsulphonyl, cycloalkyl, heterocyclyl, or a group —NR$_u$R$_v$ wherein R$_u$ and R$_v$ each independently represent hydrogen, alkyl or alkylcarbonyl;

said substituted alkyl, alkyl-containing, and alkenyl groups are substituted with up to three groups selected from aryl, heterocyclyl, alkylthio, alkoxy, arylalkoxy, amino, mono-or di-alkylamino, cycloalkyl, cycloalkenyl, carboxy and esters thereof, mono or dialkylaminosulphonyl, aminosulphonyl, cyano, alkylcarbonylamino, arylcarbonylamino, hydroxy, and halogen.

* * * * *